United States Patent
Celmerowski et al.

(10) Patent No.: US 10,285,736 B2
(45) Date of Patent: May 14, 2019

(54) CONNECTION ELEMENT AND SPINE STABILIZATION SYSTEM

(71) Applicant: Aesculap AG, Tuttlingen (DE)

(72) Inventors: Beate Celmerowski, Gunningen (DE); Sven Krueger, Trossingen (DE); Jens Beger, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 95 days.

(21) Appl. No.: 15/351,602

(22) Filed: Nov. 15, 2016

(65) Prior Publication Data
US 2017/0056073 A1 Mar. 2, 2017

Related U.S. Application Data

(63) Continuation of application No. 14/480,745, filed on Sep. 9, 2014, now Pat. No. 9,532,808.

(30) Foreign Application Priority Data

Sep. 16, 2013 (DE) .................... 10 2013 110 173

(51) Int. Cl.
*A61B 17/70* (2006.01)
(52) U.S. Cl.
CPC ........ *A61B 17/7011* (2013.01); *A61B 17/701* (2013.01); *A61B 17/7005* (2013.01); *A61B 17/7019* (2013.01); *A61B 17/7026* (2013.01); *A61B 17/7031* (2013.01); *A61B 17/7034* (2013.01); *A61B 17/7032* (2013.01)
(58) Field of Classification Search
CPC ............ A61B 17/7005; A61B 17/7001; A61B 17/7004; A61B 17/701; A61B 17/7011; A61B 17/7019; A61B 17/7028
See application file for complete search history.

(56) References Cited

U.S. PATENT DOCUMENTS

| | | |
|---|---|---|
| 6,626,904 B1 | 9/2003 | Jammet et al. |
| 8,192,468 B2 | 6/2012 | Biedermann et al. |
| 8,252,025 B2 | 8/2012 | Viker |
| 8,414,621 B2 | 4/2013 | Biedermann et al. |

(Continued)

FOREIGN PATENT DOCUMENTS

| | | |
|---|---|---|
| DE | 9402695 | 5/1994 |
| DE | 202010008865 | 2/2011 |

(Continued)

OTHER PUBLICATIONS

Zylinder (Geometrie), German Wikipedia, [retrieved from the Internet], retrieved on Jun. 4, 2016, <URL:https://de.wikipedia.org/wiki/Zylinder_(Geometrie)>, 8 pages.

*Primary Examiner* — Ellen C Hammond
(74) *Attorney, Agent, or Firm* — Lipsitz & McAllister, LLC

(57) ABSTRACT

The present invention relates to a connection element for a spine stabilization system which comprises a first end for fixing to a first bone fixation device, a second end for fixing to a second bone fixation device and an intermediate portion arranged or formed between the two ends and defining a longitudinal axis. At least one of the two ends takes the form of a coupling element for fixing the connection element to a bone fixation device in at least one defined orientation relative to the longitudinal axis. The coupling element has a shape other than a circular cylinder.

20 Claims, 48 Drawing Sheets

(56) References Cited

U.S. PATENT DOCUMENTS

| | | |
|---|---|---|
| 8,486,111 B2 | 7/2013 | Ritland |
| 8,641,734 B2 | 2/2014 | Moumene et al. |
| 8,663,284 B2 | 3/2014 | Beger et al. |
| 2006/0064090 A1* | 3/2006 | Park .................. A61B 17/7005 606/250 |
| 2006/0184171 A1 | 8/2006 | Biedermann et al. |
| 2008/0177318 A1 | 7/2008 | Veldman et al. |
| 2008/0183215 A1* | 7/2008 | Altarac .............. A61B 17/7005 606/265 |
| 2008/0312693 A1* | 12/2008 | Trautwein .......... A61B 17/1757 606/246 |
| 2010/0042155 A1 | 2/2010 | Biedermann et al. |
| 2010/0211104 A1 | 8/2010 | Moumene et al. |
| 2010/0256683 A1 | 10/2010 | Iott et al. |
| 2011/0009906 A1* | 1/2011 | Hestad ............... A61B 17/7005 606/278 |
| 2012/0253401 A1 | 10/2012 | Clark et al. |
| 2013/0066375 A1 | 3/2013 | Biedermann et al. |
| 2013/0211454 A1 | 8/2013 | Beger et al. |

FOREIGN PATENT DOCUMENTS

| | | | |
|---|---|---|---|
| EP | 1658815 A1 * | 5/2006 | ......... A61B 17/7011 |
| EP | 2153786 | 10/2011 | |
| EP | 1658815 | 3/2012 | |
| EP | 2505155 | 10/2012 | |
| FR | 2846222 | 4/2004 | |
| FR | 2846223 | 4/2004 | |
| FR | 2846223 A1 * | 4/2004 | ......... A61B 17/7005 |
| WO | 2010/114880 | 10/2010 | |
| WO | 2011/008392 | 1/2011 | |
| WO | 2012/048690 | 4/2012 | |

\* cited by examiner

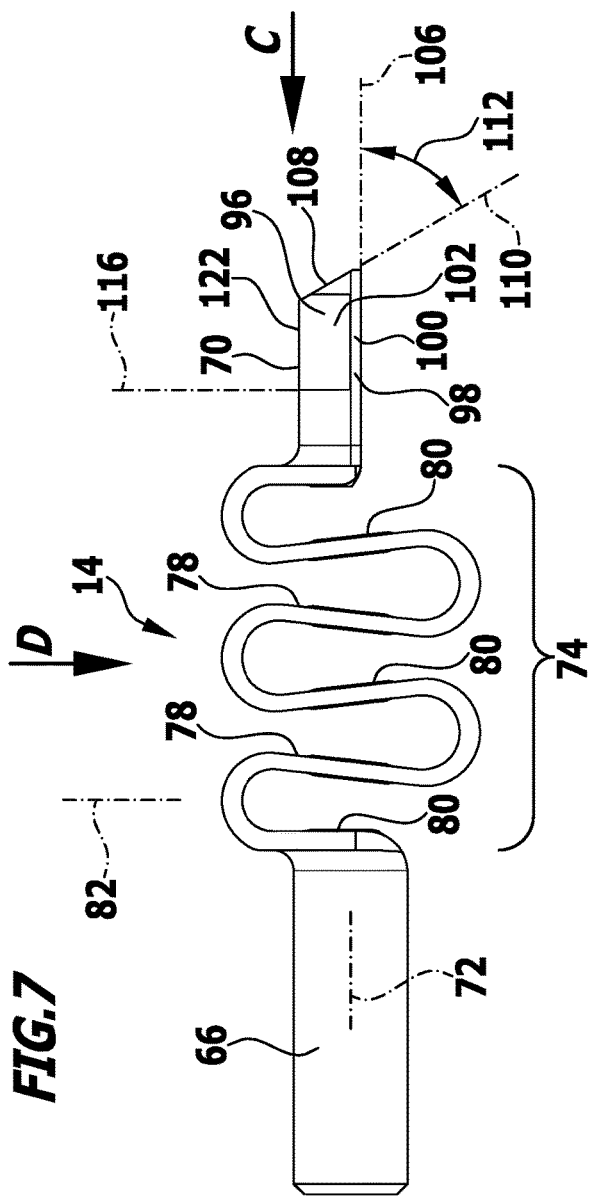
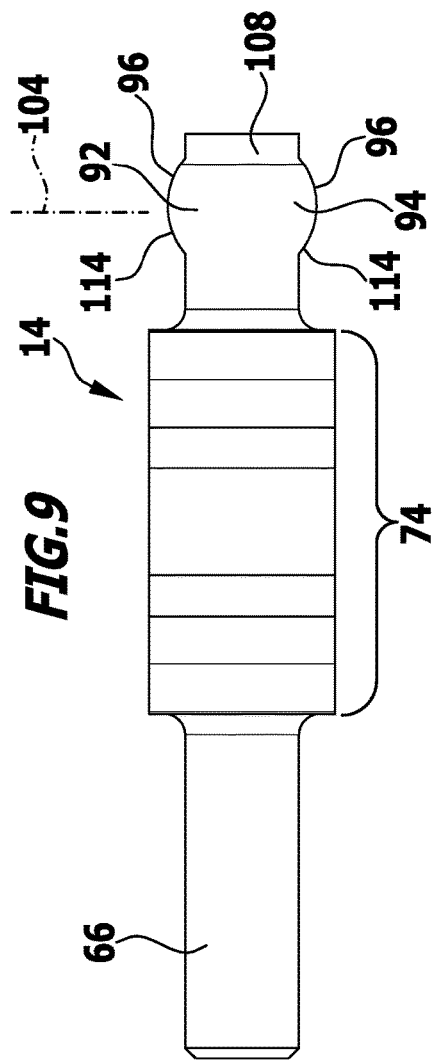
FIG.7
FIG.8
FIG.9

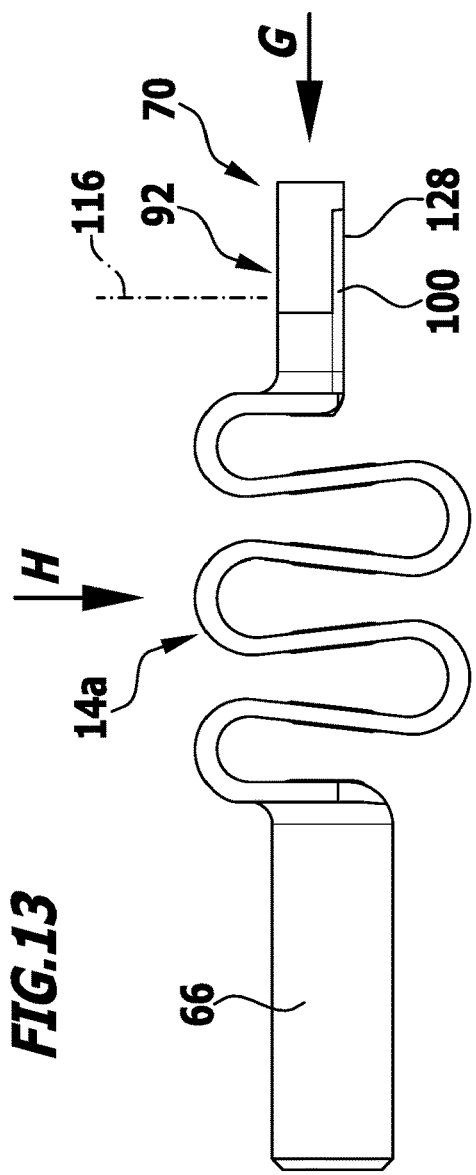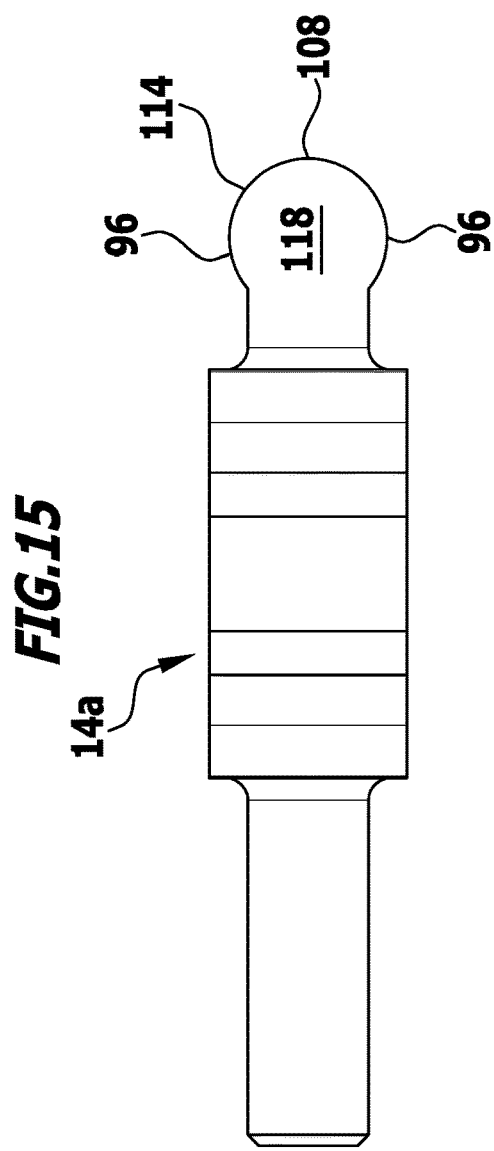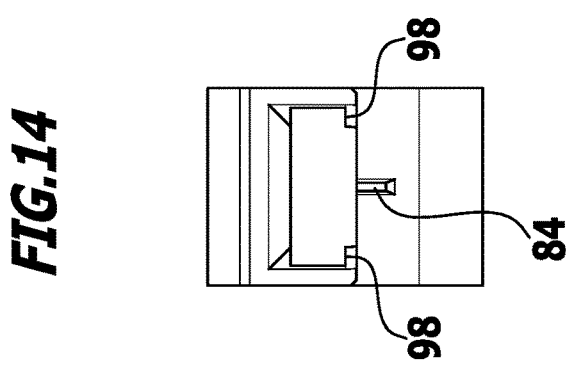

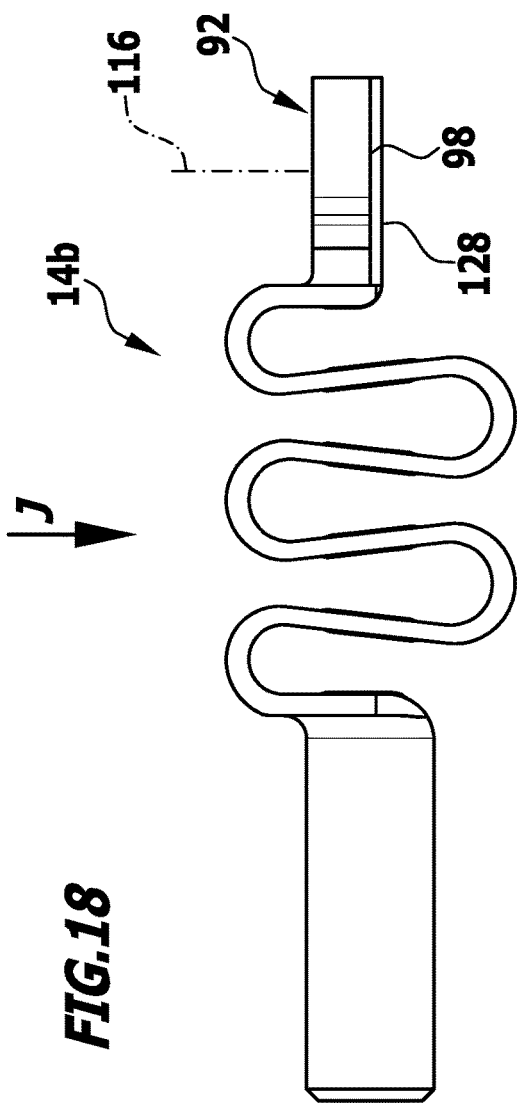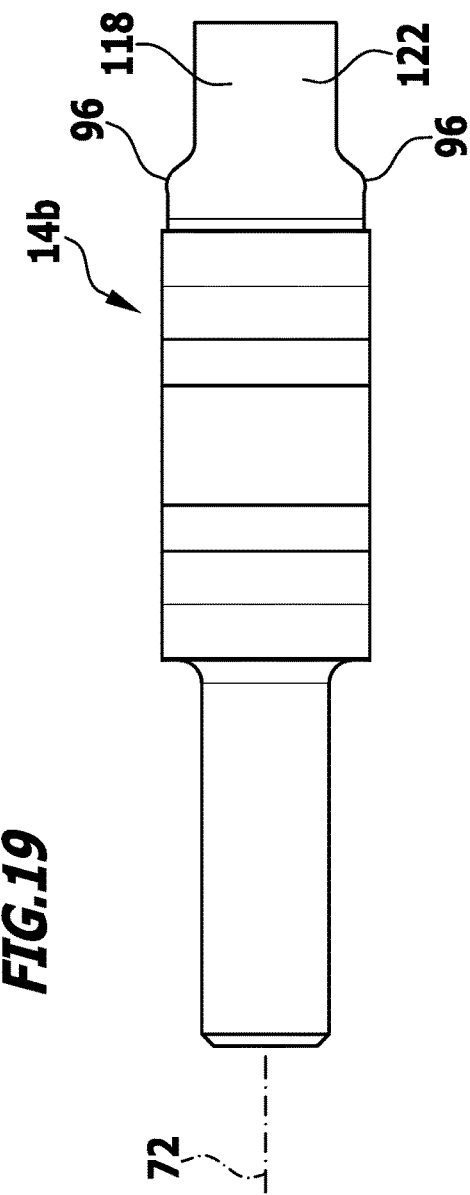
FIG.18
FIG.19

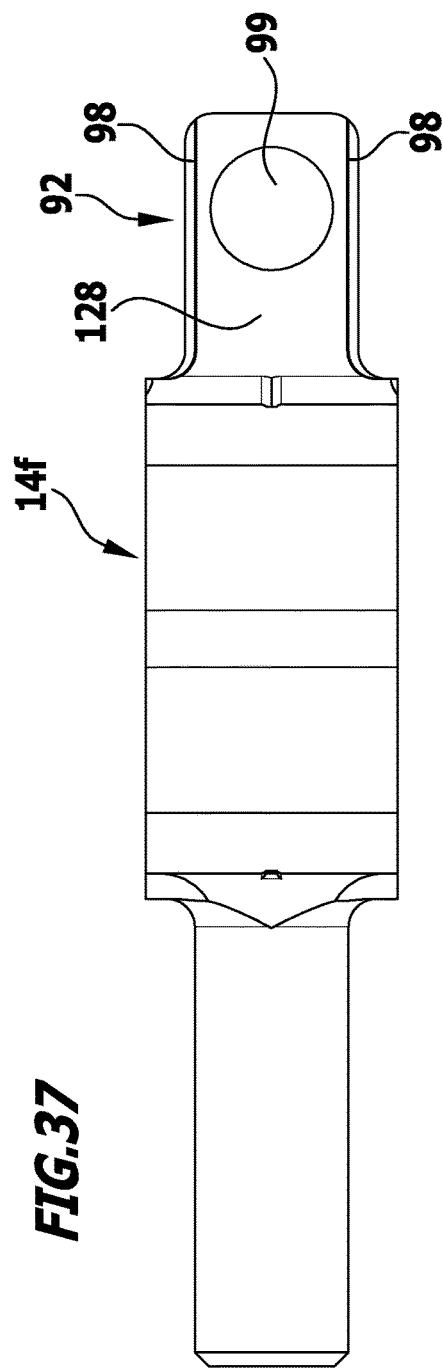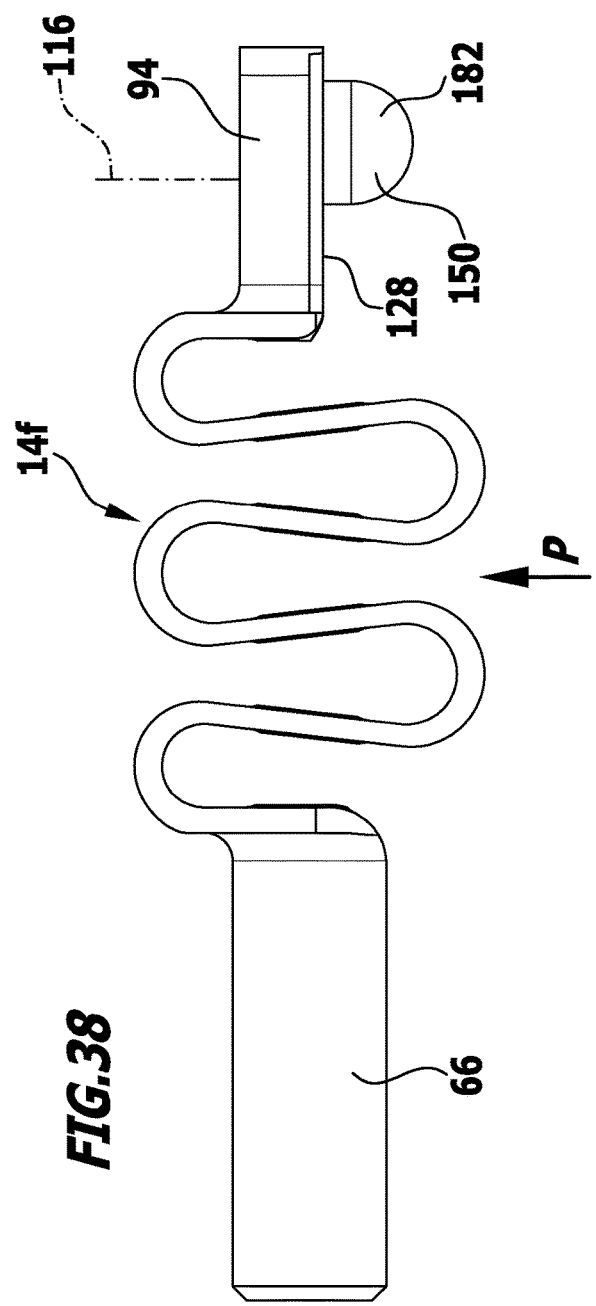
FIG.37
FIG.38

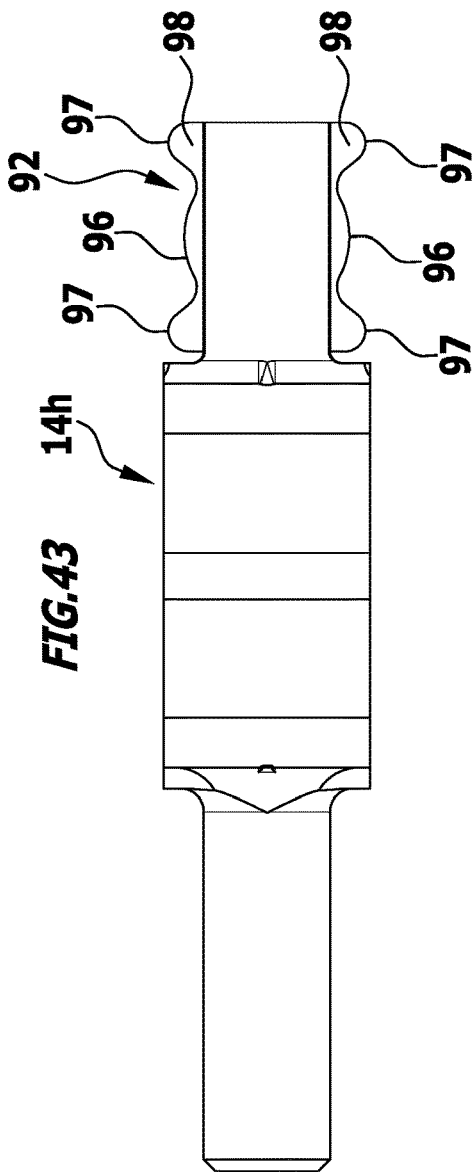
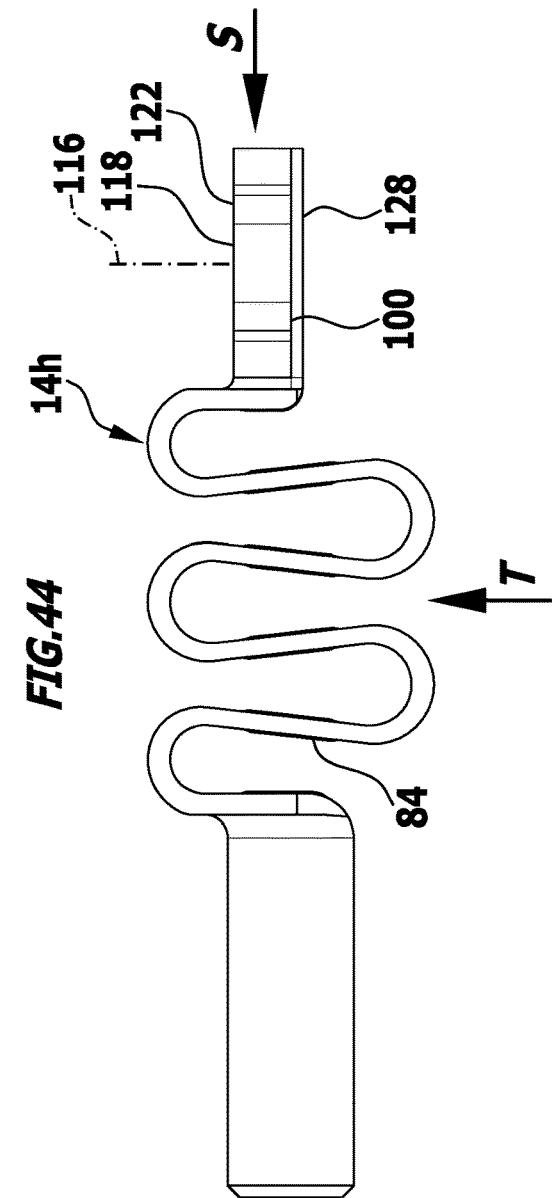
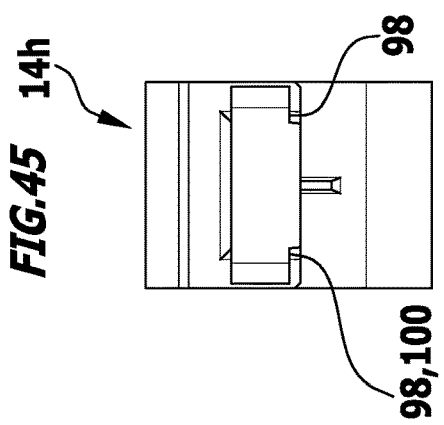
FIG.43
FIG.44
FIG.45

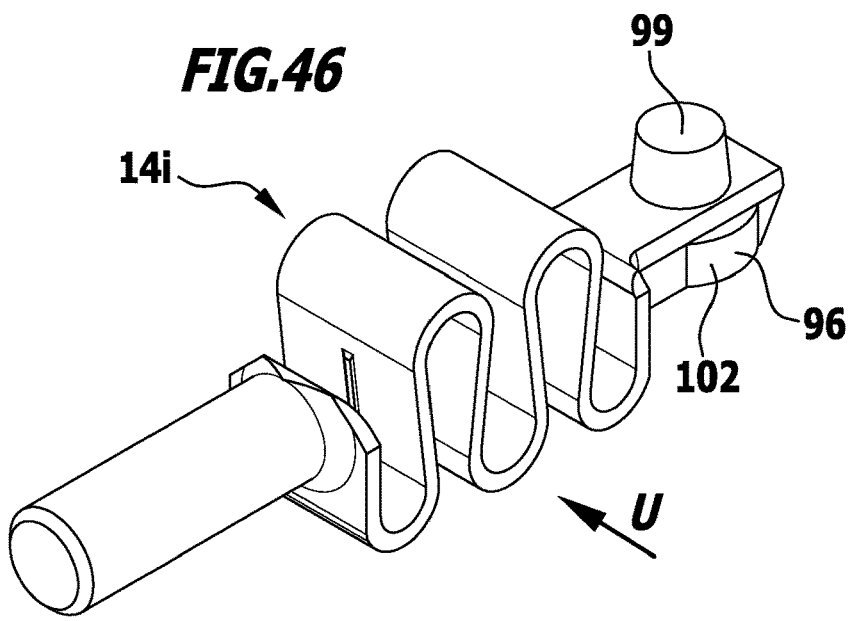
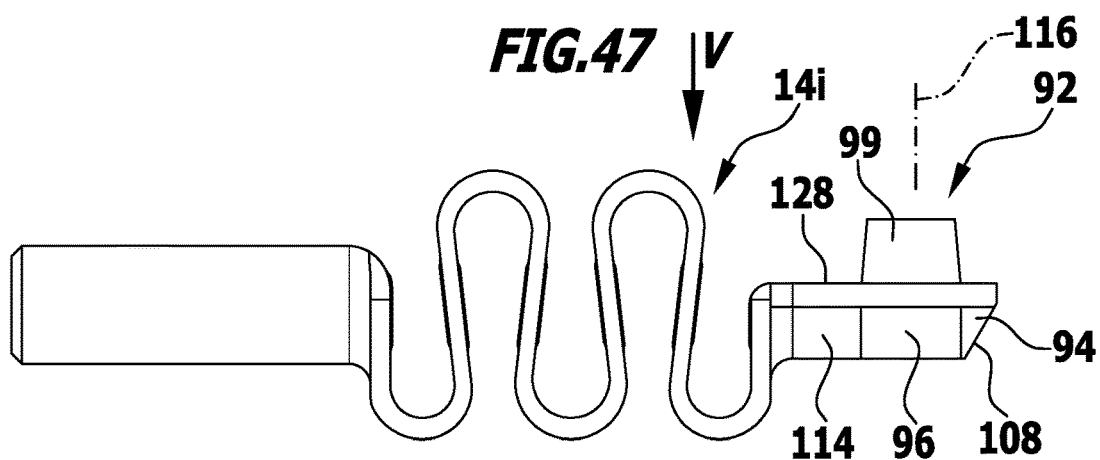
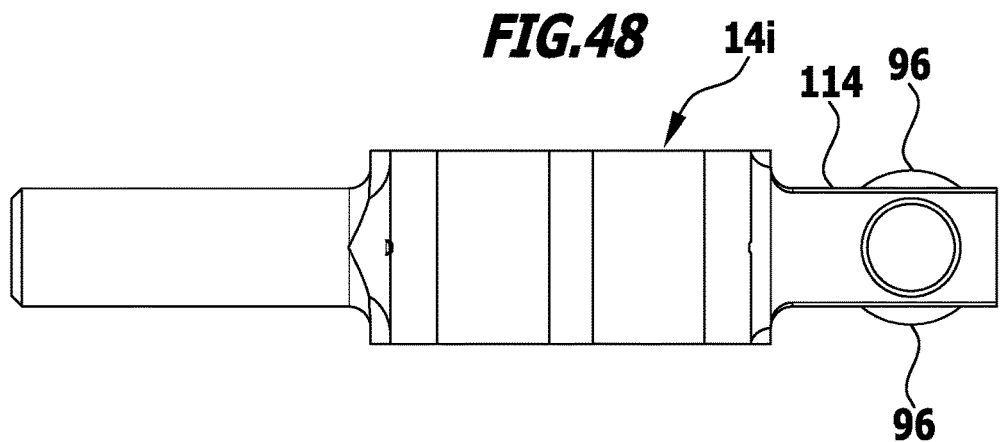

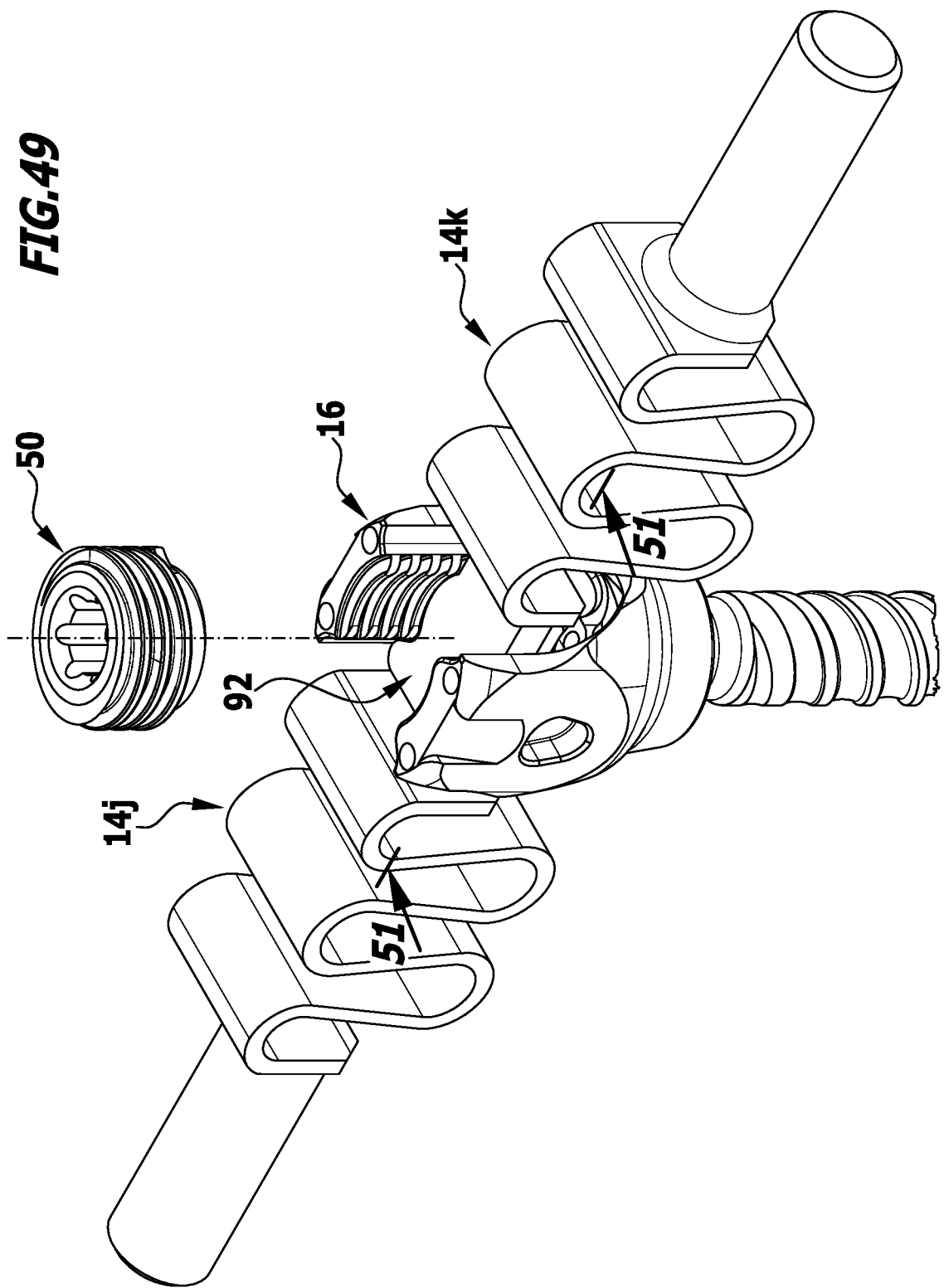

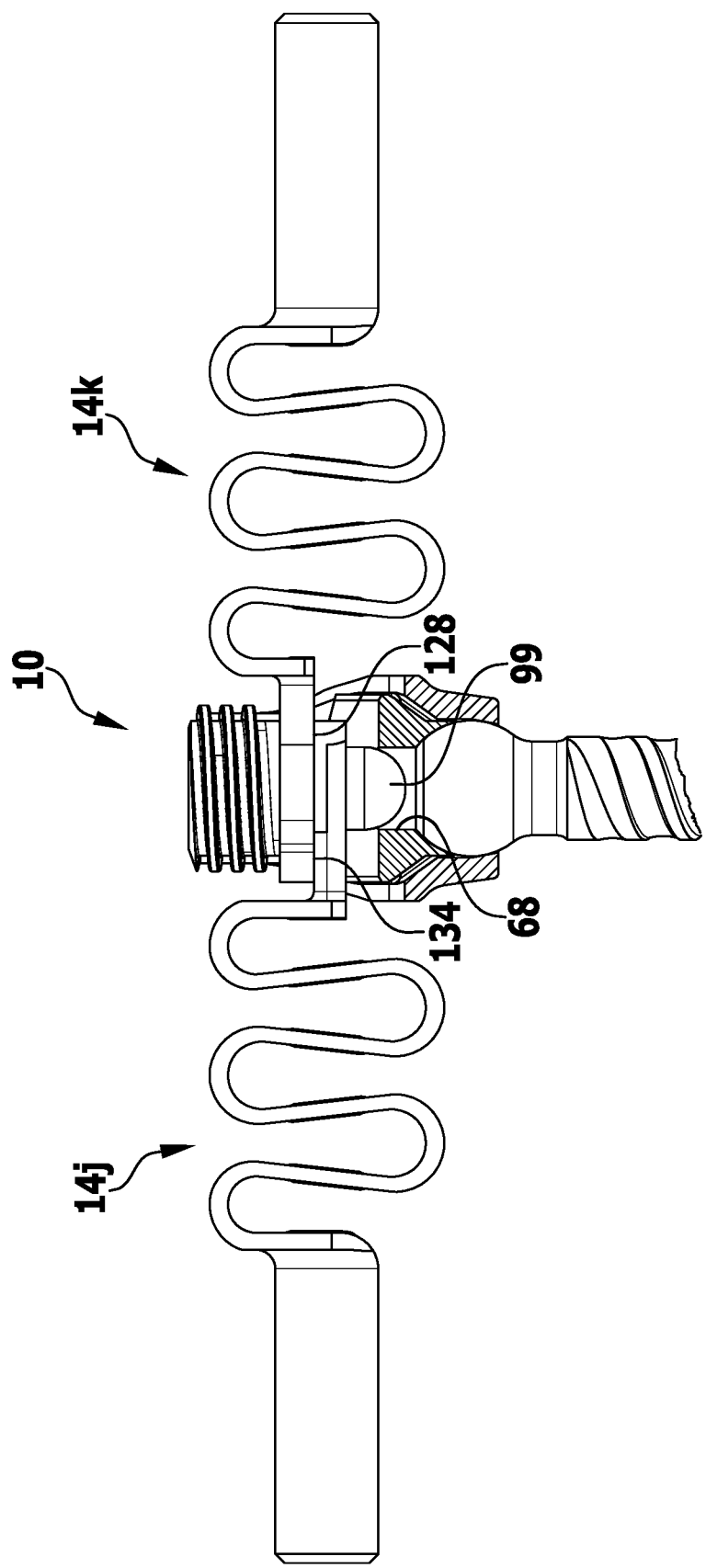

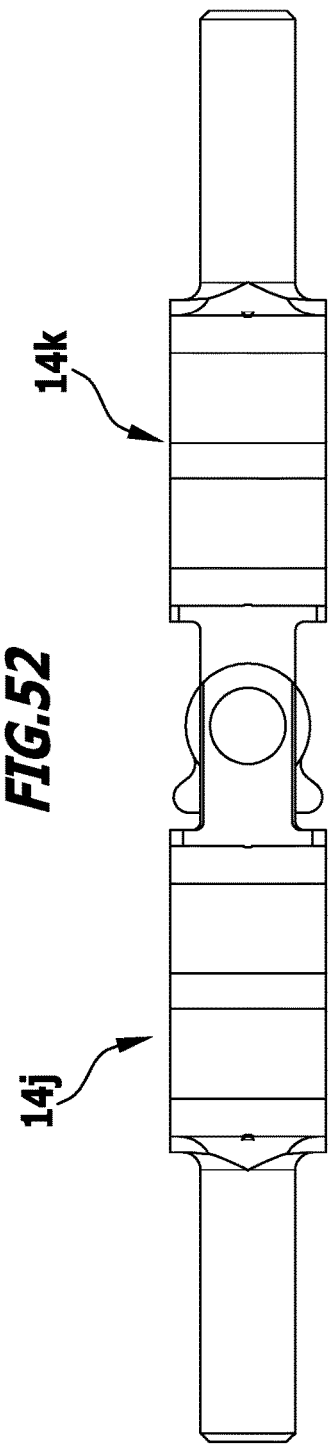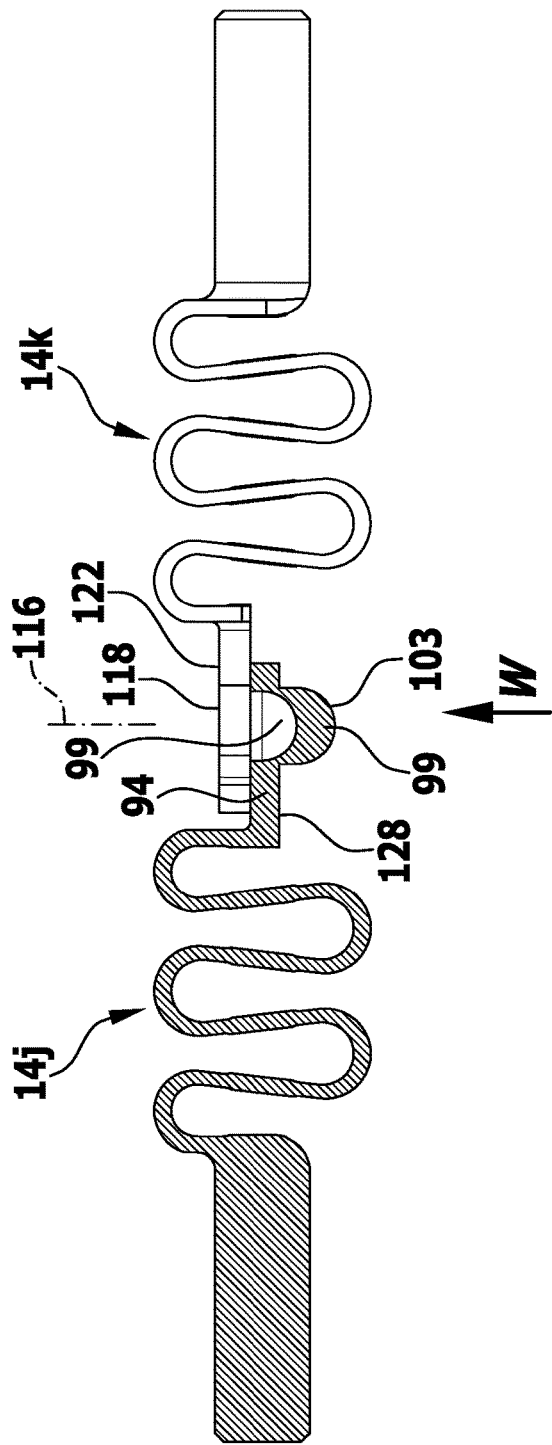

CONNECTION ELEMENT AND SPINE STABILIZATION SYSTEM

CROSS-REFERENCE TO RELATED APPLICATIONS

This application is a continuation of commonly-owned co-pending U.S. application Ser. No. 14/480,745 filed on Sep. 9, 2014, which claims the benefit of German patent application number 10 2013 110 173.9 filed on Sep. 16, 2013, each of which is incorporated by reference herein in its entirety and for all purposes.

FIELD OF THE INVENTION

The present invention relates to connection elements for spine stabilization systems generally, and more specifically to a connection element for a spine stabilization system with a first end for fixing to a first bone fixation device, a second end for fixing to a second bone fixation device and an intermediate portion arranged or formed between the two ends and defining a longitudinal axis.

The present invention further relates to spine stabilization systems generally, and more specifically to a spine stabilization system comprising at least one first bone fixation device, at least one second bone fixation device and at least one connection element, which at least one connection element comprises a first end for fixing to the at least one first bone fixation device, a second end for fixing to the at least one second bone fixation device and an intermediate portion arranged or formed between the two ends and defining a longitudinal axis.

BACKGROUND OF THE INVENTION

Connection elements and spine stabilization systems of the above-described type are known for example from EP 1 658 815 B1. The connection elements described in this European Patent comprise resilient elements and have first and second ends, which are each circular cylindrical in form and the longitudinal axes of which coincide. They may be fixed in clamped manner in corresponding bone fixation device receptacles.

A disadvantage of the known connection elements is, however, that the intermediate portion can only be oriented in a defined way with very considerable effort.

SUMMARY OF THE INVENTION

In a first aspect of the invention, a connection element for a spine stabilization system comprises a first end for fixing to a first bone fixation device, a second end for fixing to a second bone fixation device and an intermediate portion arranged or formed between the two ends and defining a longitudinal axis. At least one of the two ends takes the form of a coupling element for fixing the connection element to a bone fixation device in at least one defined orientation relative to the longitudinal axis. The coupling element has a shape other than a circular cylinder.

In a second aspect of the invention, a spine stabilization system comprises at least one first bone fixation device, at least one second bone fixation device and at least one connection element. Said at least one connection element comprises a first end for fixing to the at least one first bone fixation device, a second end for fixing to the at least one second bone fixation device and an intermediate portion arranged or formed between the two ends and defining a longitudinal axis. At least one of the two ends takes the form of a coupling element for fixing the connection element to a bone fixation device in at least one defined orientation relative to the longitudinal axis and wherein the coupling element has a shape other than a circular cylinder.

BRIEF DESCRIPTION OF THE DRAWINGS

The foregoing summary and the following description may be better understood in conjunction with the drawing figures, of which:

FIG. 7: is a side view of the connection element of FIG. 3;

FIG. 8: is a view of the connection element of FIG. 7 in the direction of arrow C;

FIG. 9: is a view of the connection element of FIG. 7 in the direction of arrow D;

FIG. 13: is a side view of the second exemplary embodiment of a connection element;

FIG. 14: is a view of the connection element of FIG. 13 in the direction of arrow G;

FIG. 15: is a view of the connection element of FIG. 13 in the direction of arrow H;

FIG. 18: is a side view of the connection element of FIG. 17;

FIG. 19: is a view of the connection element of FIG. 18 in the direction of arrow J;

FIG. 37: is a view of the connection element of FIG. 38 in the direction of arrow P;

FIG. 38: is a side view of the connection element of FIG. 35;

FIG. 43: is a view of the connection element of FIG. 44 in the direction of arrow T;

FIG. 44: is a side view of the connection element of FIG. 41;

FIG. 45: is a view of the connection element of FIG. 44 in the direction of arrow S;

FIG. 46: is a perspective view of a tenth exemplary embodiment of a connection element;

FIG. 47: is a view of the connection element of FIG. 46 in the direction of arrow U;

FIG. 48: is a view of the connection element of FIG. 47 in the direction of arrow V;

FIG. 49: is a schematic perspective view of an eleventh and a twelfth exemplary embodiment of a connection element in the process of being jointly fixed to a single bone screw;

FIG. 51: is a partially sectional view of the arrangement of FIG. 49 along line 51-51;

FIG. 52: is a view of the two connection elements of FIG. 53 in the direction of arrow W;

FIG. 53: is a partially sectional side view of the coupled-together connection elements of FIG. 49;

DETAILED DESCRIPTION

Figure 1:
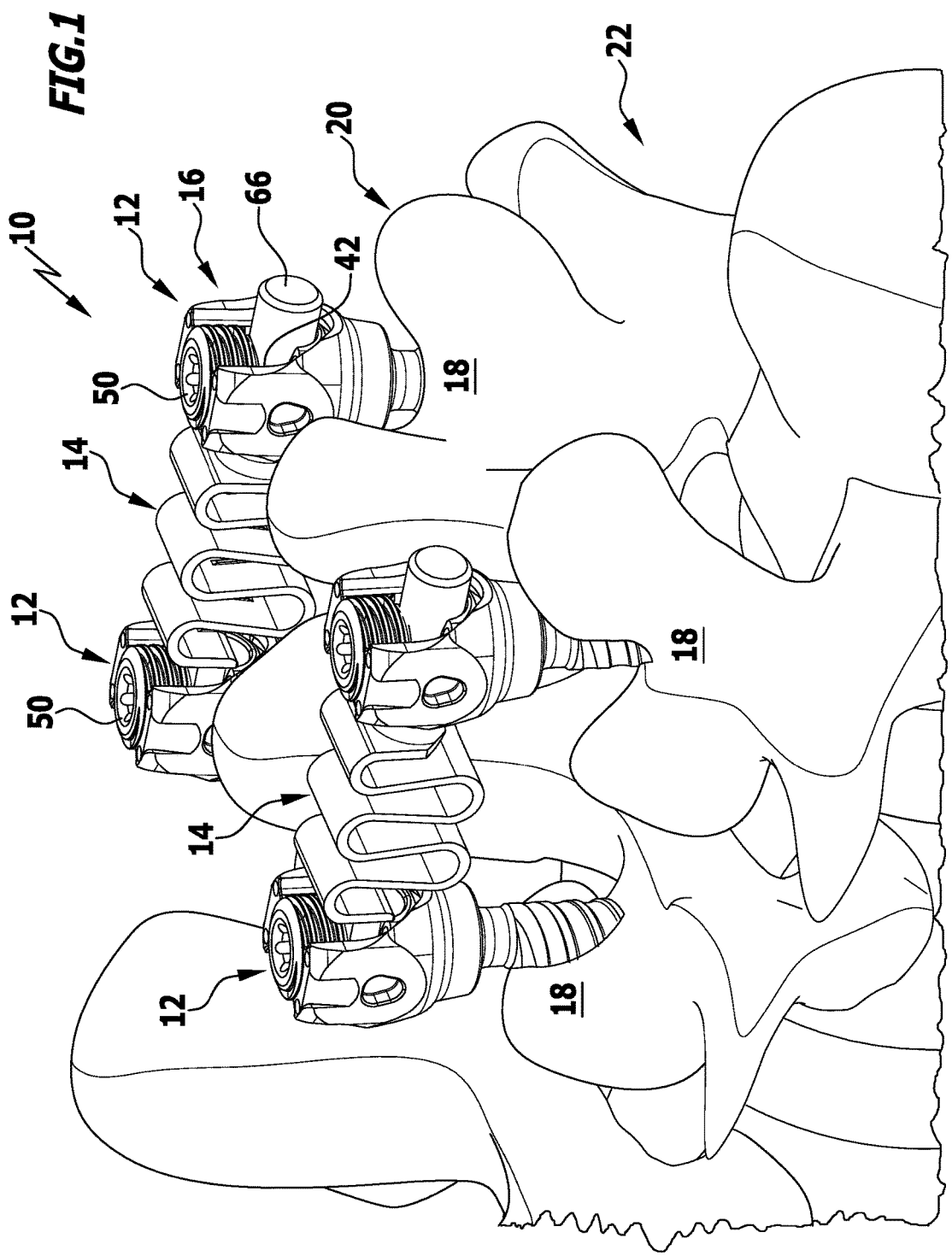
FIG. 1: is a schematic perspective overall view of a spine stabilization system fixed to a spinal column.
Figure 2:
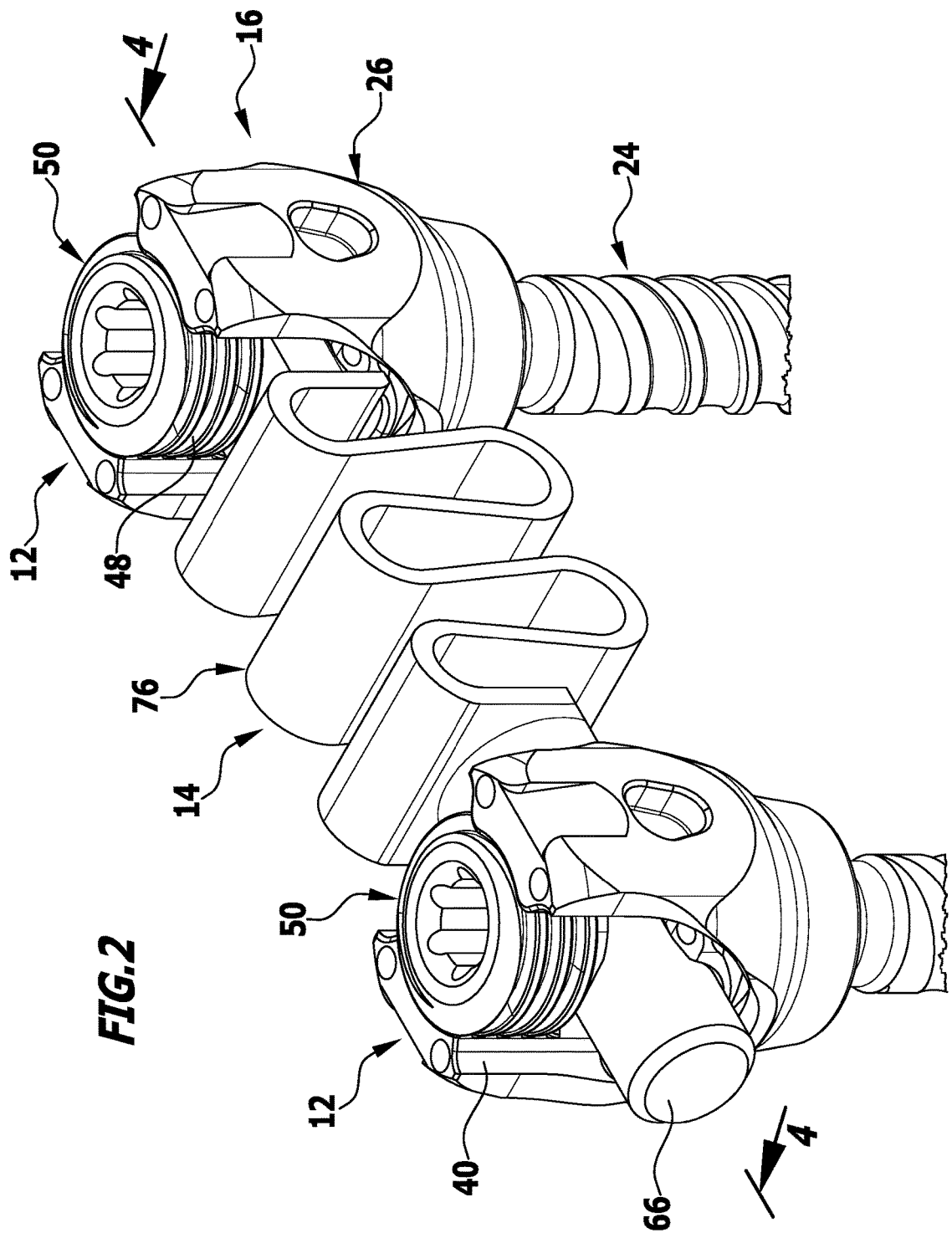
FIG. 2: is a view of a first exemplary embodiment of a connection element, fixed to two bone screws.
Figure 3:
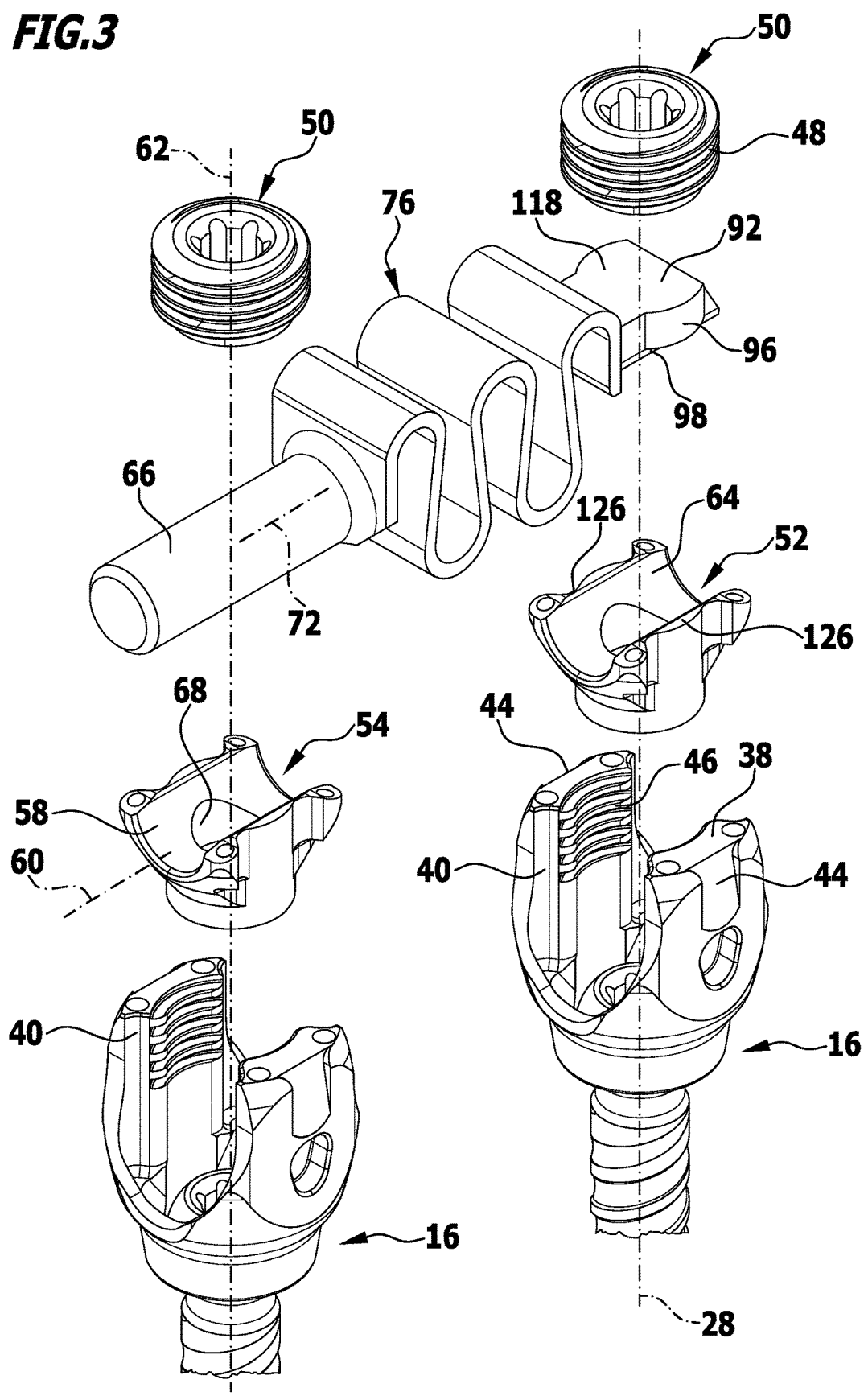
FIG. 3: is an exploded representation of the arrangement of FIG. 2.

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a connection element for a spine stabilization system with a first end for fixing to a first bone fixation device, a second end for fixing to a second bone fixation device and an intermediate portion arranged or formed between the two ends and defining a longitudinal axis, wherein at least one of the two ends takes the form of a coupling element for fixing the connection element to a bone fixation device in at least one defined orientation relative to the longitudinal axis and wherein the coupling element has a shape other than a circular cylinder.

This particular configuration makes it possible for an operator simply and reliably to implant the connection element with a defined orientation, i.e. in particular to fix it with a defined orientation to the bone fixation devices. Ends in the form of circular cylinders, as provided in the case of the connection elements known from EP 1 658 815 B1, do not define any preferential direction due to their rotationally symmetrical shape. Although they do allow any desired orientation of the connection element and thus orientation of the intermediate portion relative to the longitudinal axis thereof, this may actually be disadvantageous if, for example, the intermediate portion likewise defines a preferential direction, which is possible in particular in the case of flexible or partially flexible intermediate portions, and is therefore intended to be oriented in defined manner relative to the bone fixation devices. It is precisely this problem that is solved by the particular configuration of at least one of the two ends, or indeed of both ends, in the form of a coupling element having a shape other than a circular cylinder. In particular, the coupling element is configured by definition, unlike a circular cylinder, to be not fully rotationally symmetrical, such that even in the case of a connection element receptacle which is provided on a bone fixation device and may be configured to be rotationally symmetrical or substantially rotationally symmetrical, a defined orientation of the connection element and thus of the intermediate portion thereof relative to the longitudinal axis is possible, and that without an operator having to make particularly great efforts. Preferably, precisely one defined orientation is possible, due to a shaping of the coupling element.

The two ends are favourably configured in the form of a coupling element which has a shape other than a circular cylinder. In this way, an optimal connection with two bone fixation devices may be achieved.

The connection element may be simply produced if the coupling element is made in one piece. For example it may be formed by machining or produced by casting.

To improve the stability of the connection element, it is advantageous for it to be in one piece.

So that the connection element can be fixed simply and reliably to at least one bone fixation device with a defined orientation relative thereto, it is favourable for the coupling element to comprise a coupling element main body and at least one coupling member arranged or formed on the coupling element main body. The at least one coupling member may serve in particular to co-operate with a corresponding part on the bone fixation device or indeed with a further coupling member on a further connection element, for example to be able in this way to lengthen the connection element if required. In particular, the at least one coupling member may be configured to be brought into positive engagement with correspondingly provided further coupling members on other connection elements or on a bone fixation device.

Preferably, the at least one coupling member extends in a coupling member direction which extends parallel to or transversely of the longitudinal axis. Depending on how in particular a connection element receptacle is configured on a bone fixation device, an optimal connection with a bone fixation device can be achieved by corresponding predetermination of the coupling member direction, in particular rotation or axial displacement relative to the bone fixation device may in this way be simply and reliably prevented.

The connection element may be simply constructed if the coupling element main body is given the form of a straight or oblique general cylinder and if a cylinder longitudinal axis defined by the cylinder extends transversely of the longitudinal axis. A general cylinder has the same cross-sectional area in mutually parallel section planes. The cross-sectional area may have any desired shape but deviates according to the invention from a circle in order to avoid undefined orientation of the intermediate portion relative to the bone fixation devices. Alternatively, a cylinder longitudinal axis of the general cylinder may also extend parallel to the longitudinal axis of the connection element.

It is favourable for the coupling element main body to have a cross-sectional area which is circular, quadrangular or in the form of a multiple lobe member. In particular, the cross-sectional area may be rectangular or square. Such basic shapes are simple to produce and allow a defined orientation of the connection element relative to a bone fixation device.

Advantageously the at least one coupling member takes the form of a coupling projection or a coupling receptacle. It may thus co-operate in desired manner with corresponding recesses and projections.

Preferably the coupling projection is crowned, spherical, cylindrical, conical, cuboidal or takes the form of a combination of one or more of these shapes. In particular, the coupling projection may be conformed to a connection element receptacle of a bone fixation device, so as in particular to allow interlocking engagement.

According to a further preferred embodiment of the invention, provision may be made for the coupling receptacle to be hollow-crowned, hollow-spherical, hollow-cylindrical, cuboidal, in the form of a through opening in the coupling element main body or in the form of a combination of one or more of these shapes. In particular, a coupling receptacle shaped in this way may co-operate with a correspondingly shaped coupling projection of a further connection element, in order for example in this way to couple two ends of two connection elements together and fix them jointly to a bone fixation device.

The coupling receptacle may favourably take the form of a set-back portion or a groove. These may extend parallel to or transversely of the longitudinal axis.

It is advantageous for the coupling receptacle to be open in a direction transversely of and/or parallel to the longitudinal axis. Thus, it may, in cooperation with a further coupling member, prevent relative motion of the connection element relative to a bone fixation device parallel to and/or transversely of the longitudinal axis.

The connection element favourably has two, three or more coupling members. It is also possible for there to be in particular four, five or six coupling members. In particular, the coupling members have coupling member longitudinal axes oriented in different directions, in order in this way to limit movement of the connection element relative to a bone fixation device or a further connection element in different directions.

The connection element may be simply constructed if the coupling element has two coupling members arranged or formed in mirror-symmetrical manner relative to a mirror plane containing the longitudinal axis. These may for example be set-back portions or grooves extending parallel to one another.

It may moreover be favourable for the coupling element to be mirror-symmetrical relative to a mirror plane containing the longitudinal axis. It is thus possible, depending on the shape of the coupling element, to predetermine for example one, two or four defined orientations of the connection element relative to a bone fixation device.

The connection element may be particularly simply constructed if it is mirror-symmetrical relative to a mirror plane containing the longitudinal axis.

To fix the connection element in a particularly space-saving manner and optionally with a further connection element jointly in a connection element receptacle of a fixation device, it is advantageous for a centre of gravity of the coupling element to be spaced from the longitudinal axis.

Introduction of the connection element into the body of a patient, in particular in minimally invasive operations, may be improved and the risk of injury minimized if an end face of the coupling element facing away from the intermediate portion is inclined relative to the longitudinal axis or rounded.

Such an end face may be simply produced if an end face plane defined by the end face and the longitudinal axis form an end face angle of inclination which lies within a range of around 30° to 90°, preferably in a range of around 45° to 75°.

It is advantageous for the coupling element main body to include a portion of a circular cylinder, which has a circular cylinder axis extending transversely of the longitudinal axis. For example, the coupling element main body may engage in a corresponding recess in such a way that movement parallel to the longitudinal axis of the connection element relative to a bone fixation device or a further connection element may be simply and reliably limited.

It may furthermore be favourable for the coupling element main body to have a planar surface portion which defines a plane which extends parallel to or transversely of the longitudinal axis. In particular, a surface portion which defines a plane extending parallel to the longitudinal axis allows a flat contact for example with a fixing element for fixing the connection element to the bone fixation device. Furthermore, two ends of two connection elements may thus also abut flatly against one another.

According to a further preferred embodiment of the invention, provision may be made for the coupling element to comprise a connection element contact face for application against a further connection element. In particular, the connection element contact face may be configured to abut an end of the further connection element. Such a configuration enables particularly good and reliable coupling with a further connection element.

The connection element contact face preferably takes the form at least in part of a hollow-cylindrical wall surface. Such a configuration makes it possible in particular to receive an end of a further connection element in the form of a circular cylinder and extending in the direction of the longitudinal axis or parallel thereto.

It is favourable for the connection element contact face to take the form at least in part of a planar contact face portion. Such a connection element contact face is simple to produce and apply against a corresponding planar connection element contact face.

According to a further preferred embodiment of the invention, provision may be made for the coupling element main body to comprise two, three or more coupling element main body side faces which are planar or concavely curved away from the coupling element main body and inclined relative to one another. In particular, coupling element main body side faces inclined relative to one another, even if they are planar, may produce a concave shape facing away from the coupling element main body. Such a coupling element main body may in particular co-operate with a corresponding convex side face of a bone fixation device.

Production of the connection element may be further simplified if mutually adjacent planar coupling element main body side faces form an obtuse angle between them.

It is favourable for the intermediate portion to be a winding leaf spring element in the form of a strip and to comprise at least one recess open laterally in a recess direction transverse to a longitudinal axis defined by the intermediate portion. Such an intermediate portion makes it possible to set a defined resilience of the connection element and a defined anisotropy of the resilience in the circumferential direction relative to the longitudinal axis. Furthermore, the connection element with the recesses may be simply and reliably handled, for example with a correspondingly shaped holding instrument. In addition, blocking elements may also be temporarily inserted into the recesses, in order to limit the resilience of the connection element temporarily completely or in part, in particular during implantation.

According to a further preferred embodiment of the invention, provision may be made for the coupling element to define at least one preferential direction transverse to the longitudinal axis and for the preferential direction and the recess direction to form an orientation angle in a range from 0° to 180°. The orientation angle preferably lies in a range from 0° to 90°. As a result of this configuration of the coupling element, an orientation of the connection element may be specified relative to the longitudinal axis and thus also an orientation of the recess direction for example relative to the part of the bone fixation device on which the connection element receptacle is formed to receive one end of the connection element.

The coupling element preferably defines two or more preferential directions. This allows an operator to arrange the connection element in different but defined orientations relative to the bone fixation device.

It is advantageous for a preferential angle between two preferential directions of the coupling element to correspond to an angle 180°/n, wherein n is the number of preferential directions defined overall by the coupling member. If for example the coupling element defines two preferential directions, the preferential angle amounts in particular to 90°.

The connection element is advantageously made from a metallic material or a plastics material. The materials are preferably biocompatible and have the stability required for the application.

It is favourable for the metallic material to be or contain titanium, a titanium alloy or a cobalt-chromium alloy. Such materials are extremely suitable as implant materials.

It is moreover advantageous for the plastics material to be or contain polyetherether ketone or carbon fibre reinforced polyetherether ketone. Such a plastics material is likewise biocompatible and has the stability required for the application.

The present invention further relates to a spine stabilization system comprising at least one first bone fixation device, at least one second bone fixation device and at least one connection element, which at least one connection element comprises a first end for fixing to the at least one first bone fixation device, a second end for fixing to the at least one second bone fixation device and an intermediate portion arranged or formed between the two ends and defining a longitudinal axis, wherein at least one of the two ends takes the form of a coupling element for fixing the connection element to a bone fixation device in at least one defined orientation relative to the longitudinal axis and wherein the coupling element has a shape other than a circular cylinder.

Such spine stabilization systems having any one of the above-described connection elements then likewise have the advantages described herein.

It is favourable for the at least one first and/or the at least second bone fixation devices to take the form of pedicle screws. In particular, the pedicle screws may take the form of polyaxial pedicle screws. Pedicle screws are in particular designed to be fixed to the pedicles of vertebrae. If connection elements are fixed to the pedicle screws, the mobility of a patient's spinal column may be wholly or partially restricted in a defined manner.

It is moreover favourable for the at least one first and/or the at least one second bone fixation device to have a fixing part and a holding part and for the holding part to have a connection element receptacle for receiving at least one end of a connection element. The holding part may optionally be connected movably or immovably with the fixing part. The holding part is preferably fixable in an implantation position relative to the fixing part. This allows the holding part first of all to be oriented in the desired manner relative to the fixing part and then fixed, for example with simultaneous fixing of the connection element in the connection element receptacle.

A connection element receptacle may be formed in a particularly simple manner if the holding part has two wall portions arranged symmetrically to one another and laterally defining the connection element receptacle. Overall, a holding part which is fork-shaped may be formed in this way. It may also be stated that the connection element receptacle is formed by a slot in the holding part.

It is favourable for the at least one first and/or the at least one second bone fixation device to comprise a fixing screw with an external thread and for the connection element receptacle to comprise an internal thread corresponding to the external thread. The fixing screw allows simple fixing of an end of a connection element inserted into the connection element receptacle temporarily or permanently to the first or second bone fixation device.

It is moreover advantageous for the coupling element main body to have a planar clamping surface portion for a distal end of the fixing screw, which clamping surface portion defines a plane extending parallel or substantially parallel to the longitudinal axis. It is thus in particular possible to clamp the clamping surface portion flatly with a distal end of the fixing screw.

The intermediate portion is preferably at least partially flexible. With such an intermediate portion a defined mobility of the spine stabilization system may be preset. It is favourable for the intermediate portion to predetermine an anisotropic flexibility. In this way, for example, flexion and extension in a patient's median plane may be partially enabled, but not sideways bending of the spinal column.

According to a further preferred embodiment of the invention, provision may be made for the spine stabilization system to comprise two connection elements, which have mutually corresponding coupling elements which may be fixed jointly in a connection element receptacle of the at least one first and/or the at least one second bone fixation device. This allows a particularly compact structure of the spine stabilization system to be achieved. In particular, connection elements may in this way be simply extended.

In particular, it is also possible to use only short connection elements, which are of a length which specifically allows connection between two bone fixation devices. It is for example moreover possible, with a single fixing screw, to fix not only one connection element in clamped manner to the bone fixation device, but also two connection elements to a single bone fixation device.

It is advantageous for the coupling elements of the two connection elements to have mutually corresponding coupling members, which, in a coupling position in which the two coupling elements are held jointly in a connection element receptacle of the at least one first and/or of the at least one second bone fixation device, co-operate in force- and/or positive-locking manner or are in engagement with one another. The coupling members allow direct, in particular a positive-locking coupling between the two connection elements, and not just between the connection elements and bone fixation device.

FIG. 1 is a schematic representation of a spine stabilization system 10 comprising a total of four bone fixation devices 12 and two connection elements 14. The bone fixation devices 12 take the form of bone screws 16. FIGS. 1 to 6 show "polyaxial" bone screws 16, by way of example.

The bone screws 16 are screwed into the pedicles 18 of vertebrae 20 of a spinal column 22. For stabilization thereof, in each case one bone screw 16 is screwed for example into pedicles 18 of adjacent vertebrae 20, said bone screws then being coupled together via a connection element 14.

The polyaxial bone screws 16 comprise a fixing part 24 and a holding part 26. The fixing part 24 comprises a shank defining a longitudinal axis 28 and having an external thread 32 for screwing into bone. A proximal end of the shank 30 takes the form of a spherical head 34, on which the holding part 26 is movably mounted. The holding part 26 is substantially in the form of a sleeve and has a hollow-spherical seat 36 on the distal side for the head 34, such that the holding part 26 is pivotable in a mounted position about a centre point of the head 34 relative to the fixing part 24. Starting from its proximal end 38, the holding part 26 comprises two notches 40 diametrically opposite one another relative to the longitudinal axis 28, so as to form two wall portions 44 arranged symmetrically relative to one another and relative to the longitudinal axis 28 and laterally defining a connection element receptacle 42. Starting from the end 38, an internal thread 46 is formed on the holding part 26 in the region of the wall portions 44, which internal thread corresponds to an external thread 48 on a fixing screw 50.

In addition, the holding part 26 comprises a clamping member 52 in the form of an insert 54. This has a hollow dome-shaped distal end 56, which may be brought into contact with the head 34. A proximal end substantially takes the form of a half cylinder sleeve 58, the cylinder sleeve longitudinal axis 60 of which extends transversely of a holding part longitudinal axis 62. The cylinder sleeve 58 defines a hollow-cylindrical contact surface 64 for in particular a first end 66, in the form of a cylindrical rod, of the connection element 14.

In addition, the insert 54 has a through opening extending coaxially to the holding part longitudinal axis 62 in the form of a bore 68.

Figure 4:
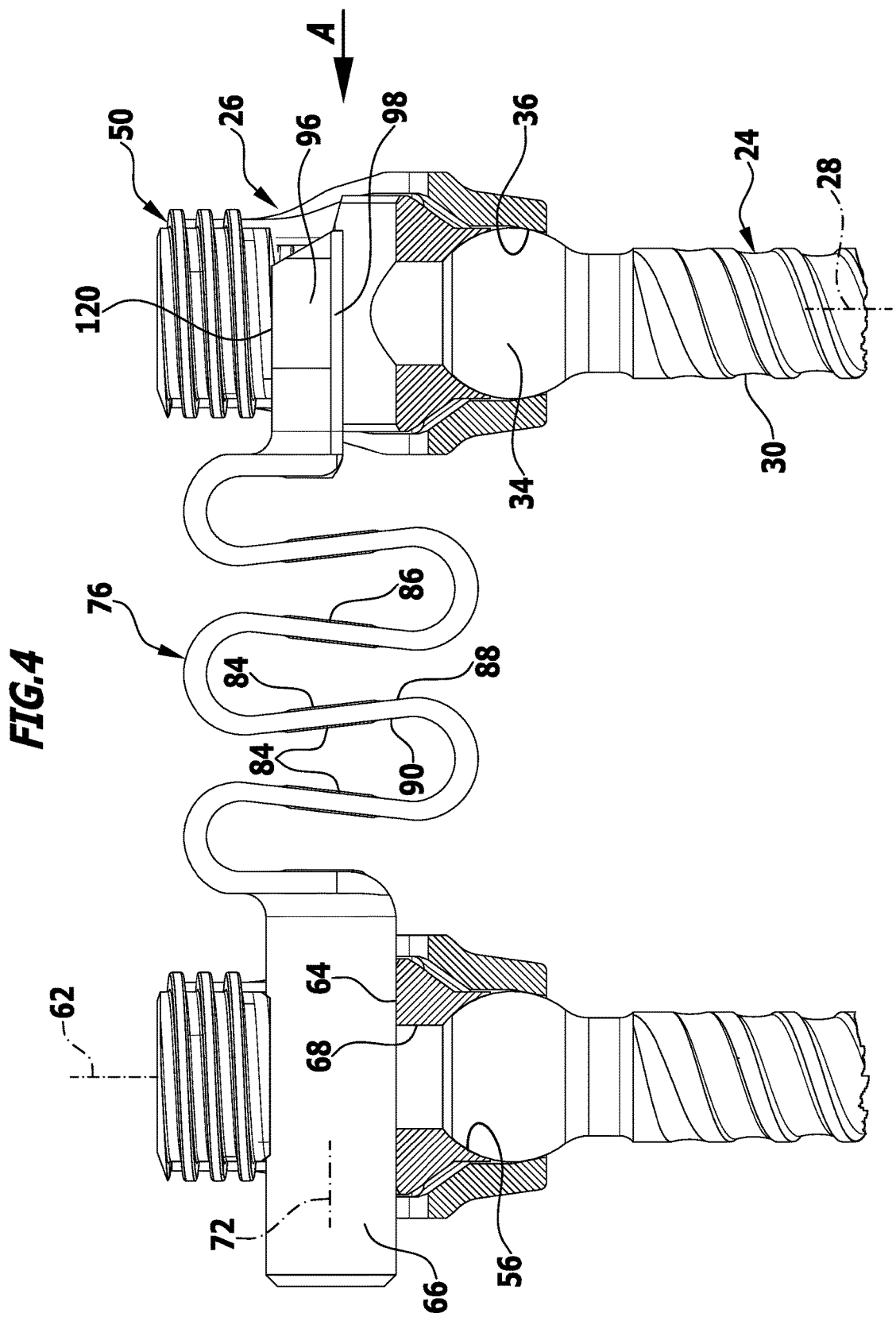
FIG. 4: is partially sectional view of the arrangement in FIG. 2 along line 4-4.
Figure 5:
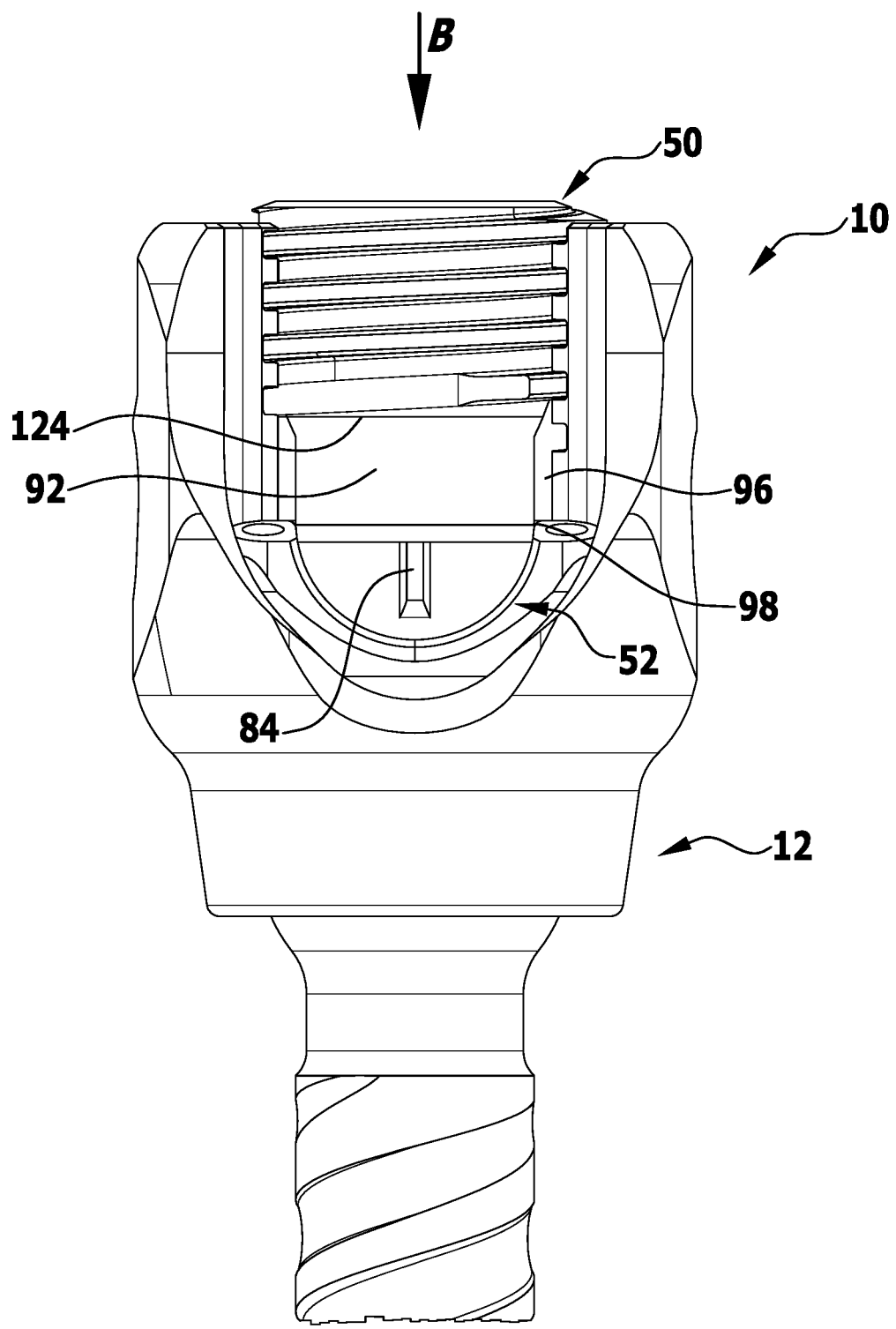
FIG. 5: is a view in the direction of arrow A in FIG. 4.
Figure 6:
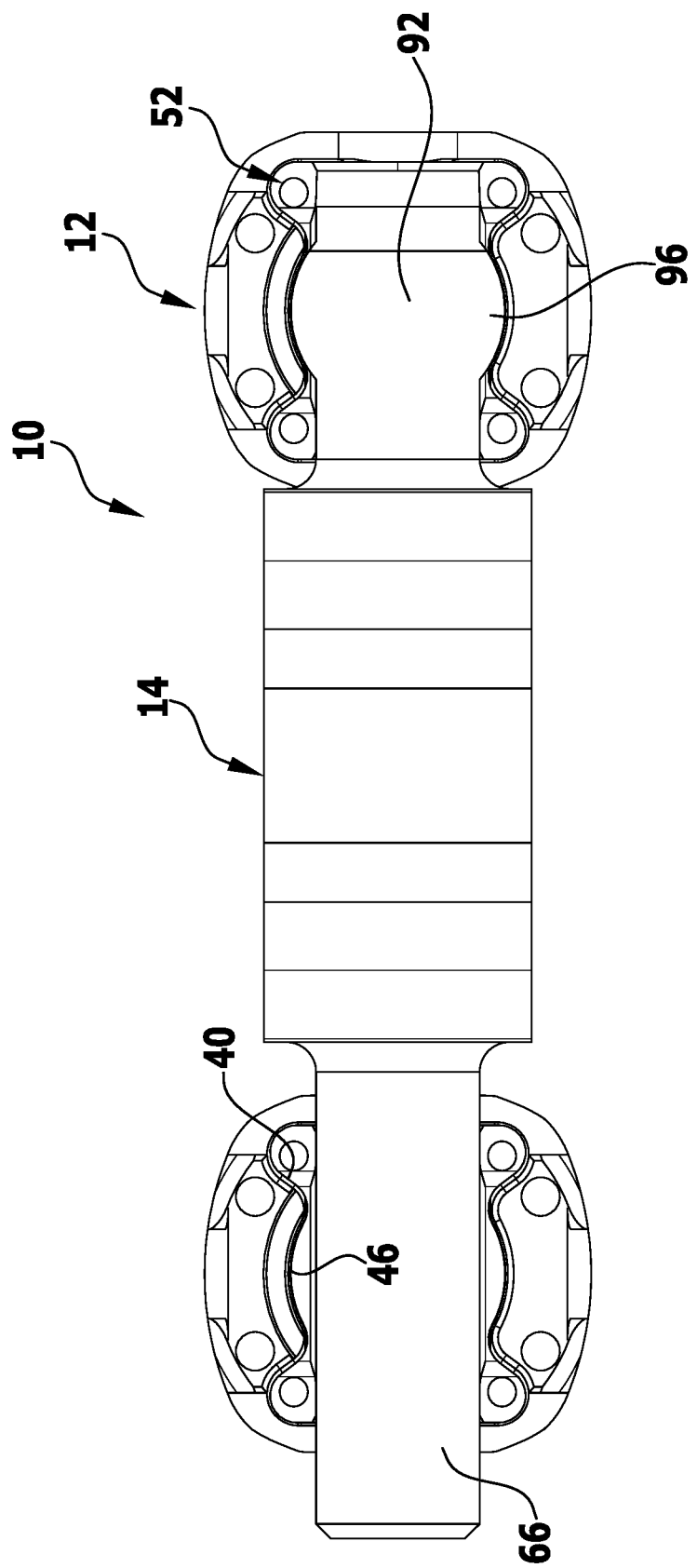
FIG. 6: is a view in the direction of arrow B in FIG. 5.
Figure 10:
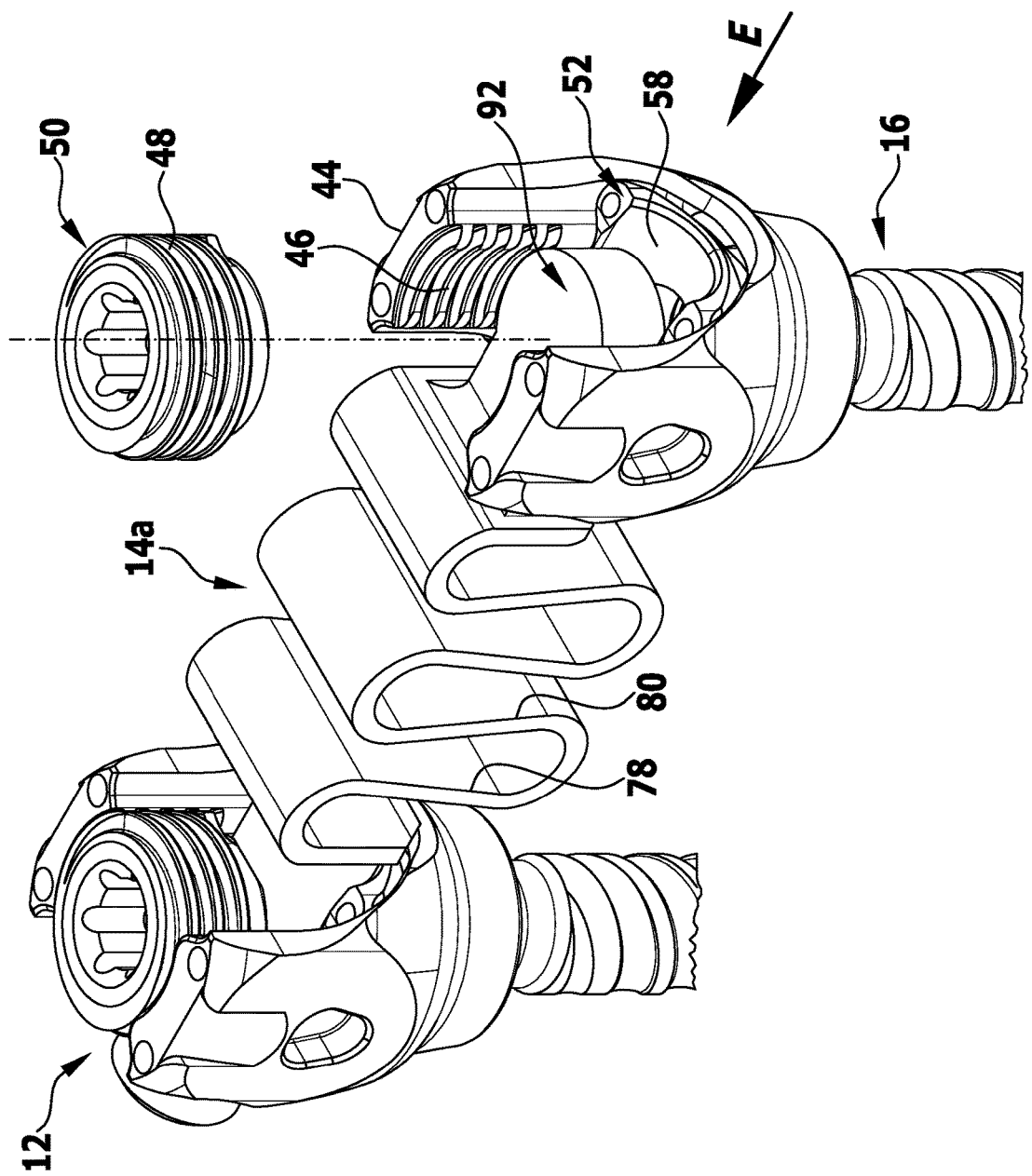
FIG. 10: is a schematic perspective view of a second exemplary embodiment of a connection element in the process of being fixed to two bone screws.
Figure 11:
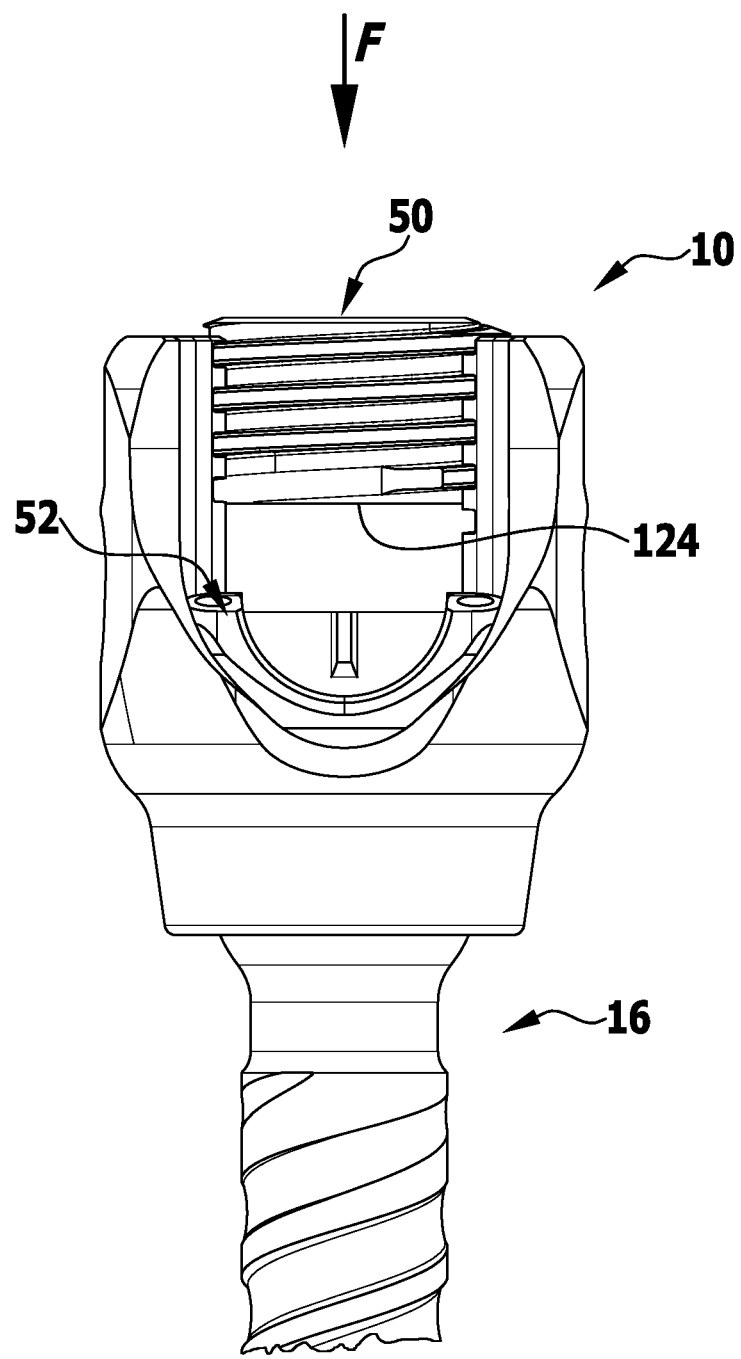
FIG. 11: is a view of the arrangement of FIG. 10 in the direction of arrow E.
Figure 12:
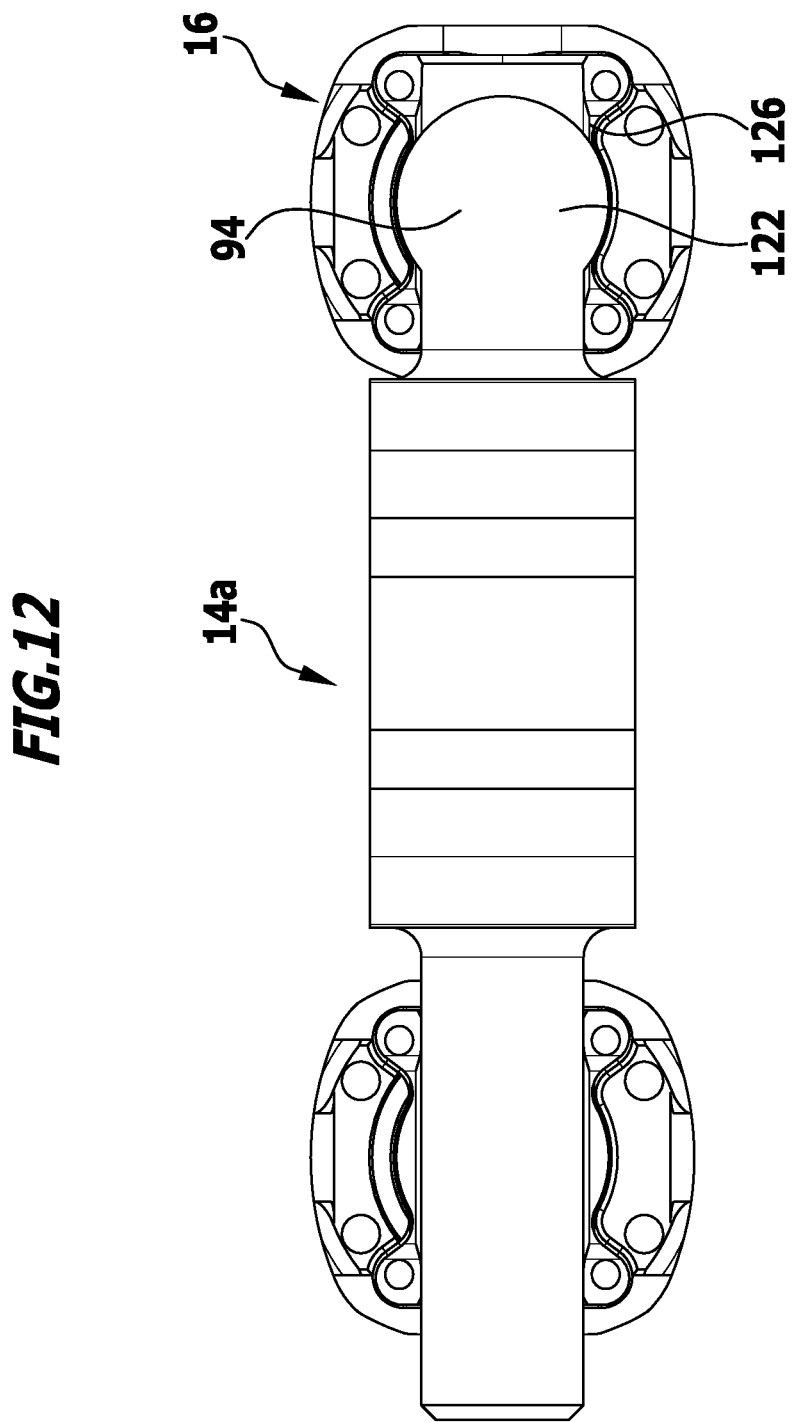
FIG. 12: is a view of the arrangement of FIG. 11 in the direction of arrow F.
Figure 16:
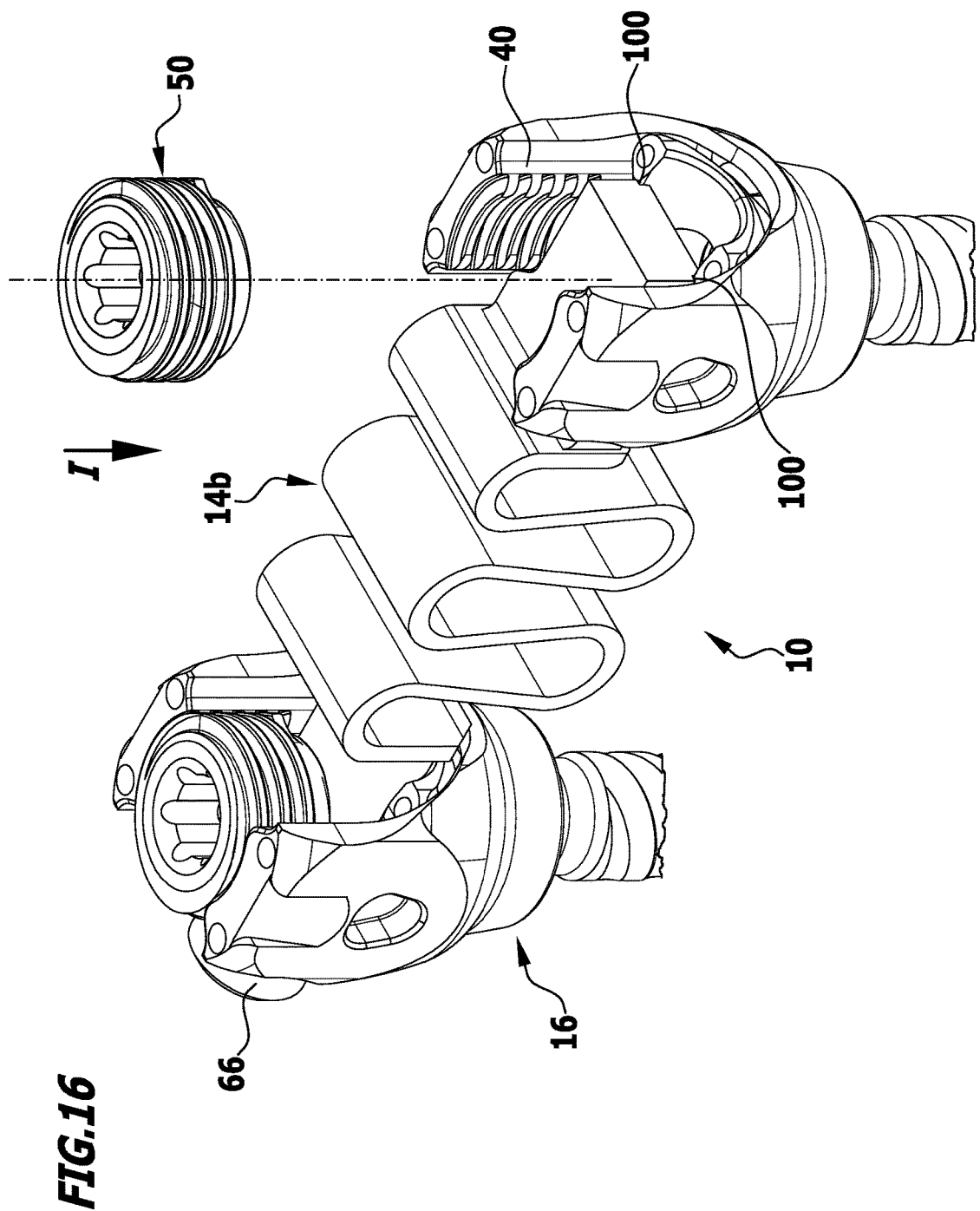
FIG. 16: is a schematic perspective view of a third exemplary embodiment of a connection element in the process of being fixed to two bone screws.
Figure 17:
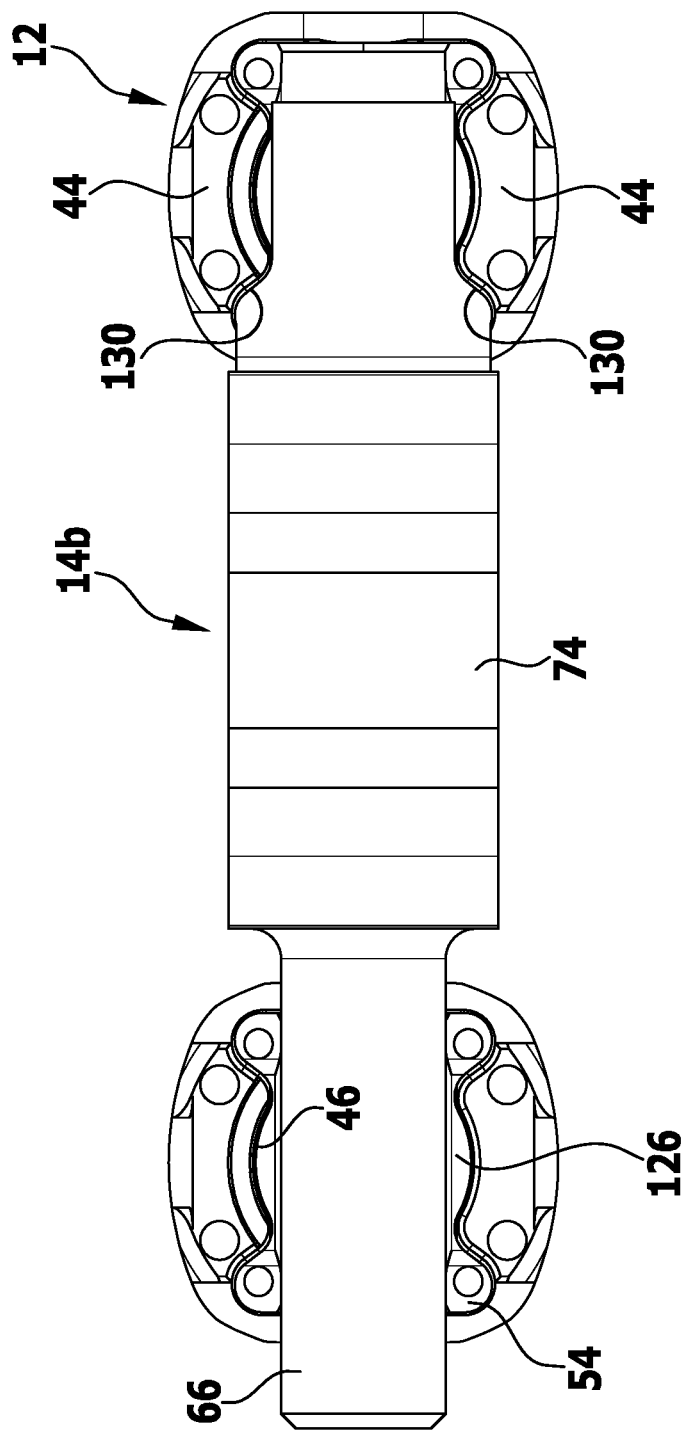
FIG. 17: is a view of the arrangement of FIG. 16 in the direction of arrow I.
Figure 20:
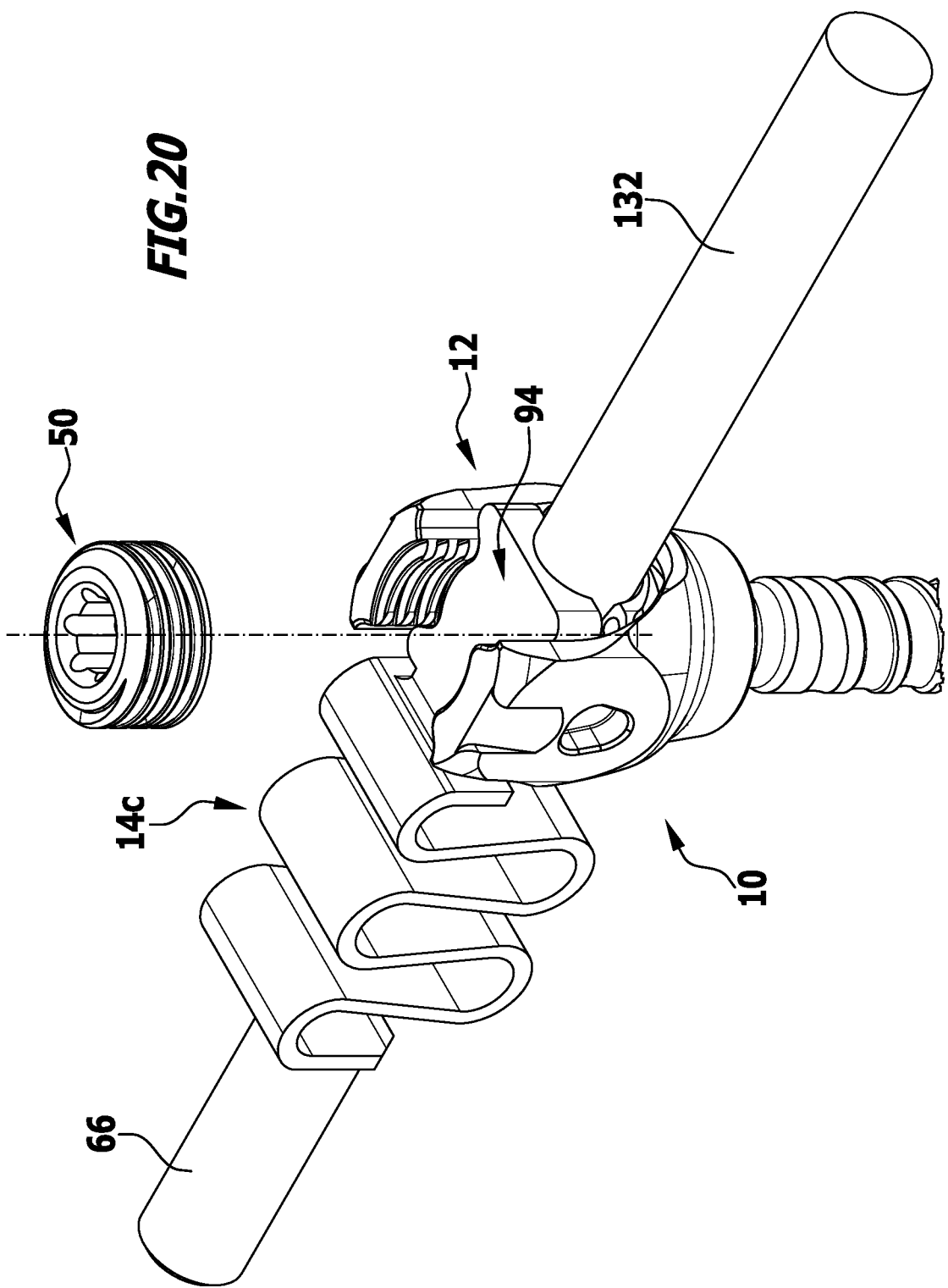
FIG. 20: is a schematic perspective view of a fourth exemplary embodiment of a connection element in the process of being fixed to a bone screw with a further rod-shaped connection element.
Figure 21:
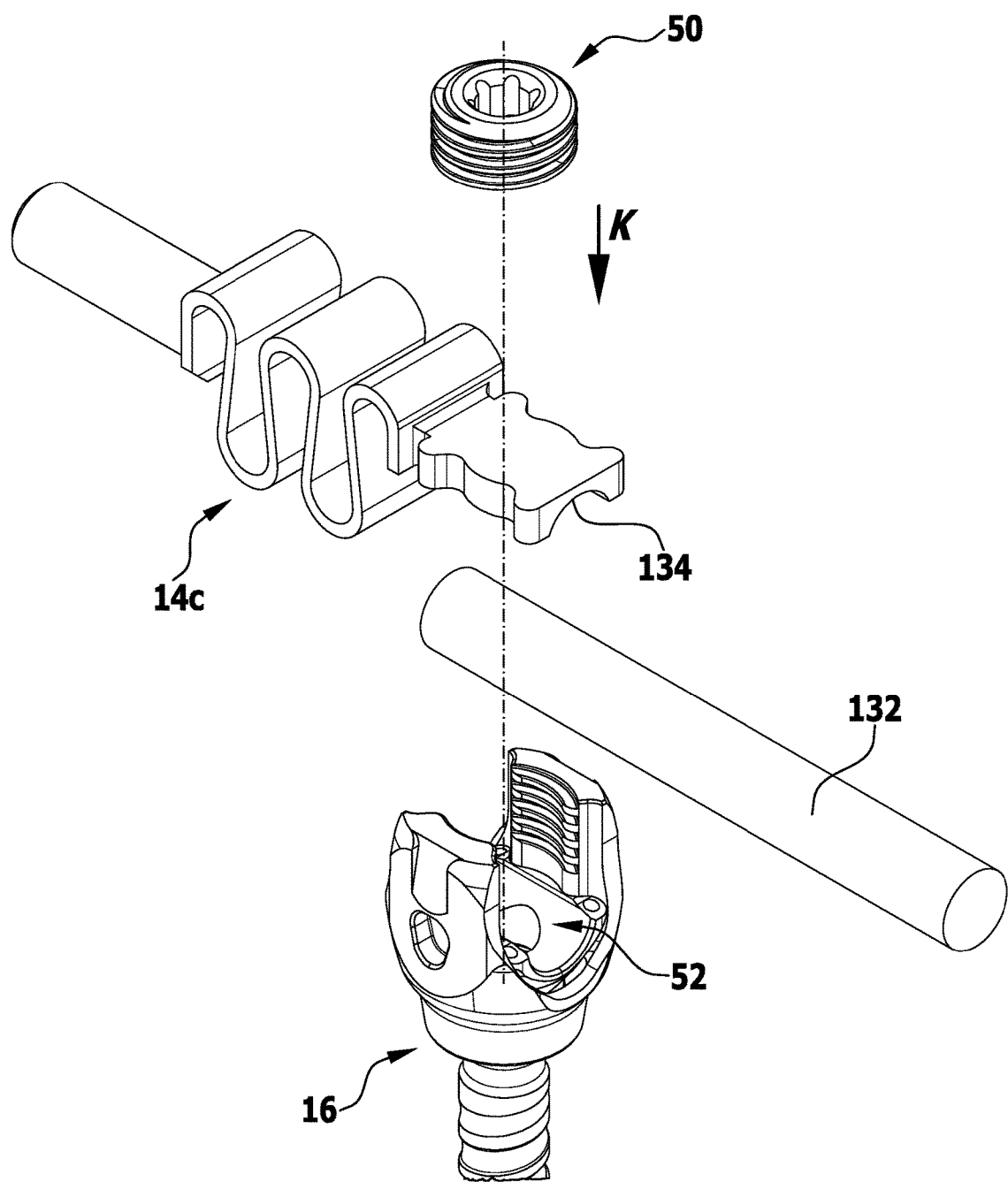
FIG. 21: is an exploded representation of the arrangement of FIG. 20.
Figure 22:
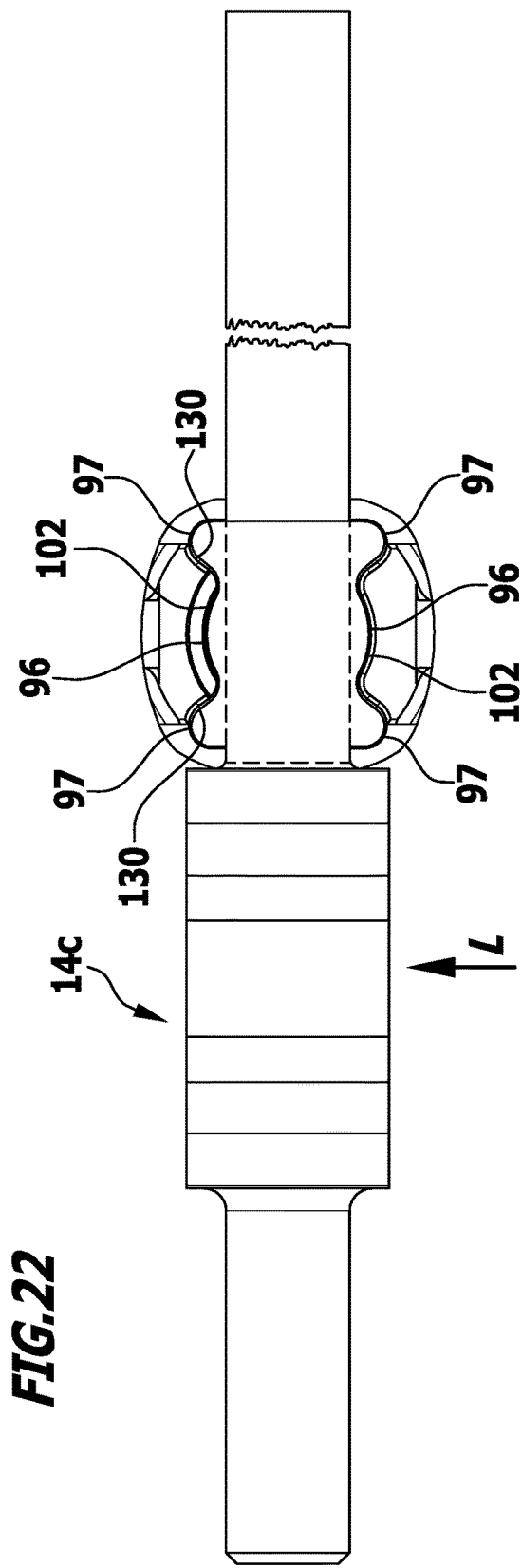
FIG. 22: is a view of the arrangement of FIG. 21 in the direction of arrow K.
Figure 23:
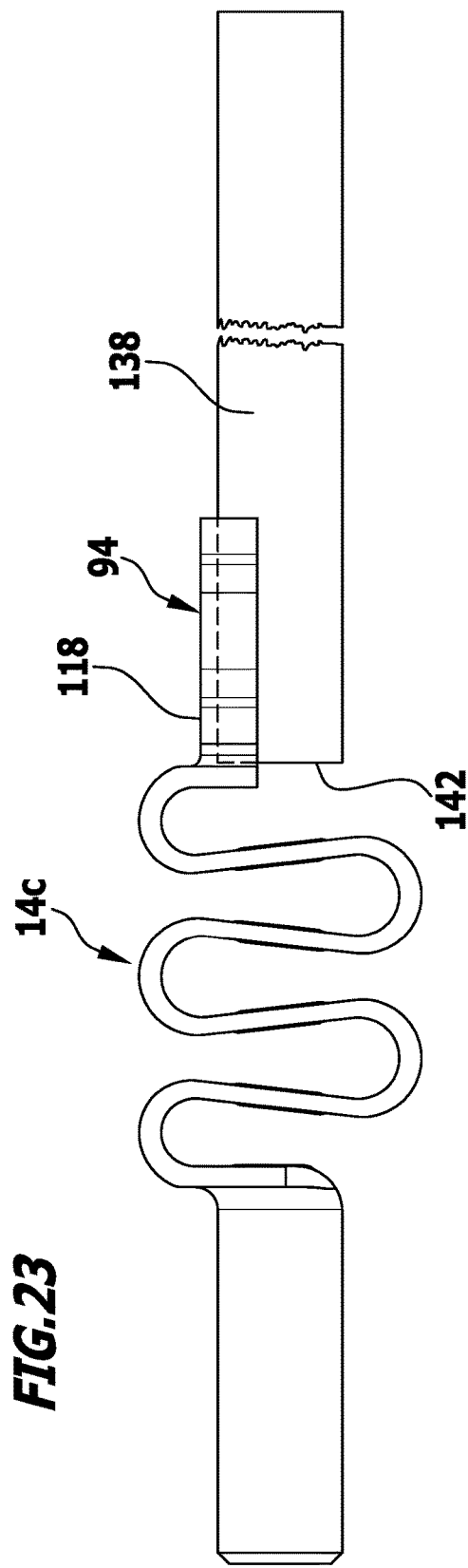
FIG. 23: is a view of the two connection elements in FIG. 22 in the direction of arrow L.
Figure 24:
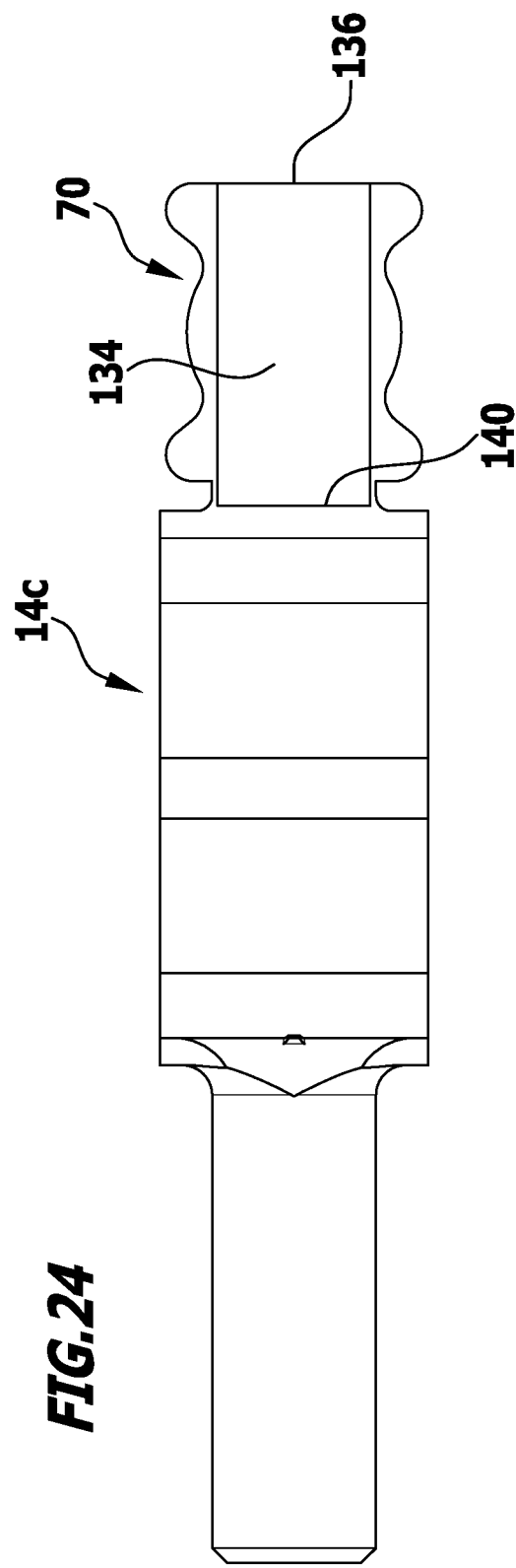
FIG. 24: is a view of the connection element of FIG. 25 in the direction of arrow M.
Figure 25:
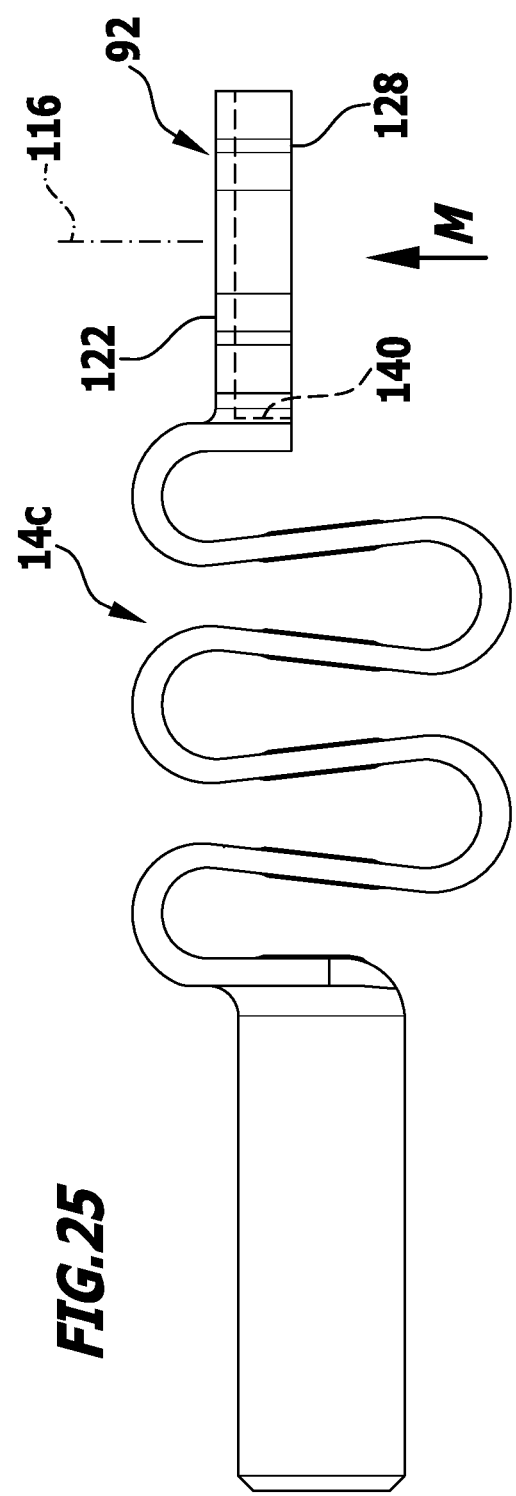
FIG. 25: is a side view of the connection element of FIG. 23.
Figure 26:
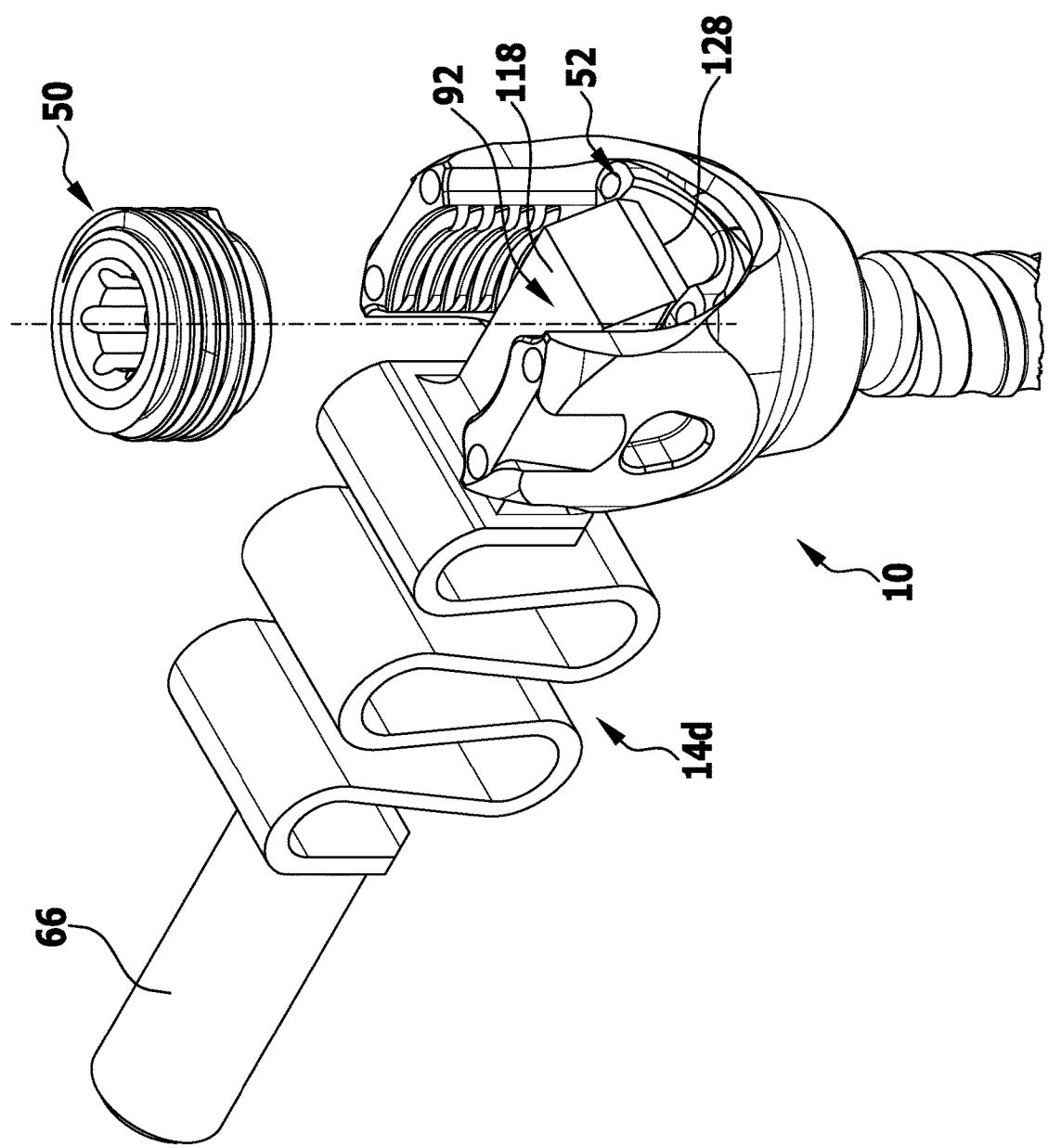
FIG. 26: is a schematic perspective view of a fifth exemplary embodiment of a connection element in the process of being fixed to a bone screw.
Figure 27:
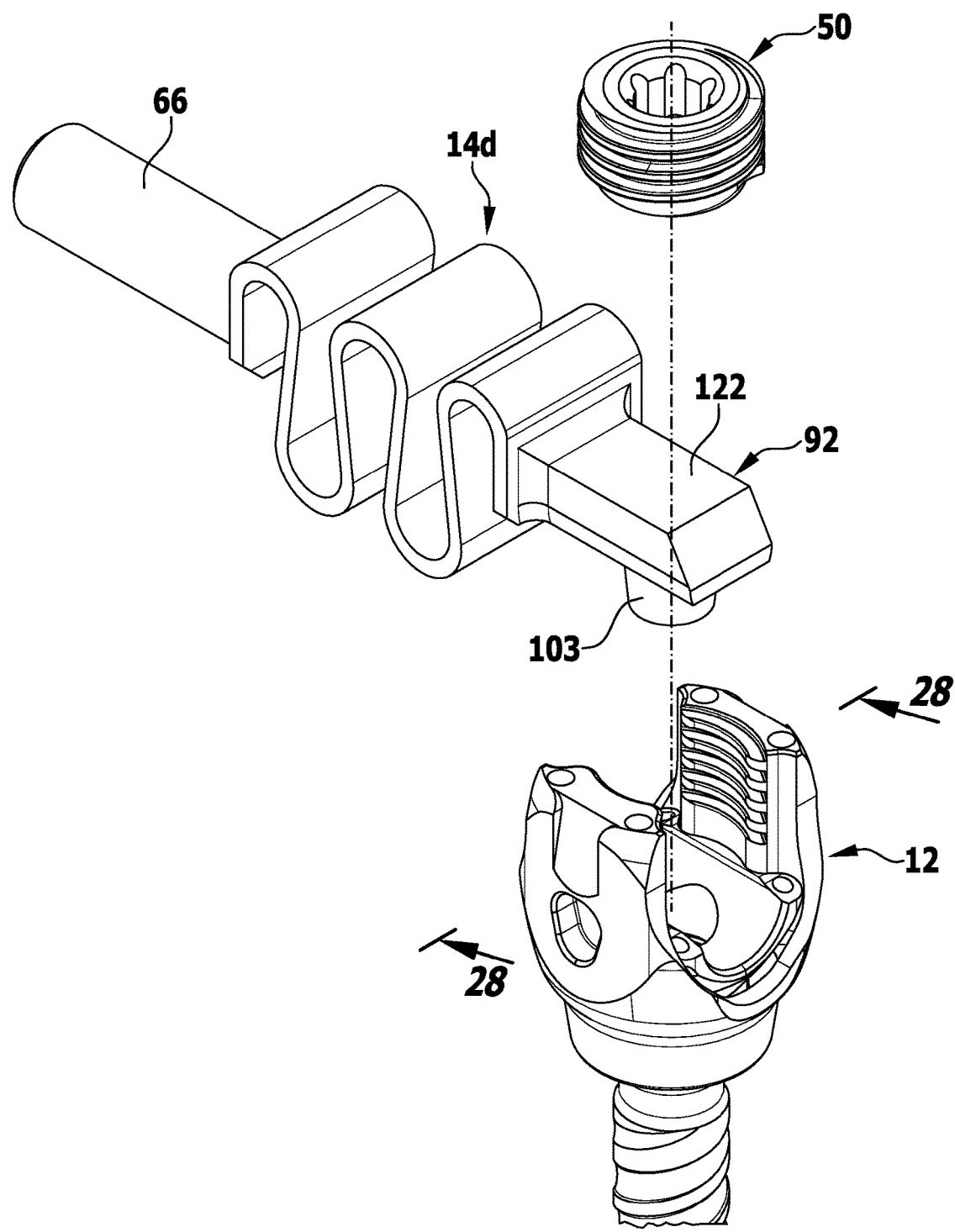
FIG. 27: is an exploded representation of the arrangement of FIG. 26.
Figure 28:
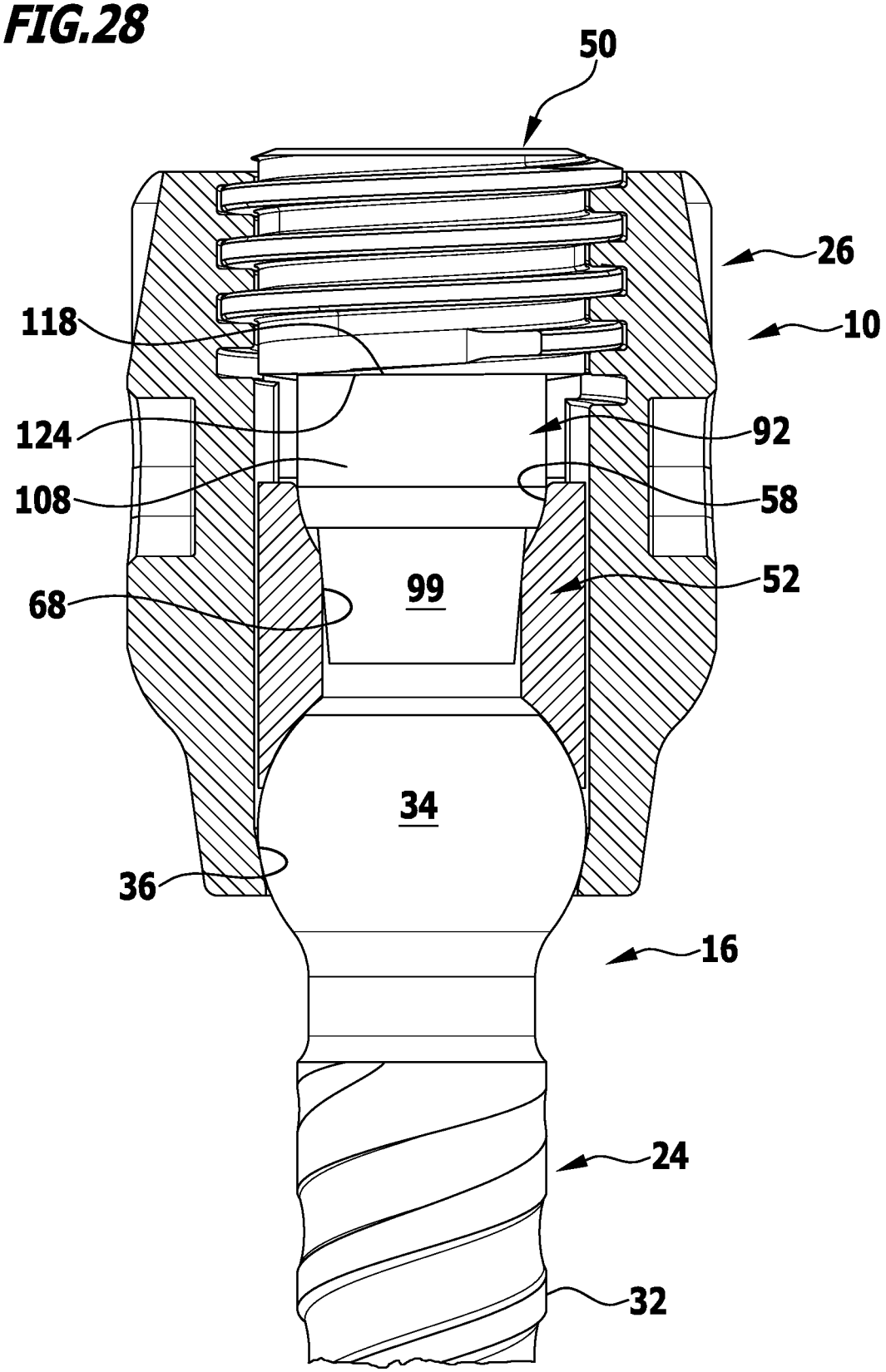
FIG. 28: is a partially sectional view of the arrangement of FIG. 27 along line 28-28.
Figure 29:
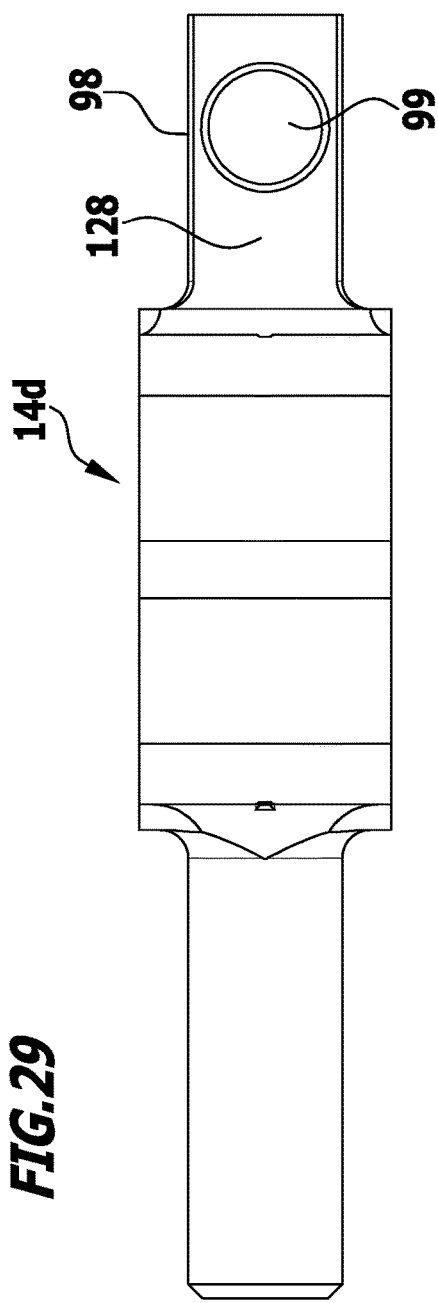
FIG. 29: is a view of the connection element of FIG. 30 in the direction of arrow N.
Figure 30:
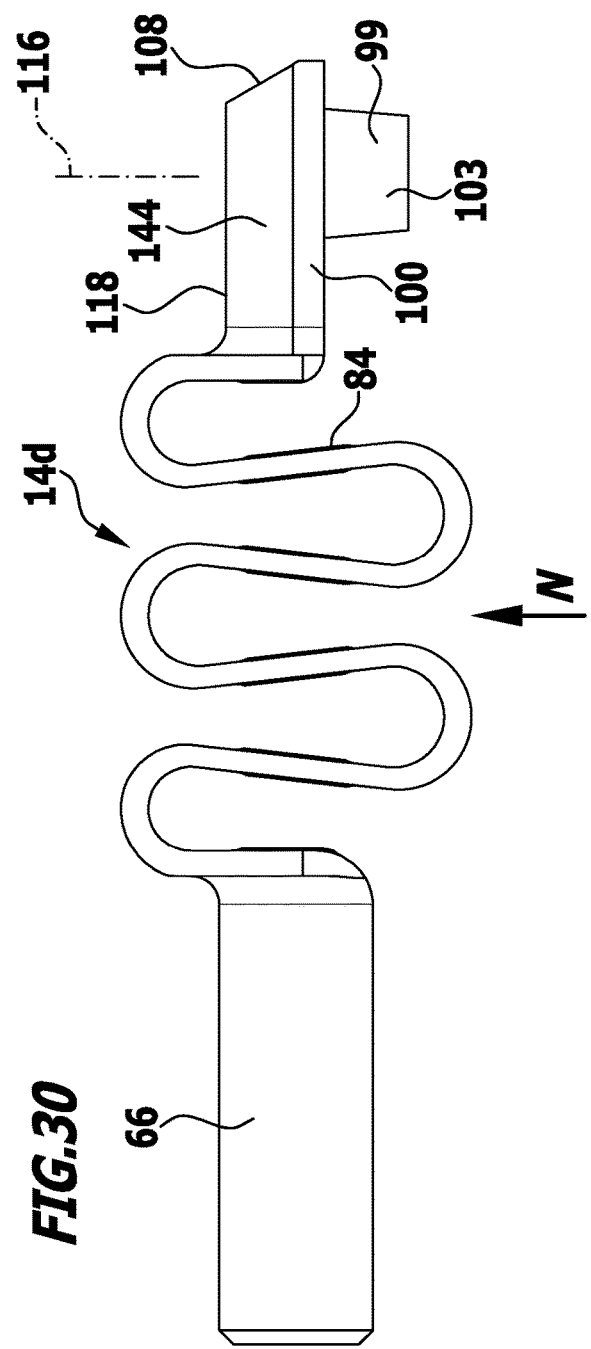
FIG. 30: is a side view of the connection element of FIG. 27.
Figure 31:
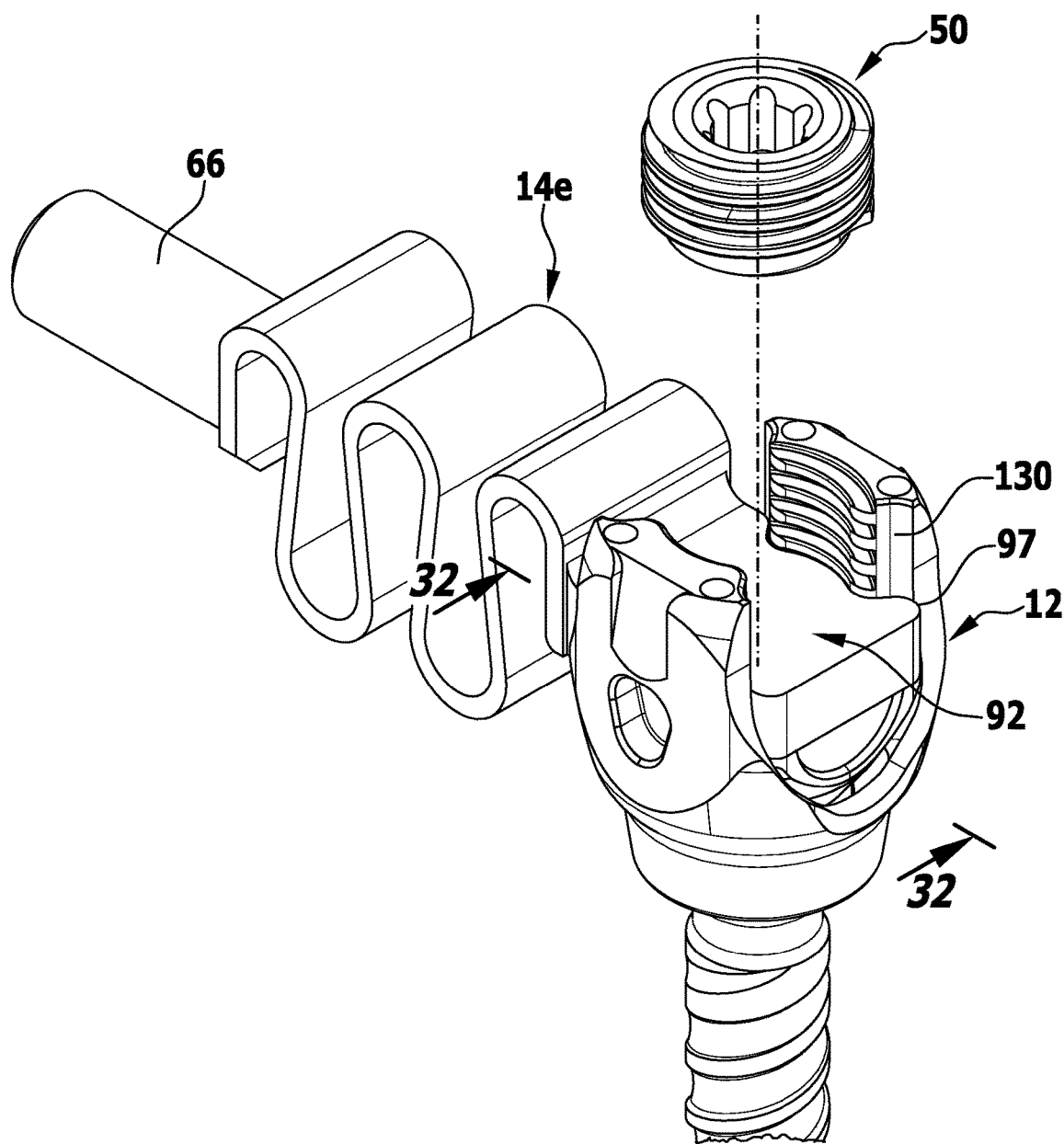
FIG. 31: is a schematic perspective view of a sixth exemplary embodiment of a connection element in the process of being fixed to a bone screw.
Figure 32:
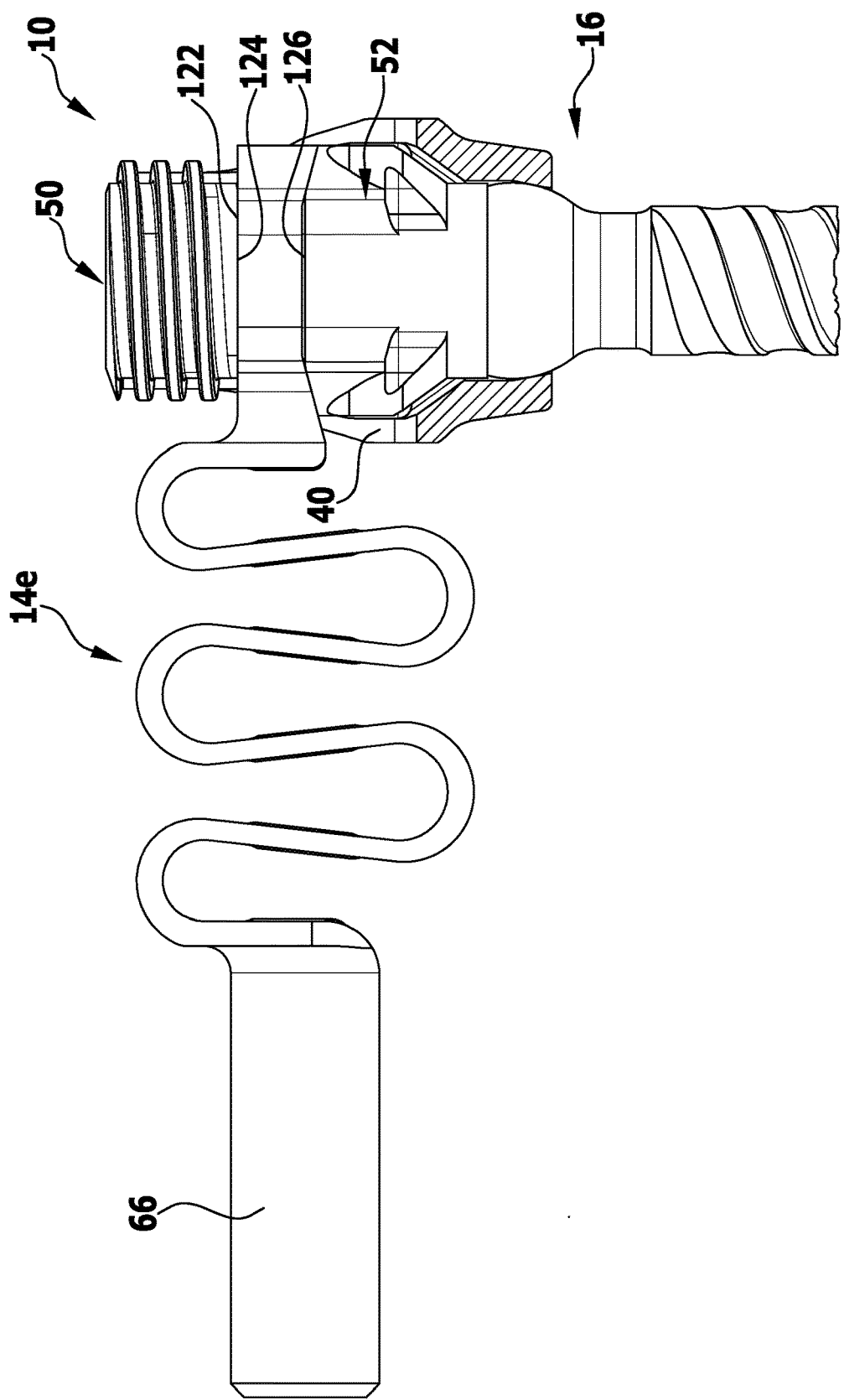
FIG. 32: is a partially sectional view along line 32-32 of FIG. 31.
Figure 33:
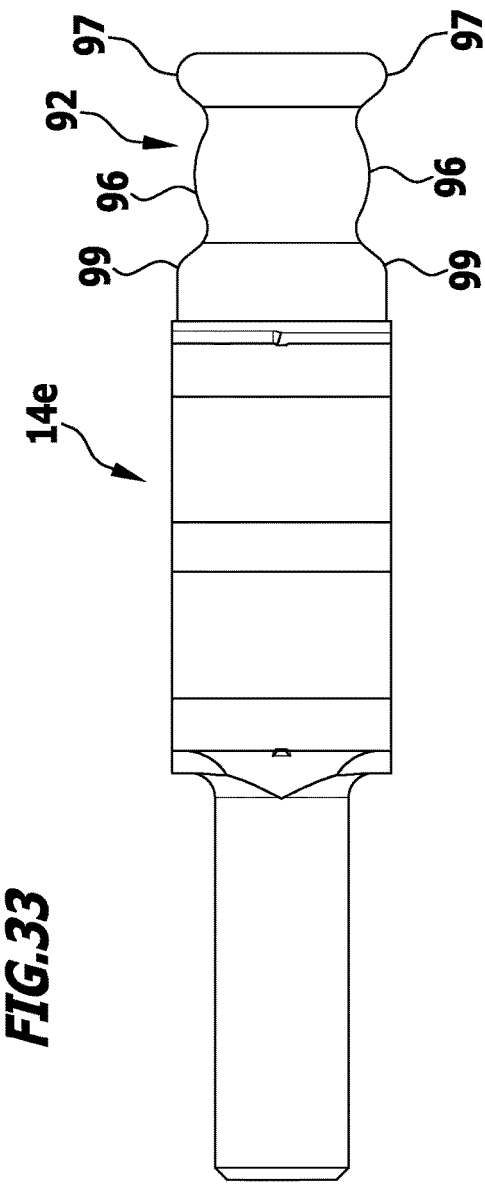
FIG. 33: is a view of the connection element of FIG. 34 in the direction of arrow O.
Figure 34:
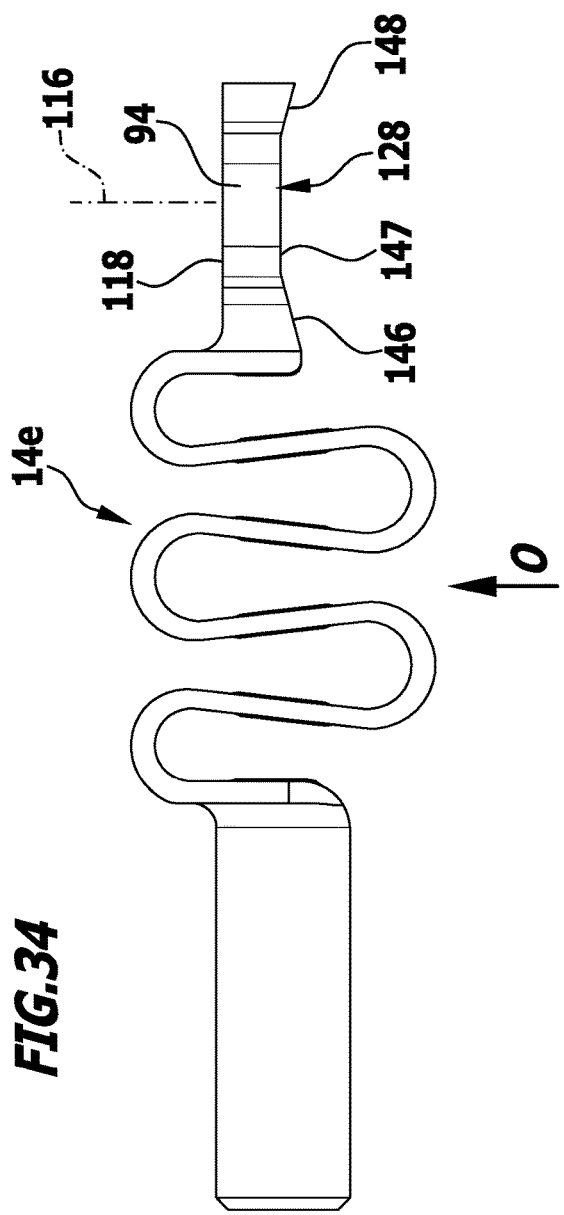
FIG. 34: is a side view of the connection element of FIG. 32.
Figure 35:
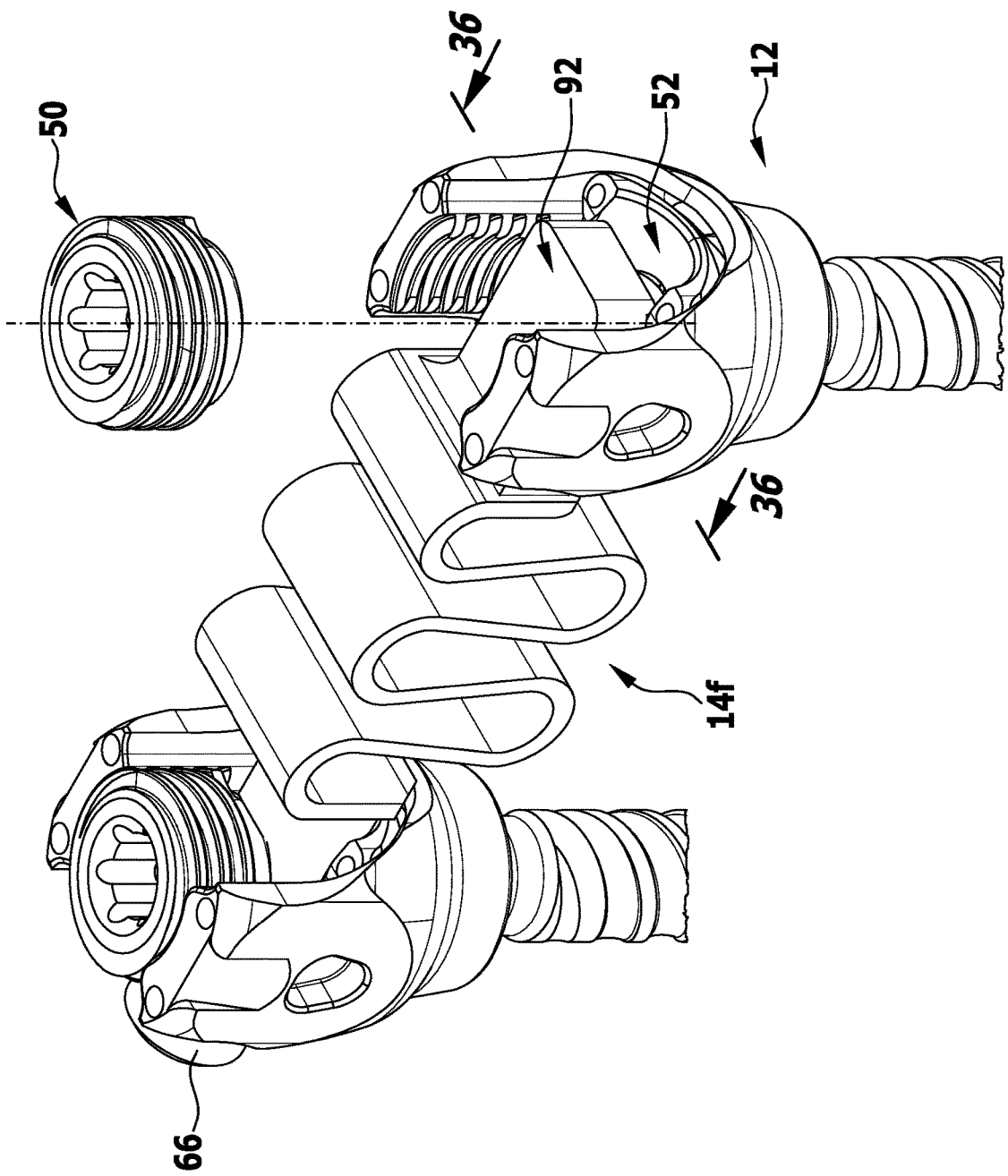
FIG. 35: is a schematic perspective view of a seventh exemplary embodiment of a connection element in the process of being fixed to two bone screws.
Figure 36:
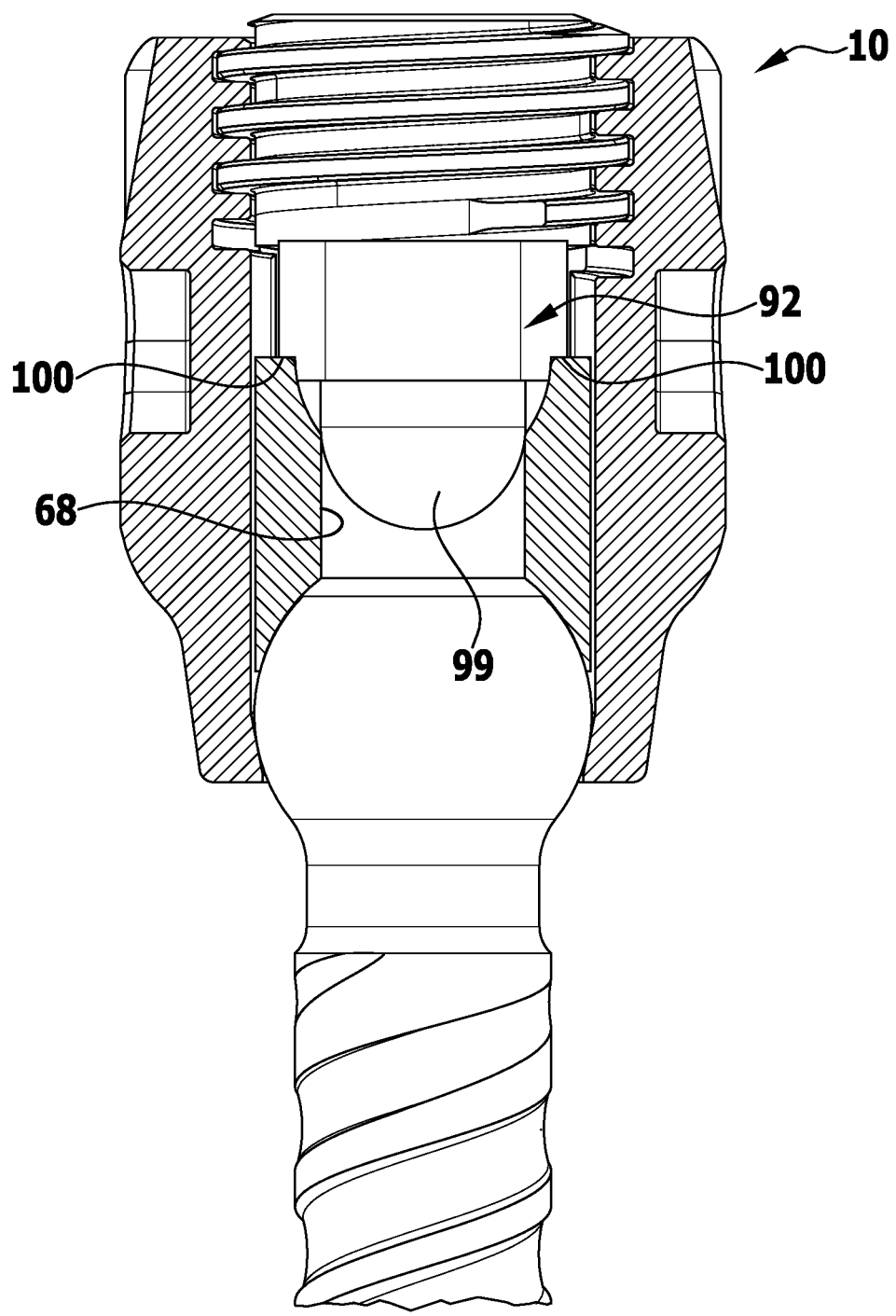
FIG. 36: is a partially sectional view along line 36-36 in FIG. 35.

The first end 66 may, as shown schematically in FIG. 4, be inserted into the connection element receptacle 42 defined on the distal side by the contact surface 64 and secured in clamped manner with the fixing screw 50. At the same time, the holding part 26 is fixed in clamped manner relative to the fixing part 24 in a desired implantation position, in that the clamping force introduced by means of the fixing screw 50 is transferred via the first end 66 to the insert 54, which in turn presses on the head 34.

The connection element 14 comprises the first end 66 and a second end 70 and an at least partially flexible intermediate portion 74 arranged or formed therebetween and defining a longitudinal axis 72. Said intermediate portion takes the form of a winding leaf spring element 76 in the form of a strip. In addition, it comprises a total of five recesses 78 and 80 which are laterally open transversely of the longitudinal axis 72 in a recess direction 82. The three recesses 80 are open in opposing directions relative to the recesses 78. Due to the configuration as a leaf spring element 76, the intermediate portion 74 and thus the connection element 14 are resilient in a defined manner.

A resilience of the intermediate portion 74 may additionally optionally be varied by one or more stiffness modifiers 84. These may for example be arranged or configured in the form of short projections 86 in the form of strips on one or both surfaces 88 and 90 respectively of the leaf spring element 76. Preferably, they are in one piece with the leaf spring element 76. Further examples of the configuration of stiffness modifiers 84 are known from DE 20 2010 008 865 U1.

The second end 70 of the connection element 14 takes the form of a coupling element 92 for fixing the connection element 14 to the bone fixation device 12 in at least one defined orientation relative to the longitudinal axis 72. It has a shape other than a circular cylinder. It is moreover of one-piece configuration, as is the connection element 14 overall.

The coupling element 92 has a coupling element main body 94 and a total of four coupling members 96 and 98. The coupling members 96, which take the form of coupling projections 102 facing convexly away from the coupling element main body 94, extend in a coupling member direction 104, which extends transversely of the longitudinal axis 72. The coupling members 98 take the form of set-back portions 100 on the cuboidal coupling element main body 94 and define a coupling member direction 106 which extends parallel to the longitudinal axis 72.

Furthermore, an end face 108 of the coupling element 92 facing away from the intermediate portion 74 is inclined relative to the longitudinal axis 72. The end face 108 defines an end face plane 110, which forms an end face angle of inclination 112 with the longitudinal axis 72 which preferably lies in a range from around 30° to around 90°. In the case of the connection element 14 illustrated schematically in FIGS. 1 to 9, the end face angle of inclination 112 amounts to around 60°.

The side faces 114 facing away from the coupling element main body 94 and defined by the coupling members 96 together form a portion of a circular cylinder, the longitudinal axis of which defines a preferential direction 116 of the coupling element 92. This extends transversely of the longitudinal axis 72. A diameter defined by the coupling members 96 is conformed to an internal diameter of the internal thread 46, such that the coupling element 92 may be fixed to the bone screw 16 in defined orientation relative to the longitudinal axis 72.

A centre of gravity of the coupling element 92 is spaced from the longitudinal axis 72.

A top 118 of the coupling element main body 94 defines a planar surface portion 120, which defines a plane extending parallel to the longitudinal axis 72. The surface portion 120 forms a clamping surface portion 122 for a distal end 124 of the fixing screw 50. In this way, to clamp the coupling element 92 in the connection element receptacle 42 the end 124 may be pressed substantially flatly against the clamping face portion 122.

The set-back portions 100 are arranged and dimensioned such that they abut edges 126 of the insert 54 extending parallel to the longitudinal axis 72 and facing in the proximal direction.

The connection element 14 defines a preferential direction 116, and may thus be fixed precisely in a defined manner in the connection element receptacle 42. By the coupling members 96 the connection element 14 is additionally secured parallel to the longitudinal axis 72 relative to the bone screw 16, and thus cannot be moved parallel to the longitudinal axis 72 relative to the bone screw 16 even when the fixing screw 50 needs to be loosened a little. Rotation of the connection element 14 about the longitudinal axis 72 relative to the bone screw 16 is likewise not possible.

Further exemplary embodiments of connection elements will be described in greater detail below, these differing substantially in the configuration of their coupling elements. Identical or comparable parts and elements are therefore designated with the same reference signs.

FIGS. 10 to 15 are schematic representations of a second exemplary embodiment of a connection element denoted overall with reference sign 14*a*. The difference in the construction of the connection element 14 is the shape of the coupling element 92.

This likewise has a cuboidal coupling element main body 94, away from which two coupling members 96 extend laterally transversely of the longitudinal axis 72. An end face 108 facing away from the intermediate portion 74 is rounded and forms together with the coupling members 96 a part of a cylindrical disc which comprises a cylindrical side face 114. A diameter of the coupling element 92 defined by the side face 114 corresponds to an internal diameter of the internal thread 46, such that the coupling element 92 may be inserted into the connection element receptacle 42 for axial securing of the connection element 14*a* in the direction of the longitudinal axis 72 relative to the bone screw 16.

In addition, two further coupling members 98 extending parallel to the longitudinal axis 72 are formed on the coupling element main body 94 in the form of set-back portions 100. When the second end 70 has been inserted into the connection element receptacle 42, these abut the edges 126 of the insert 54.

The coupling element 92 defines a preferential direction 116 which extends transversely of the longitudinal axis 72. The top 118 of the coupling element 92 forms a planar clamping surface portion 122 for the distal end 124 of the clamping screw 50.

Because of its configuration, the connection element 14*a* may be oriented both parallel to the longitudinal axis 72 and in the circumferential direction thereof in a defined manner relative to the bone screw 16.

FIGS. 16 to 19 are schematic representations of a third exemplary embodiment of a connection element and are designated overall with the reference sign 14*b*. It differs from the connection element 14 in the configuration of the coupling element 92.

The coupling element 92 has a cuboidal coupling element main body 94, the top 118 of which defines a planar clamping surface portion 122. An end face 118 facing away from the intermediate portion 74 is likewise planar and extends transversely of the longitudinal axis 72.

Two coupling members 96 projecting laterally, i.e. transversely of the longitudinal axis 72 are formed on the coupling element main body 94, as are two coupling members 98 extending parallel to the longitudinal axis 72. The coupling members 98 are formed in the bottom 128 of the coupling element main body 94 in the form of set-back portions 100, which extend parallel to the longitudinal axis 72 over the entire length of the coupling element 92. They are dimensioned and sized such that they in turn abut the edges 126 of the insert 54.

The coupling element main body 94 has a width which corresponds to a clearance between the two wall portions 44, such that the coupling element 72 may be inserted into the connection element receptacle 42.

The coupling members 96 abut the wall portions at concavely curved side faces 130 facing away therefrom, these side faces facing substantially in the direction of the intermediate portion 74 when the coupling element 92 has been inserted. The coupling members 96 are conformed in shape to the side faces 130, such that flat contact between the coupling element 92 and the side faces 130 is possible. The side faces 130 thus form a limit stop for the connection element 14*b*, such that it can only be moved so far parallel to the longitudinal axis 72 in the direction of the bone screw 16 before the coupling members 96 strike against the side faces 130. Rotation of the coupling element 92 in the connection element receptacle 42 is not possible. Overall, the coupling element 92 defines a preferential direction 116 which extends transversely of the longitudinal axis 72.

FIGS. 20 to 25 are schematic representations of a fourth exemplary embodiment of a connection element designated overall with the reference sign 14*c*. It differs in structure from the connection element 14 in the coupling element 92 forming a second end. The coupling element 92 has a substantially cuboidal coupling element main body 94, which comprises two coupling members 96 in the form of coupling projections 102, which protrude laterally on the coupling element main body 94 transversely of the longitudinal axis 72. The coupling members 96 define a diameter which corresponds to an internal diameter of the internal thread 46.

Each of the coupling members 96 is adjoined both on a side facing the intermediate portion 74 and on a side remote therefrom by two coupling members 97, which likewise take the form of coupling projections. These project a little further from the coupling element main body 94 than the coupling members 96. Furthermore they have an external contour which is conformed to the concave side faces 130 of the wall portions 44. In this way, the coupling element 92, as is readily visible for example in FIG. 22, may be inserted in a substantially positive-locking manner from above into the connection element receptacle 42.

The top 118 of the coupling element 92 is planar and forms a clamping surface portion 122 for the distal end 124 of the fixing screw 50.

The coupling element 92 further has a connection element contact face 134 for application against a further connection element, for example in the form of a connecting rod 132, which is elongate and takes the form of a circular cylinder. The connection element contact face 134 takes the form of a hollow-cylindrical wall face 136, against which an outer face 138 of the connecting rod 132 may be flatly applied. Facing away from the intermediate portion 74 in the direction of the coupling element 92 is a striking surface 140, against which an end face 142 of the connecting rod 132 may strike.

The particular configuration of the coupling element 92 allows this to be fixed on the bone screw 16 together with the connecting rod 132. The connecting rod 132 is then held clamped between the coupling element 92 and the insert 54, the coupling element 92 is between the connecting rod 132 and the fixing screw 50.

FIGS. 26 to 30 are schematic representations of a fifth exemplary embodiment of a connection element designated overall with the reference sign 14d. It differs in structure from the connection element 14 in the configuration of the coupling element 92.

The coupling element 92 in turn has a cuboidal main body with an end face 108 facing away from the intermediate portion 74 and inclined relative to the longitudinal axis 72. The top 118 of the coupling element 92 is planar and forms a clamping surface portion 122 for the distal end 124 of the fixing screw 50.

Main body side faces 144 extending substantially parallel to the longitudinal axis 72 are curved at the point of transition to the bottom 128 and form coupling members 98 in the form of set-back portions 100. The curvature of the coupling members 98 corresponds to an internal diameter defined by the contact surface 64 of the insert 54, such that the coupling members 98 abut substantially flatly against the contact surface 64. This is readily visible for example from FIG. 28.

A further coupling member 99 protrudes from the bottom 128 transversely of the longitudinal axis 72 and defines a preferential direction 116. The coupling member 99 takes the form of a coupling projection 103 and has the shape of a cone extending away from the bottom 128. The cone is dimensioned such that it may be introduced into the bore 68 of the insert 54.

Through the particular configuration of the coupling element 92, this may be secured to the bone screw 16 both parallel to the longitudinal axis 72 and against rotation about the same.

FIGS. 31 to 34 are schematic representations of a sixth exemplary embodiment of a connection element designated overall with the reference sign 14e. It differs in structure from the connection element 14 in the configuration of the coupling element 92.

The coupling element 92 has a substantially cuboidal coupling element main body 94 with two laterally projecting coupling members 96. These are convexly curved away from the coupling element main body 94 and define a diameter which corresponds to an internal diameter of the internal thread 46.

Facing away from the intermediate portion 74, a coupling member 97 in the form of a further coupling projection in each case adjoins the coupling members 96. The coupling members 97 have an outer contour, such that they may be applied at least in places substantially flatly against the side faces 130 of the wall portions 44.

On the proximal side, further coupling projections 99 adjoin the coupling members 96, said further coupling projections substantially taking the form of the coupling projections 96 of the connection element 14b. The coupling members 96 have an outer contour, which at least in part allows a flat contact against the side faces 130 of the wall portions 44.

The top 118 of the coupling element 92 forms a planar clamping surface portion 122 for the distal end 124 of the fixing screw 50. The bottom 128 of the coupling element 92 is formed by three coupling element main body side faces 146, 147 and 148 inclined relative to one another. The coupling element main body side face 147 extends parallel to the top 148 and substantially in the region of the coupling members 96. The coupling element main body side face 148 is inclined relative to the coupling element main body side face 147 and forms an obtuse angle with the latter. The coupling element main body side face 148 extends substantially in the region of the coupling members 97.

The coupling element main body side face 146 extends substantially in the region of the coupling members 99 and forms an obtuse angle with the coupling element main body side face 147. Overall, the three coupling element main body side faces 146, 147 and 148 together form a substantially concavely curved bottom 128 of the coupling element 92.

The coupling element 92 defines a preferential direction 116 which extends transversely of the longitudinal axis 72.

The configuration of the coupling element 92 allows the connection element 14e to be secured to the bone screw 16 with the fixing screw 50 both parallel to the longitudinal axis 72 and against rotation about this.

FIGS. 35 to 38 are schematic representations of a seventh exemplary embodiment of a connection element designated overall with the reference sign 14f. It differs from the connection element 14 in the configuration of the coupling element 92.

The coupling element main body 94 is substantially cuboidal and has at its bottom 128 two coupling members 98 in the form of set-back portions 100 extending parallel to the longitudinal axis, such that the coupling element 92 may be applied with the set-back portions 100 against the edges 126 of the insert 54. The width of the main body corresponds substantially to an inside width between the wall portions 44.

A coupling member 99 protrudes from the bottom 128 transversely of the longitudinal axis 72, said coupling member being substantially cylindrical and defining an external diameter which corresponds to an internal diameter of the bore 68 of the insert 54. An end 150 of the coupling member 99 facing away from the coupling element main body 94 takes the form of a hemisphere 152.

The coupling element 92 thus defines a preferential direction 116 and allows the connection element 14f to be secured to the bone screw 16 by means of the fixing screw 50 in a direction parallel to the longitudinal axis 72 and against rotation about the longitudinal axis 72.

Figure 39:
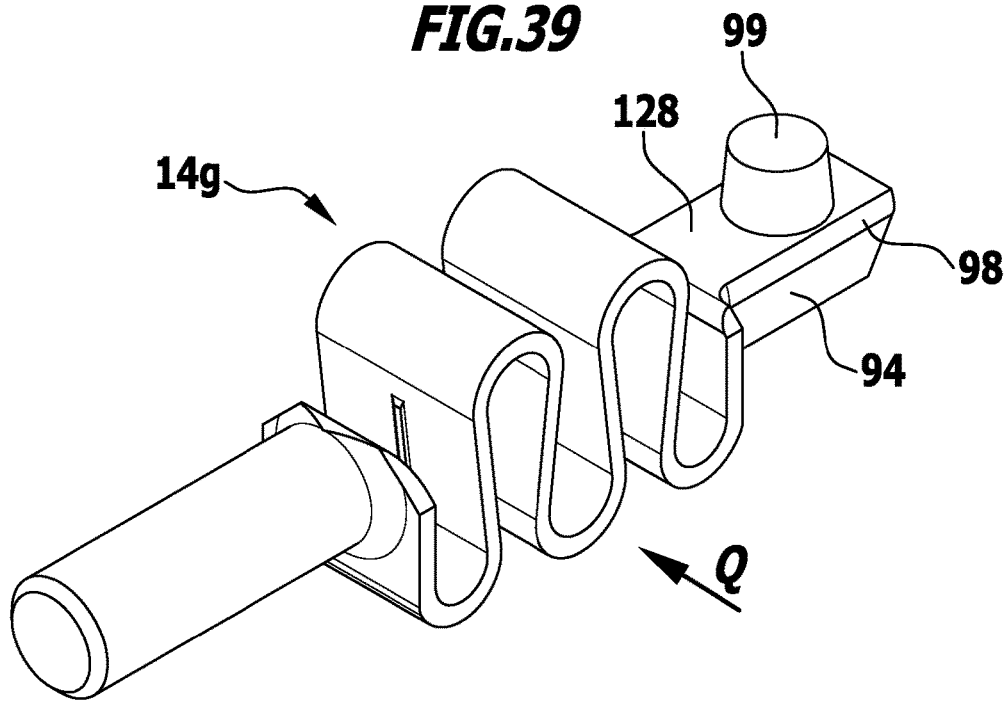
FIG. 39: is a perspective view of an eighth exemplary embodiment of a connection element.
Figure 40:
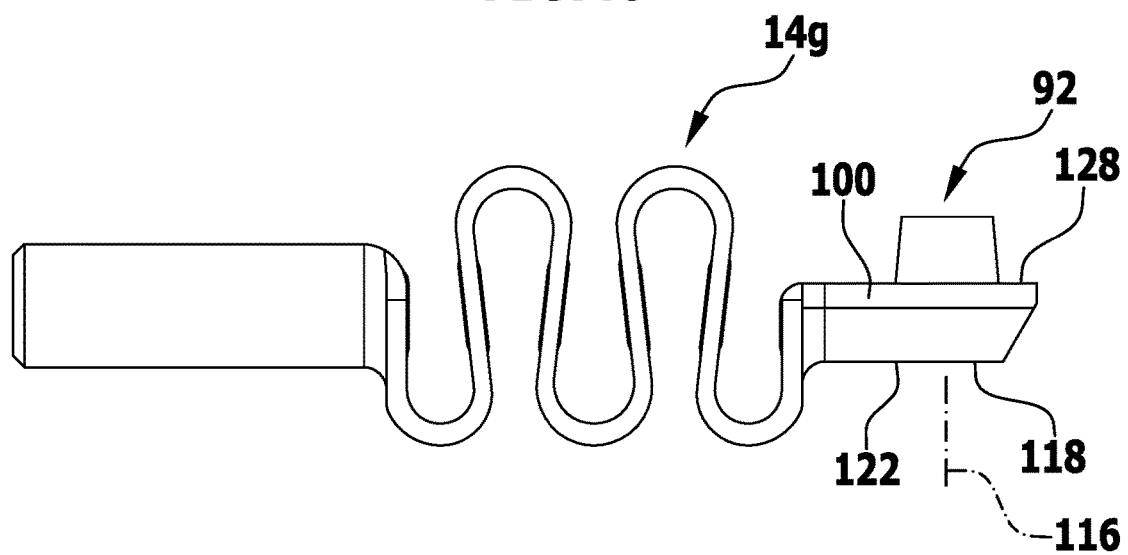
FIG. 40: is a view of the connection element of FIG. 39 in the direction of arrow Q.
Figure 41:
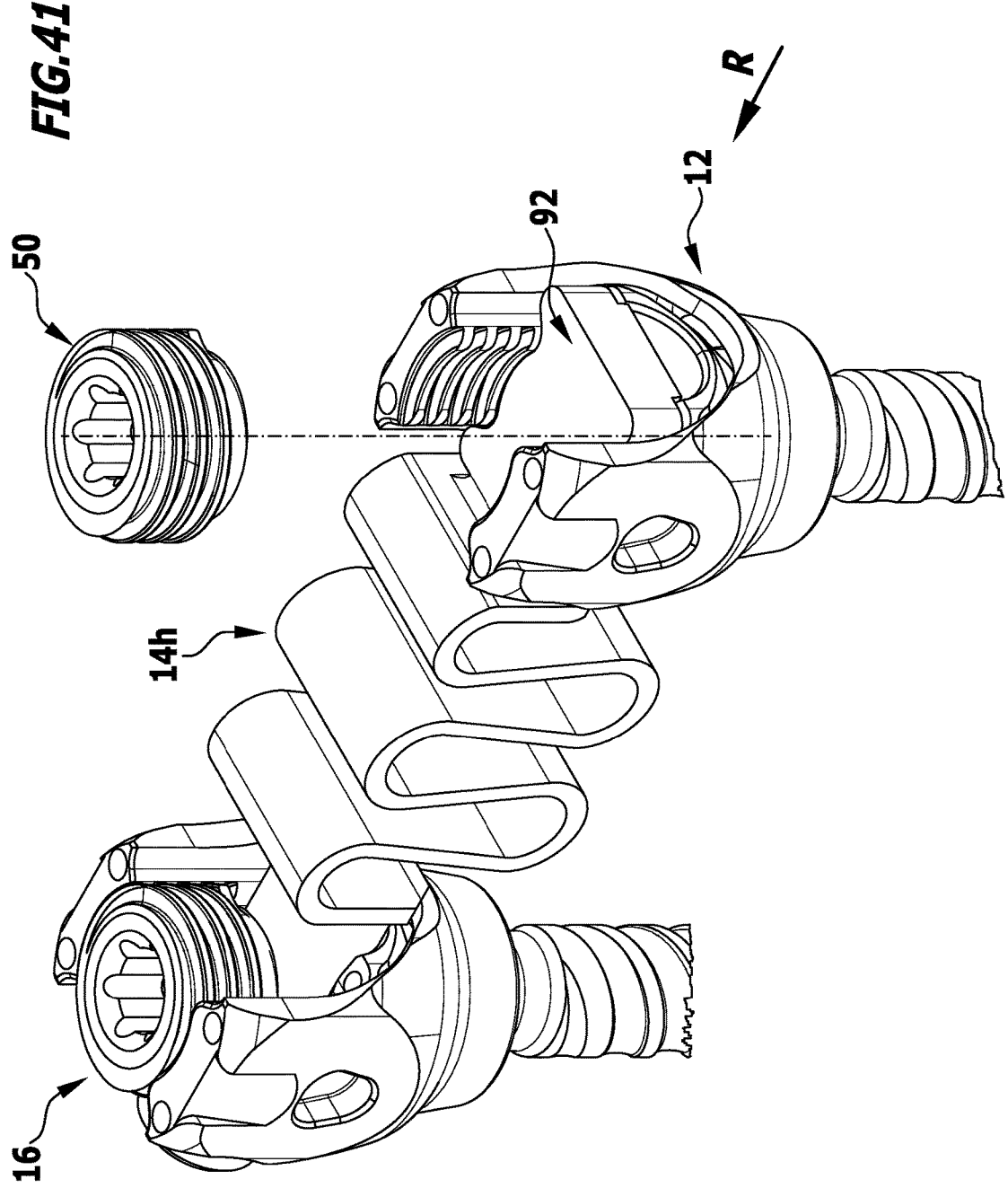
FIG. 41: is a schematic perspective view of a ninth exemplary embodiment of a connection element in the process of being fixed to two bone screws.
Figure 42:
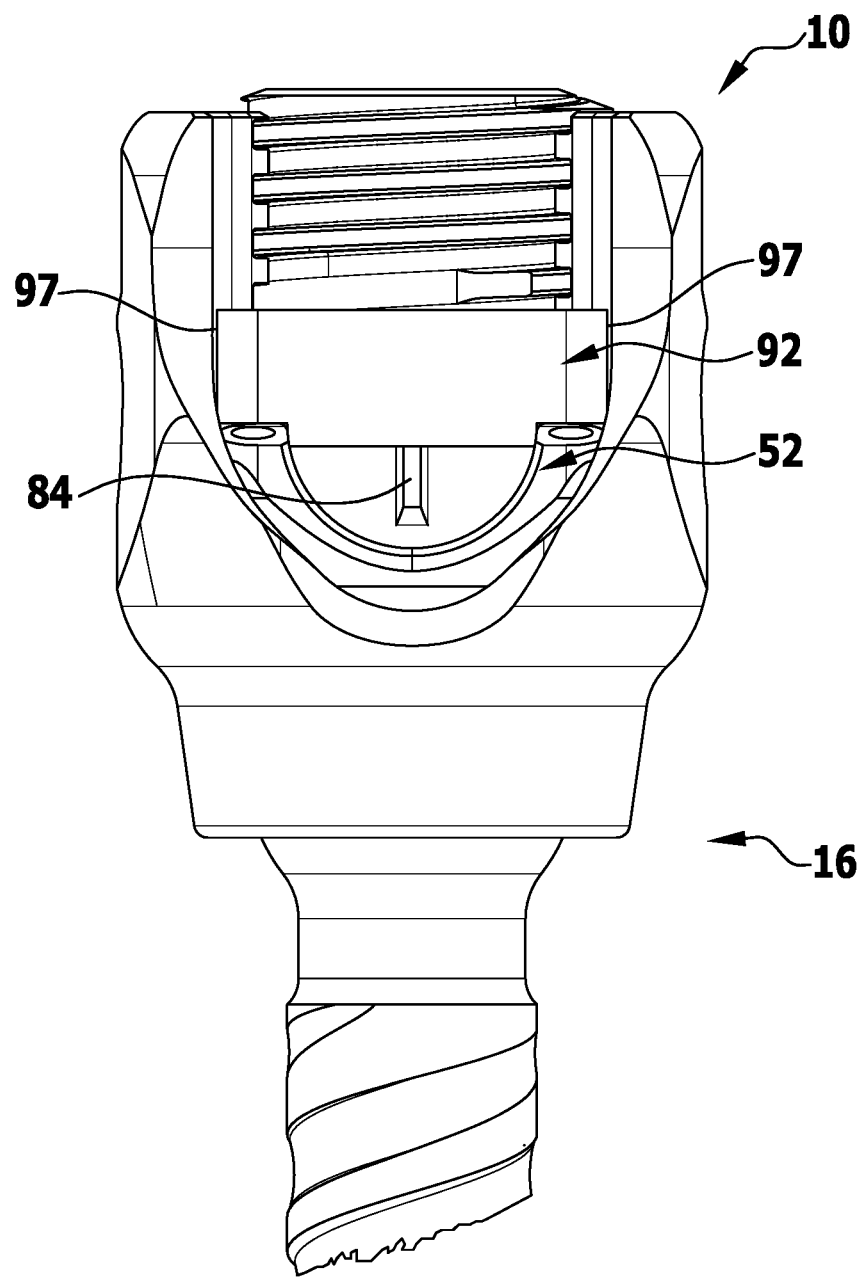
FIG. 42: is a view of the arrangement of FIG. 41 in the direction of arrow R.
Figure 50:
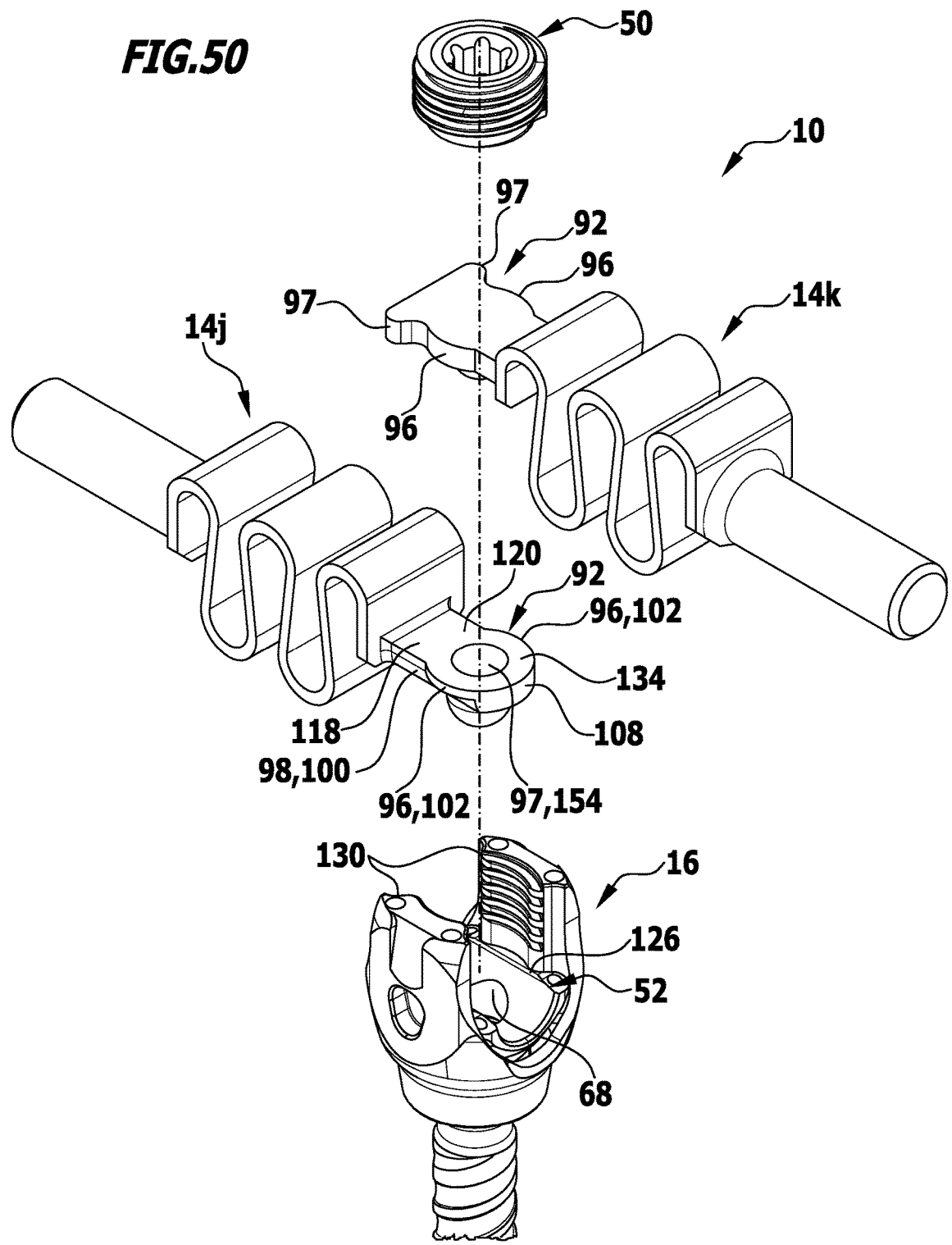
FIG. 50: is an exploded representation of the arrangement of FIG. 49.

FIGS. 39 and 40 are schematic representations of an eighth exemplary embodiment of a connection element designated overall with reference sign 14g. It differs from the connection element 14 in the configuration of the coupling element 92.

The coupling element 92 has a substantially cuboidal main body 94, with two coupling members 98 extending parallel to the longitudinal axis 72 and taking the form of set-back portions 100. The top 118 of the coupling element 92 forms a planar clamping surface portion 122 for the distal end 124 of the fixing screw 50.

A coupling member 99 in the form of a cone with truncated point protrudes from the bottom 128 of the coupling element main body 94. The coupling member 99 is dimensioned such that it may be introduced in particular into the bore 68 in the insert 54.

The coupling element 92 defines a preferential direction 116 and allows the connection element 14g to be fixed to a bone screw 16 with the fixing screw 50 both parallel to the longitudinal axis 72 and against rotation about the longitudinal axis 72.

FIGS. 41 to 45 are schematic representations of a ninth exemplary embodiment of a connection element designated overall with the reference sign 14h. This differs in structure from the connection element 14 in the configuration of the coupling element 92.

The coupling element 92 corresponds in structure substantially to the coupling element 92 of the connection element 14c. It likewise comprises coupling members 96 and 97 and has a top 118 which forms a planar clamping surface portion 122. The bottom 128 of the coupling element 92 is likewise planar. However, unlike with coupling element 92 of the connection element 14c, with the connection element 14h coupling members 98 extending parallel to the longitudinal axis 72 take the form of set-back portions 100, which are arranged and dimensioned such that they abut the edges 126 of the insert 54 when the coupling element 92 engages in the connection element receptacle 42.

The coupling element 92 defines a preferential direction 116 and may be secured with the fixing screw 50 in the connection element receptacle 42 both against movement parallel to the longitudinal axis 72 and against rotation about the longitudinal axis 72.

FIGS. 46 to 48 are schematic representations of a tenth exemplary embodiment of a connection element designated overall with the reference sign 14i. It differs from the connection element 14 in the configuration of the coupling element 92. The coupling element 92 is configured substantially identically to the coupling element 92 of the connection element 14d. It differs therefrom in that side faces 114 of the coupling element main body facing away from one another bear two coupling members 96 protruding diametrically away from one another and taking the form of coupling projections 102. The coupling members 96 define an external diameter which corresponds to an internal diameter of the internal thread 46. The coupling element 92 of the connection element 14i may thus be inserted in similar manner to the connection element 14d into the connection element receptacle 42, wherein in addition the coupling members 96 assist the conical coupling member 99 protruding from the bottom 128 in preventing movement of the connection element 14i relative to the bone screw 16 parallel to the longitudinal axis 72.

The coupling member 92 of the connection element 14i also defines a preferential direction 116, which extends transversely of the longitudinal axis 72.

FIGS. 49 to 53 are schematic representations of two further exemplary embodiments of connection elements designated overall with the reference signs 14j and 14k respectively. They differ from the connection element 14 in the configuration of their coupling elements 92.

The coupling element 92 of the connection element 14j is substantially cuboidal and, like the coupling element 92 of the connection element 14a, has two coupling members 96 in the form of coupling projections 102 protruding from the coupling element main body 94 in diametrically opposed directions.

An end of the coupling element 92 facing away from the intermediate portion 74 takes the form of a cylindrical end face 108, so as to form overall a planar cylindrical disc. The top 128 of the coupling element 92 forms a planar surface portion 120. A coupling member 99 in the form of a substantially cylindrical coupling projection 103 protrudes from the bottom 128 transversely of the longitudinal axis 72, and the end of said coupling projection facing away from the coupling element main body 94 is spherically rounded. The external diameter of the coupling member 99 is conformed to the internal diameter of the bore 68 of the insert 54.

Furthermore, two coupling members 98 are formed on the coupling element 92 which take the form of set-back portions 100, extend parallel to one another and extend as far as the end face 108. The set-back portions 100 are dimensioned such that they may abut the edges 126 of the insert 54.

A coupling member 97 in the form of a coupling recess 154 is formed on the top 118 of the coupling element 92. The coupling recess 154 is hollow-spherical in shape. It is arranged and formed substantially coaxially to the coupling member 99.

The top 118 furthermore forms a connection element contact face 134. A corresponding connection element contact face 134 of the coupling element 92 of the connection element 14k may be applied thereto.

The coupling element 92 of the connection element 14k has a planar top 118, which forms a planar clamping surface portion 122 for the end 124 of the fixing screw 50. The coupling element main body 94 is substantially cuboidal and likewise has two coupling members 96 projecting transversely of the longitudinal axis 72. These define a common external diameter, which corresponds to an internal diameter of the internal thread 46.

In the direction away from the intermediate portion 74, coupling members 97 in the form of coupling projections with a shape corresponding to the concave side faces 130 of the wall portions 44 adjoin the coupling members 96.

A further coupling member 99 projects from the bottom 128 of the coupling element 92 of the connection element 14k, and has a shape corresponding to the coupling recess 154, such that the coupling member 99 may be introduced in positive-locking manner into the coupling recess 154.

The two connection elements 14j and 14k may be fixed with their two coupling elements 92 jointly in a connection element receptacle 42 of a bone screw 16. First of all, the coupling element 92 of the connection element 14j is inserted in the described manner into the connection element receptacle 42, such that the coupling member 99 protrudes into the bore 68. Then the connection element 14k may be inserted with its coupling element 92 into the connection element receptacle 42, such that the coupling member 92 protrudes into the coupling recess 154.

With the fixing screw 50 the two connection elements 14j and 14k may be fixed in jointly clamped manner to the bone screw 16. The particular configuration of the coupling elements 92 of the connection elements 14j and 14k in practice allows simple extension of a connection element.

Figure 54:
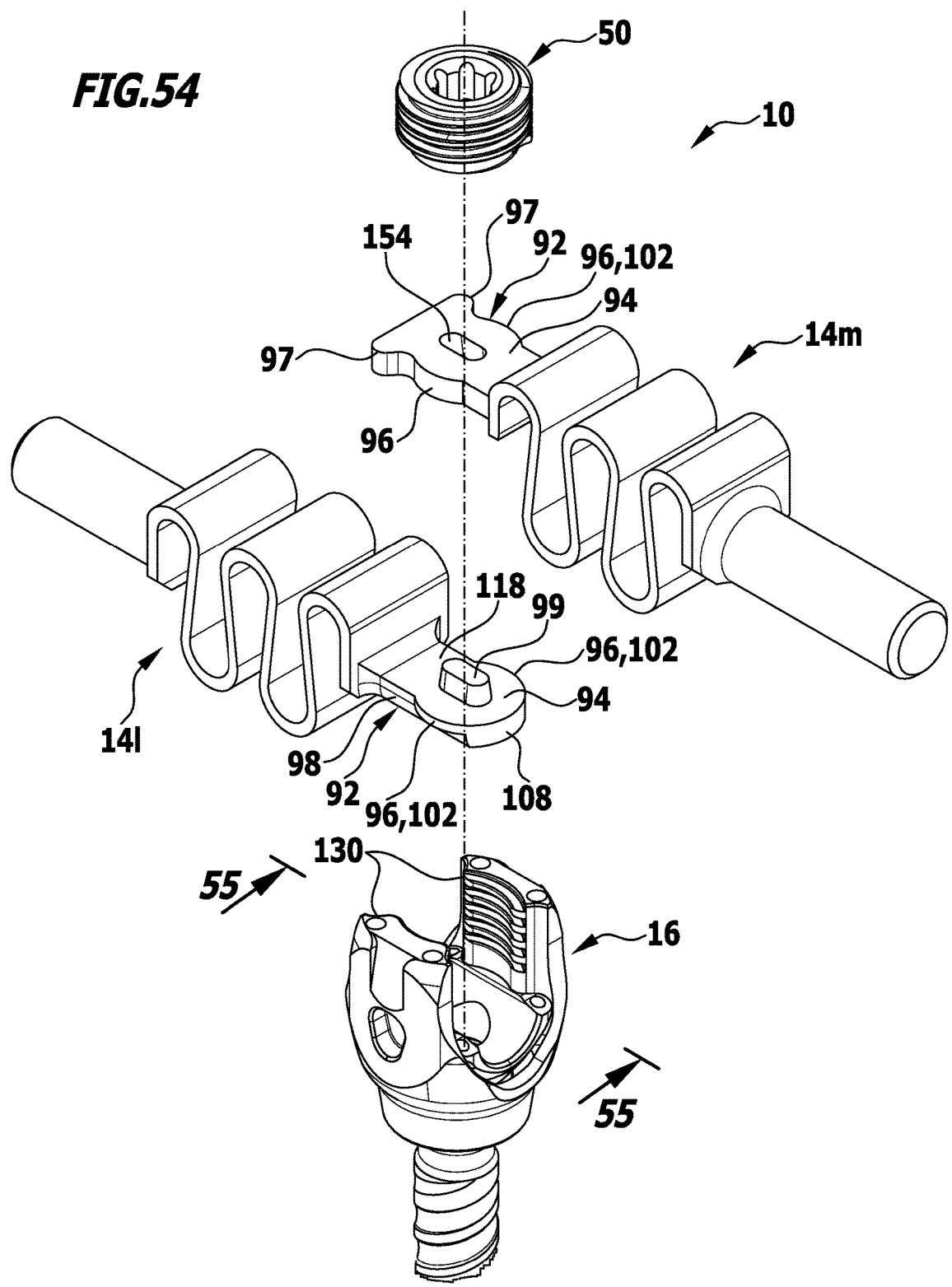
FIG. 54: is a schematic perspective view of a thirteenth and a fourteenth exemplary embodiment of a connection element in the process of being jointly fixed to a single bone screw.
Figure 55:
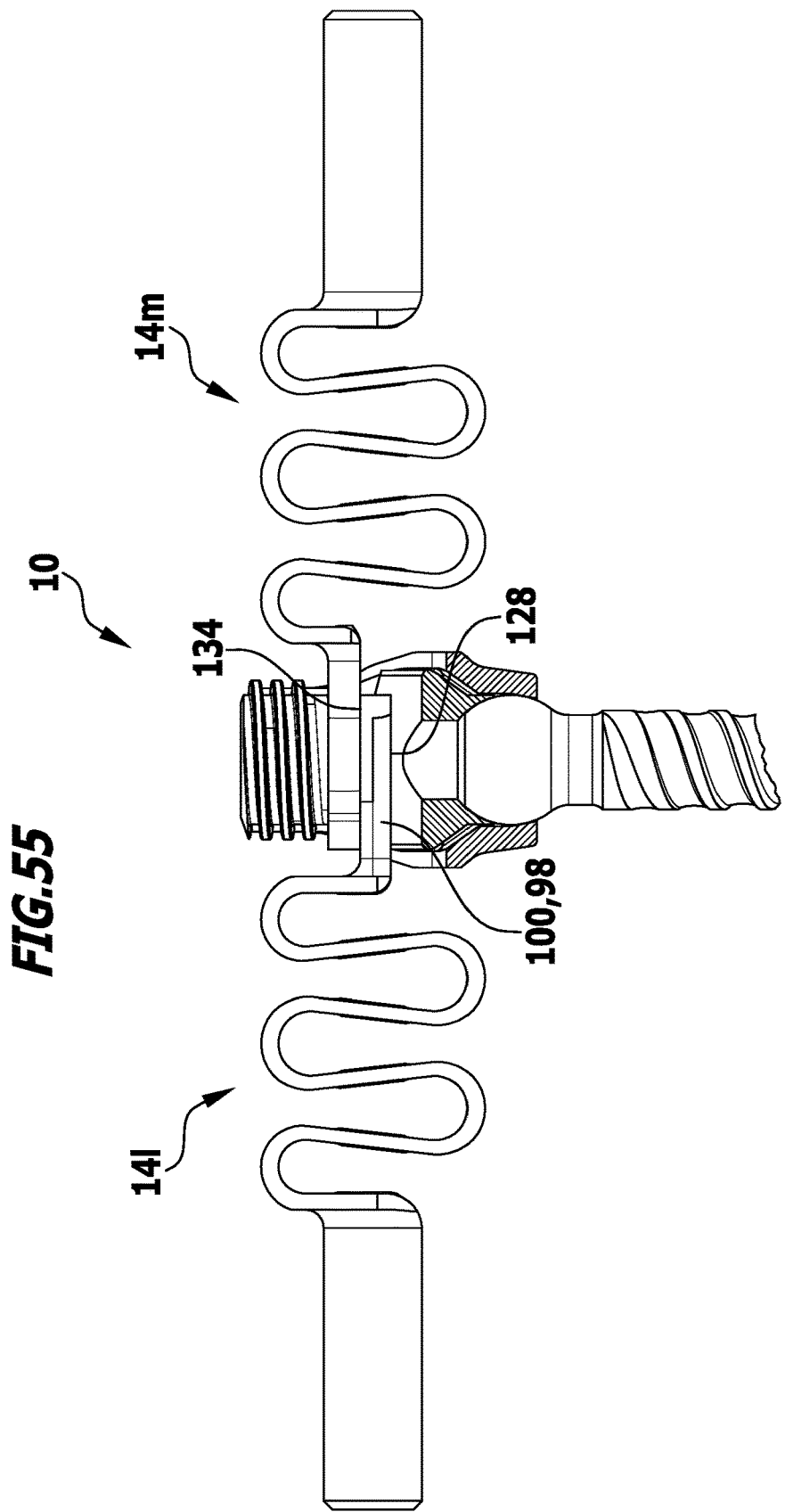
FIG. 55: is a partially sectional view along line 55-55 in FIG. 54.
Figure 56:
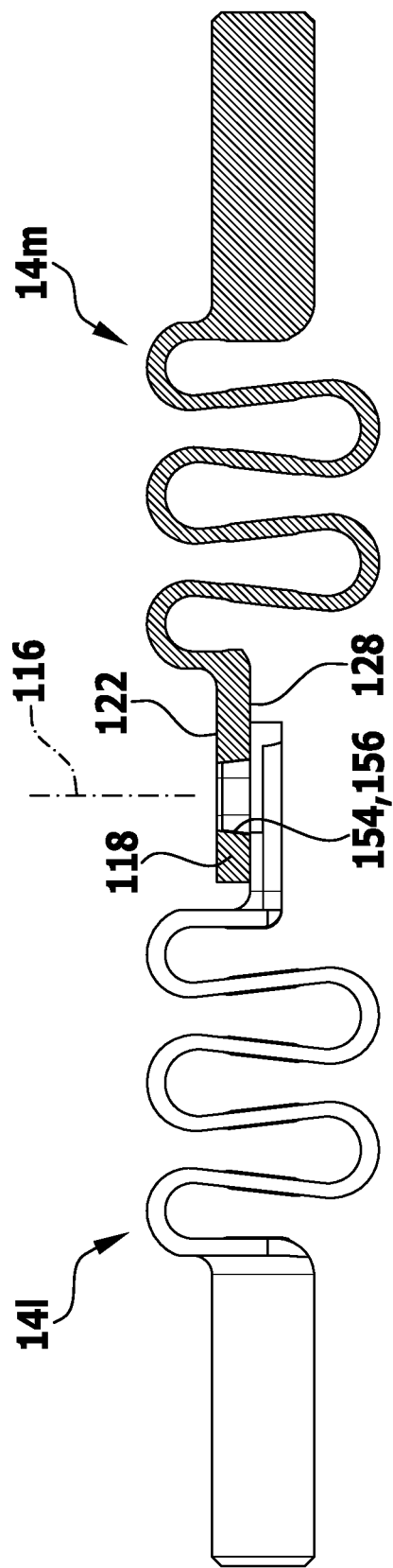
FIG. 56: is a partially sectional side view of the two coupled-together connection elements of FIG. 55.
Figure 57:
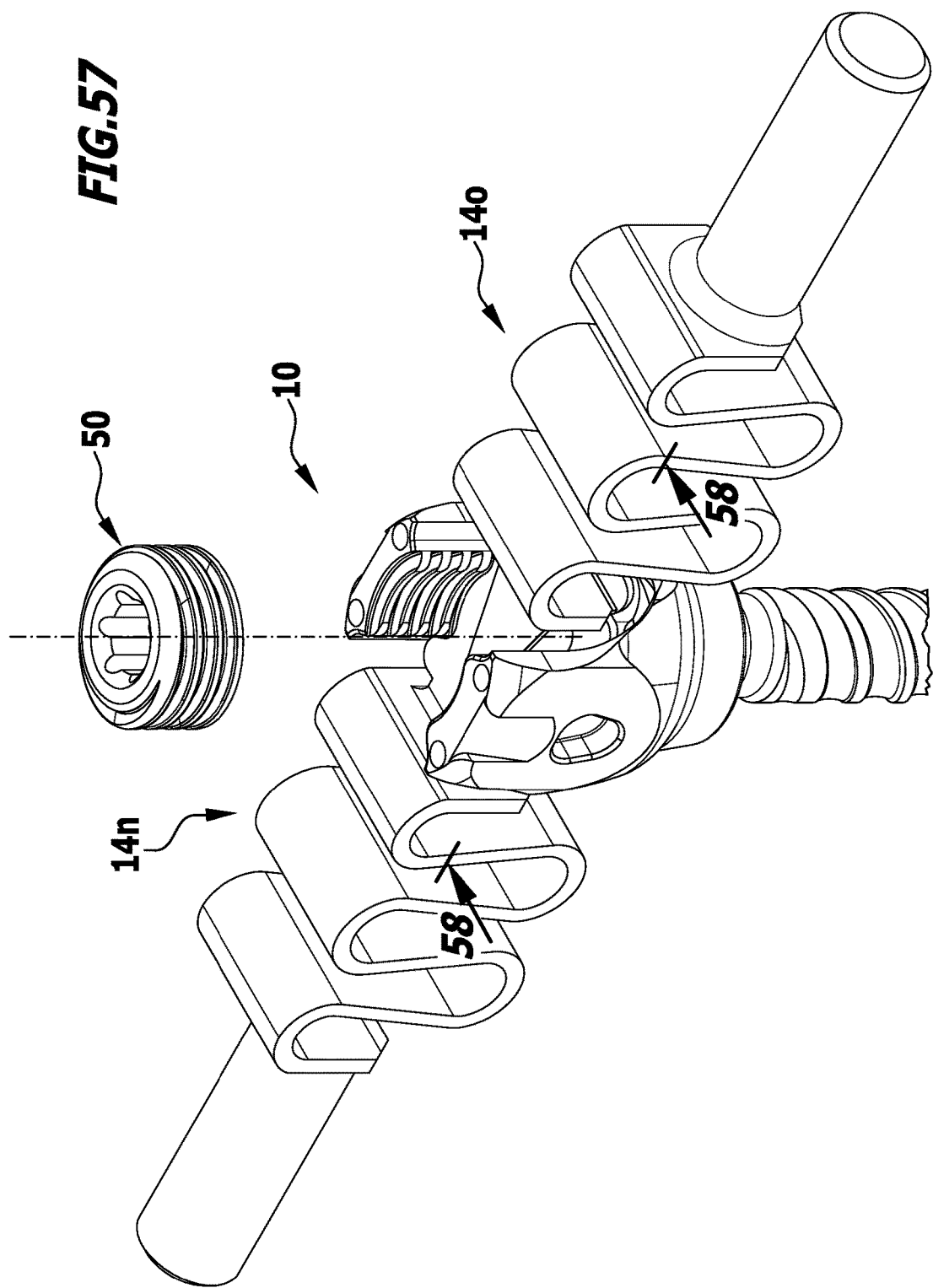
FIG. 57: is a schematic perspective view of a fifteenth and a sixteenth exemplary embodiment of a connection element in the process of being jointly fixed to a single bone screw.
Figure 58:
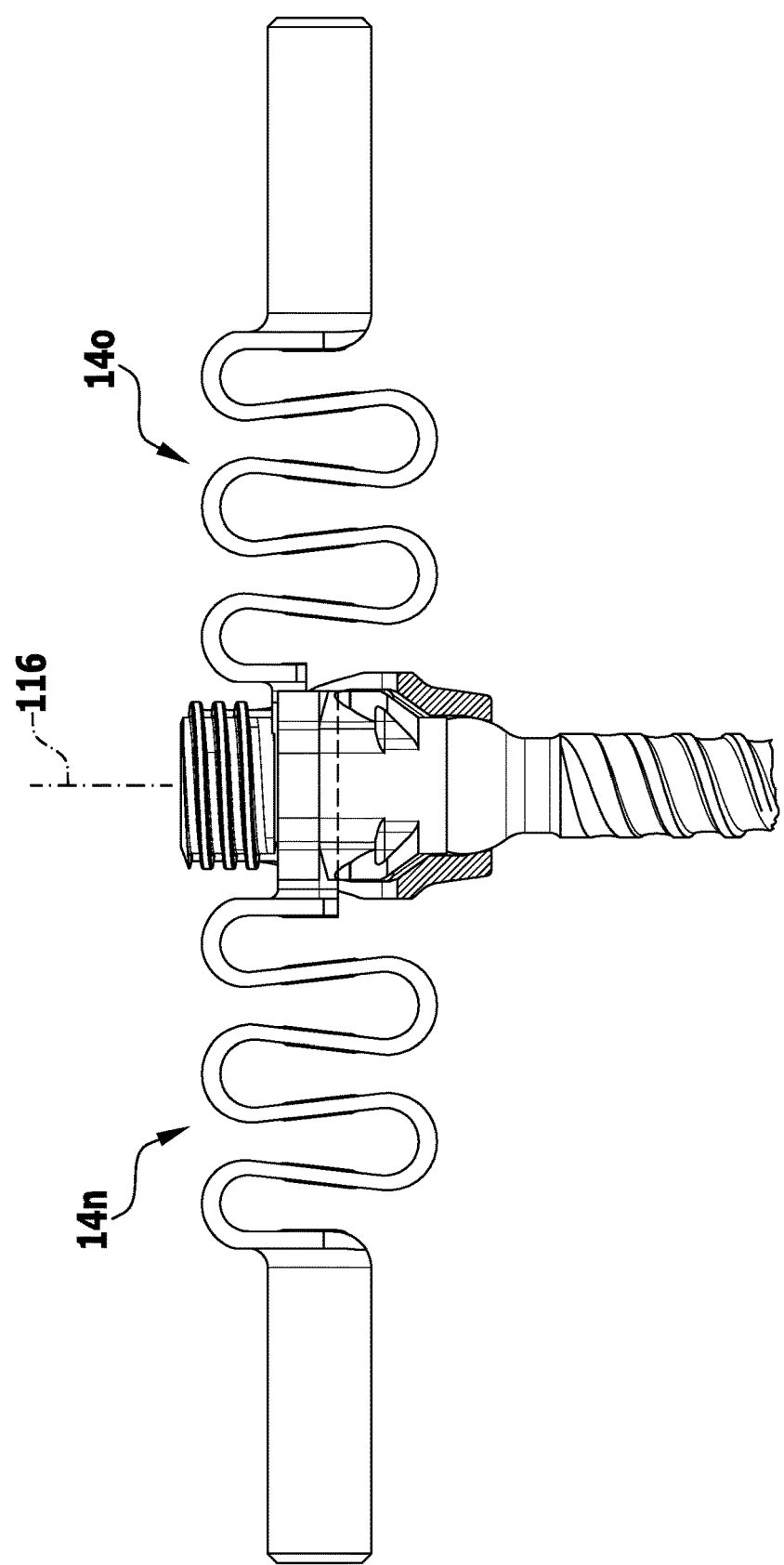
FIG. 58: is a partially sectional view of the arrangement of FIG. 57 along line 58-58.
Figure 59:
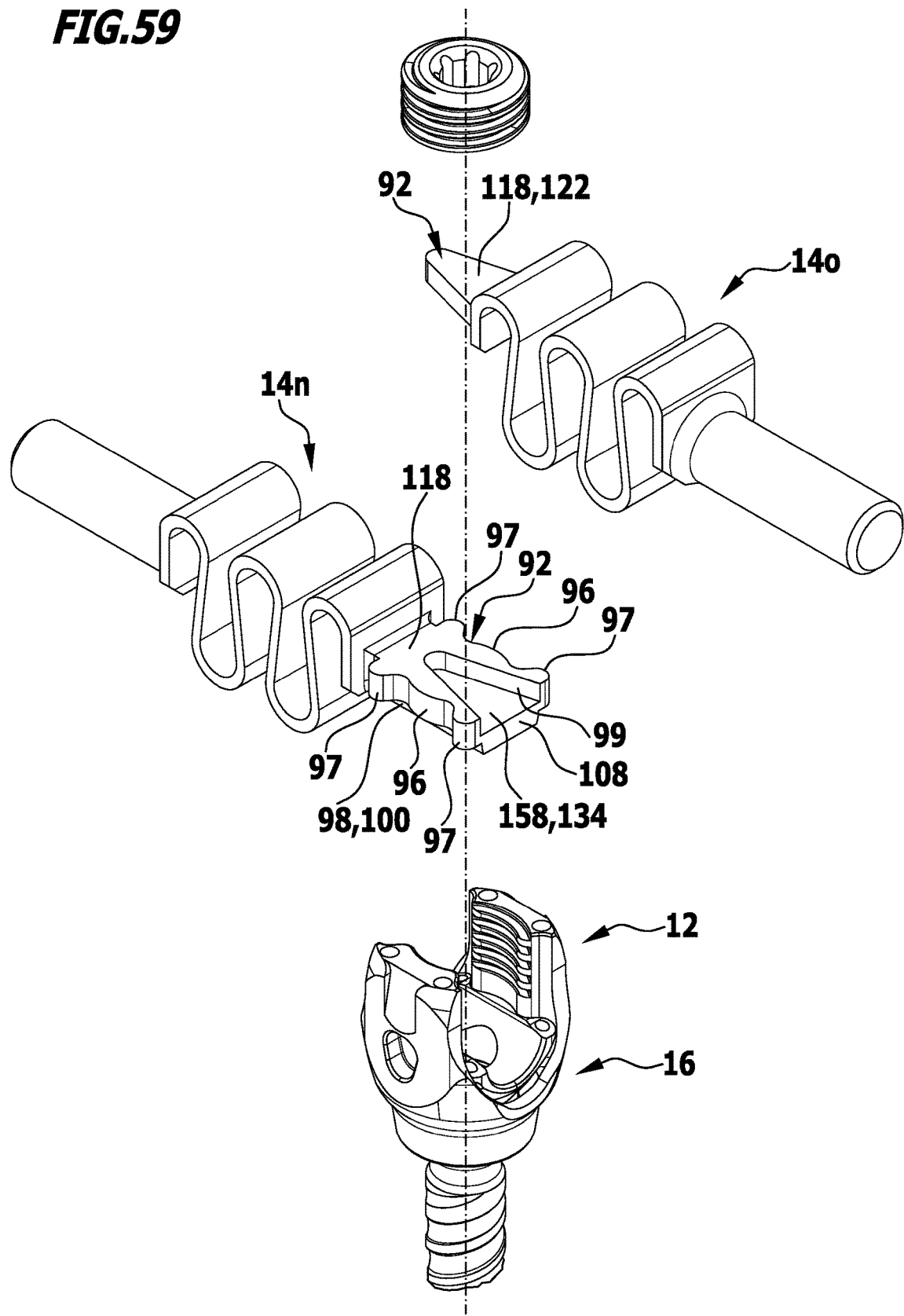
FIG. 59: is an exploded representation of the arrangement of FIG. 57.
Figure 60:
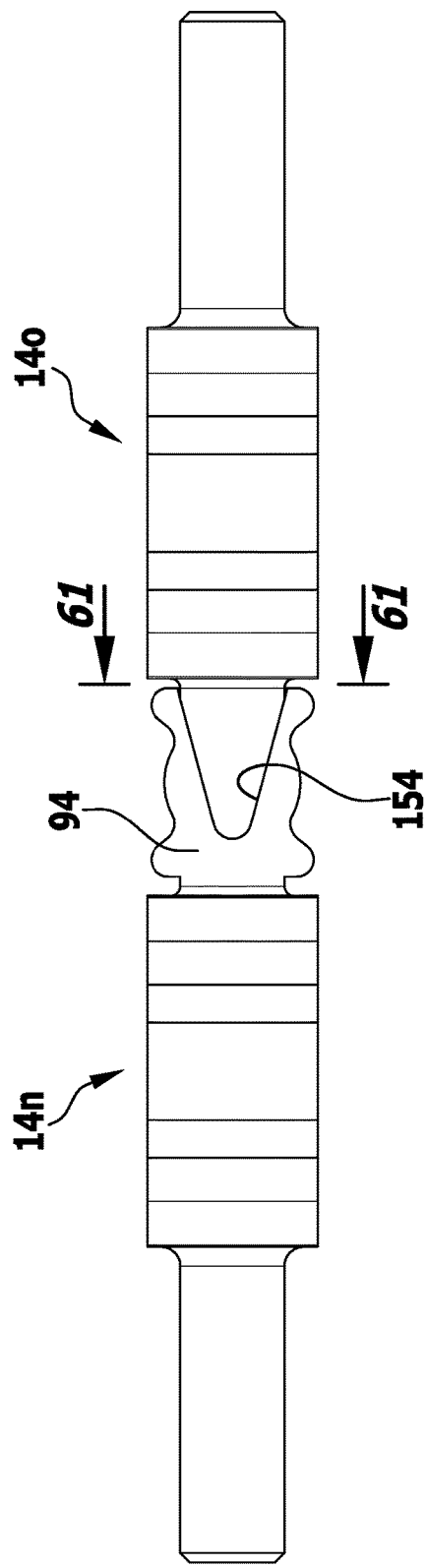
FIG. 60: is a plan view of the coupled-together connection elements of FIG. 57.
Figure 61:
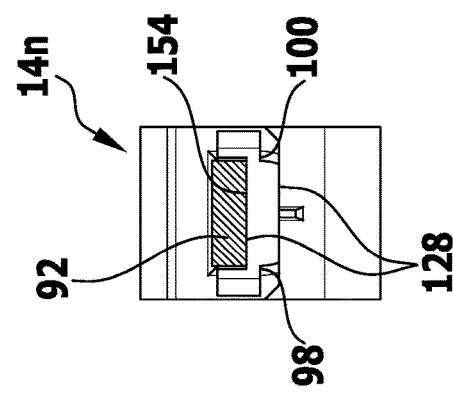
FIG. 61: is a sectional view along line 61-61 in FIG. 60.
Figure 62:
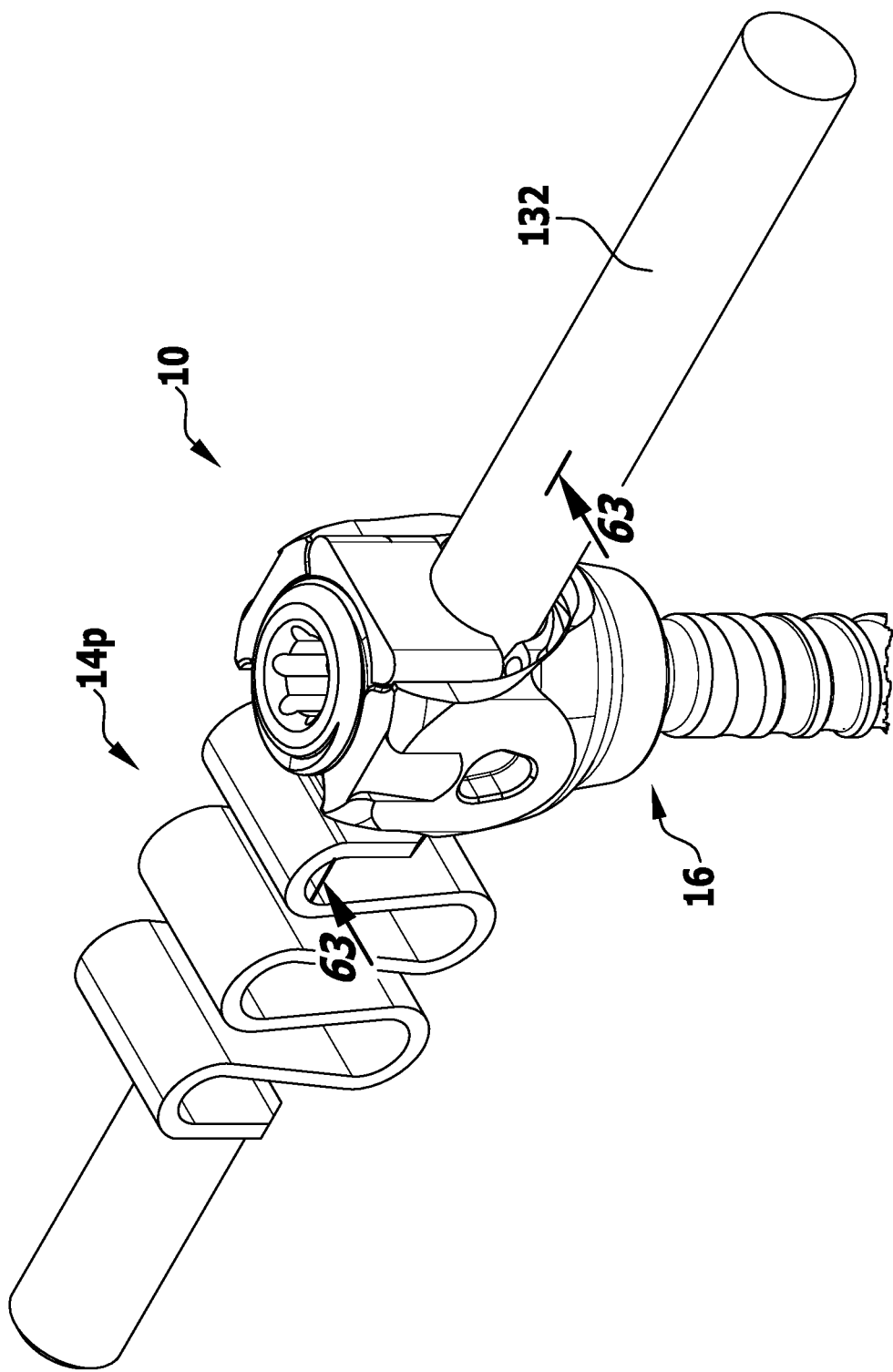
FIG. 62: is a schematic perspective view of a seventeenth exemplary embodiment of a connection element which is fixed to a bone screw with a further rod-shaped connection element.
Figure 63:
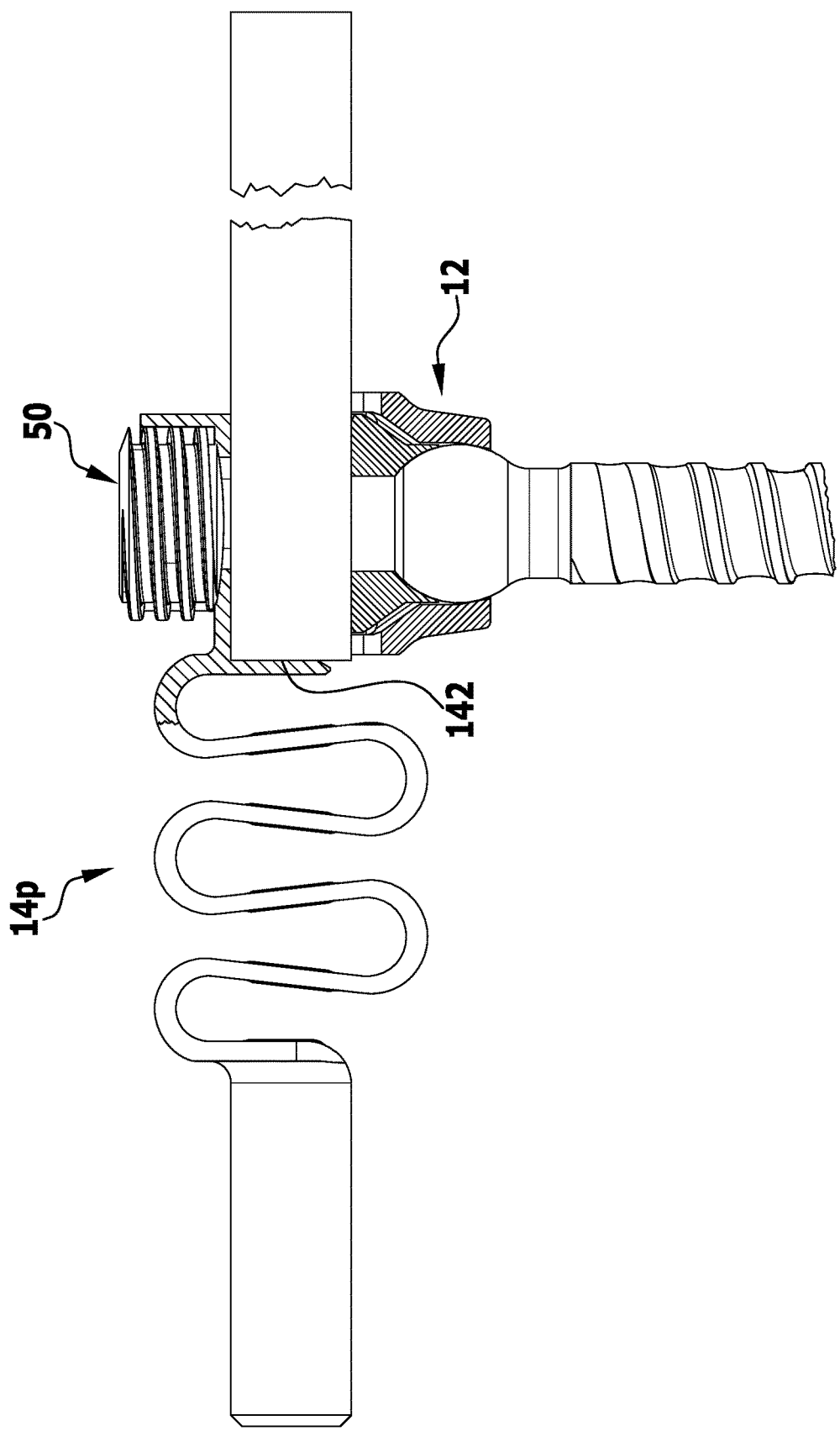
FIG. 63: is a partially sectional view of the arrangement of FIG. 62 along line 63-63.
Figure 64:
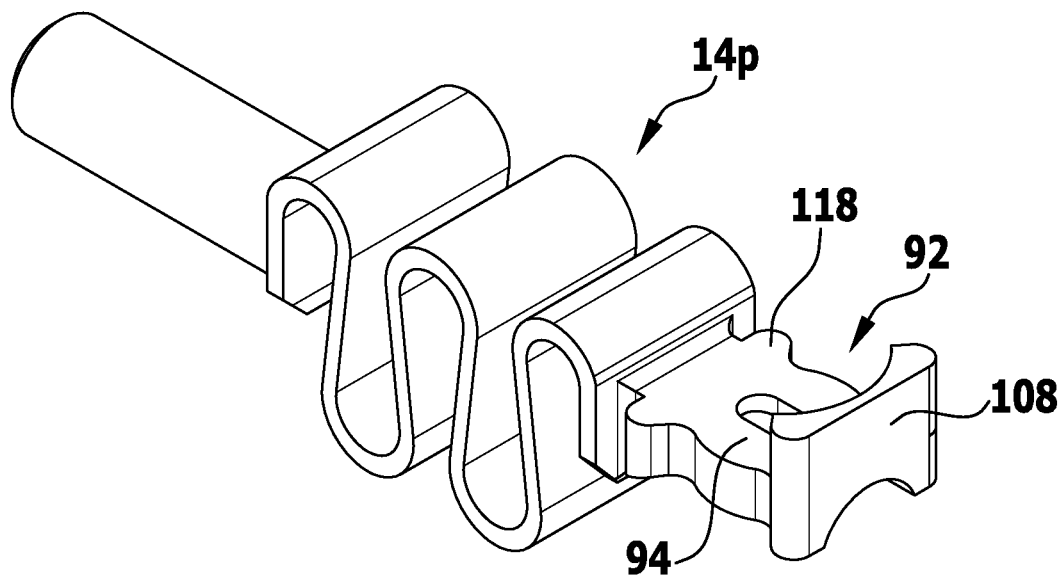
FIG. 64: is a perspective view of the connection element of FIG. 63 from above.
Figure 65:
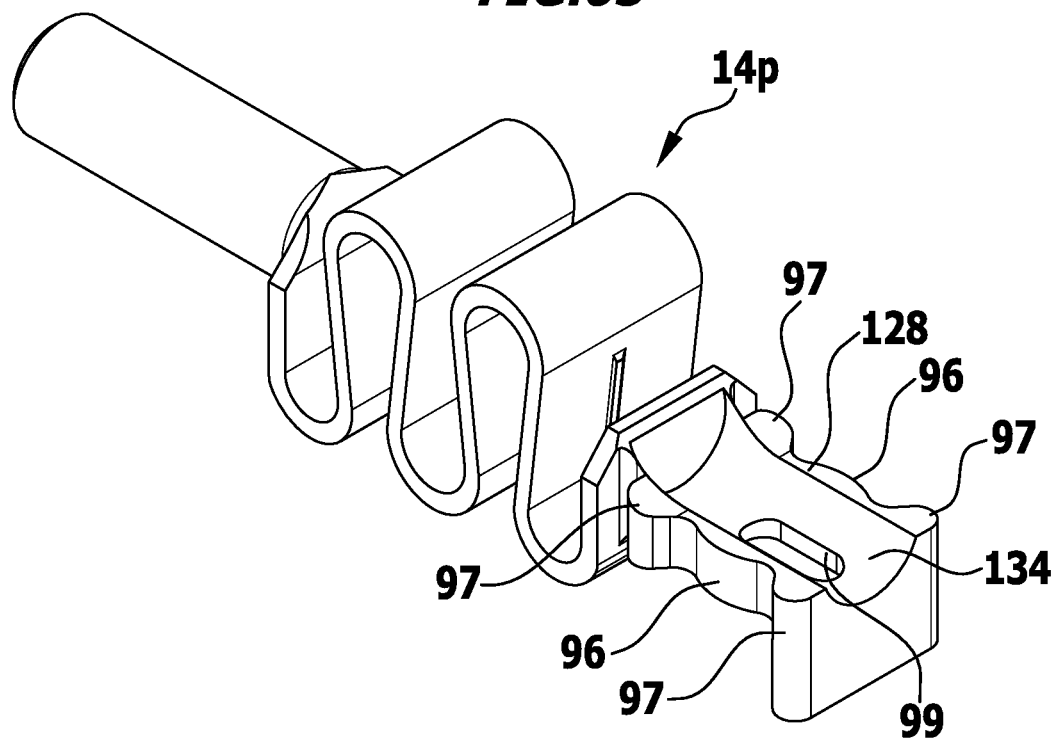
FIG. 65: is a perspective view of the connection element of FIG. 64 from below.
Figure 66:
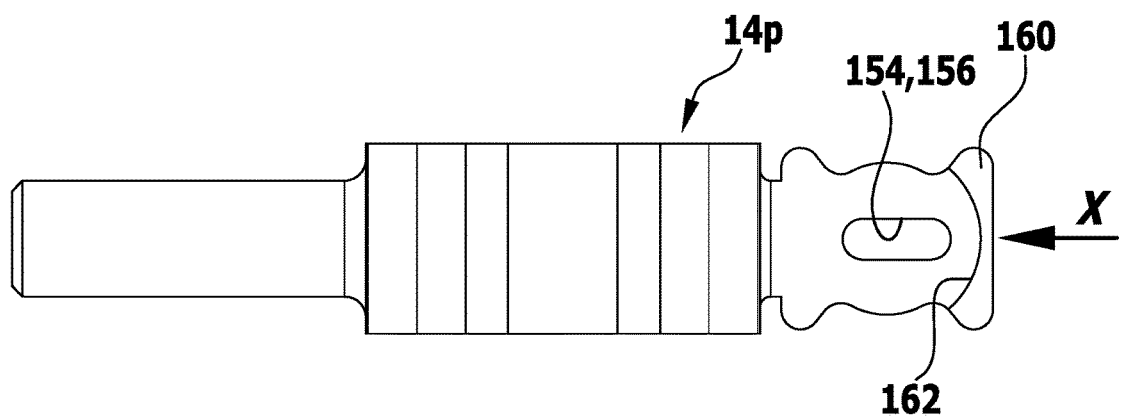
FIG. 66: is a view of the connection element of FIG. 67 in the direction of arrow Y.
Figure 67:
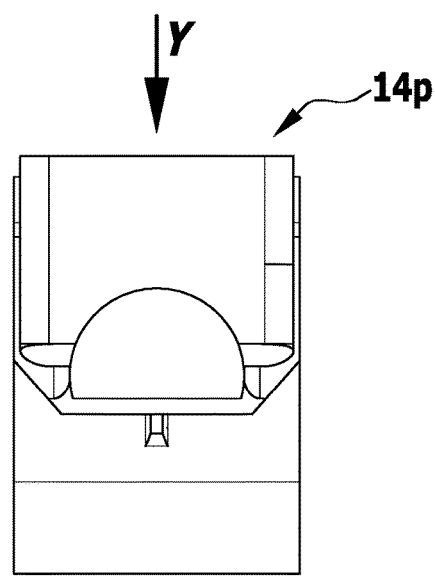
FIG. 67: is a view of the connection element of FIG. 66 in the direction of arrow X.

FIGS. 54 to 56 are schematic representations of a thirteenth and a fourteenth exemplary embodiment of a connection element, designated with reference signs 14l and 14m. The connection elements 14l and 14m differ from the connection element 14 in the configuration of their coupling elements 92.

The coupling element 92 of the connection element 14l has a substantially cuboidal main body. Two coupling members 96 in the form of coupling projections 102 protrude therefrom transversely of the longitudinal axis 72 and facing in diametrically opposed directions. These are curved convexly away from the coupling element main body 94 and together define an external diameter which corresponds to an internal diameter of the internal thread 46.

On the bottom 128, parallel to the longitudinal axis 72, two coupling members 98 take the form of lateral set-back portions 100, which are dimensioned and arranged such that they may be placed onto the edges 126 of the insert 54. The bottom 128 is planar. The top 118 is likewise planar and forms a connection element contact face 134 for application against the connection element 14m. In addition, a coupling member 99 in the form of a coupling projection protrudes from the top 118 in a direction transverse to the longitudinal axis 72. The coupling member 99 is of substantially elongate, cuboidal construction with rounded end edges and slightly inclined side faces, so as to form overall a slightly conical projection.

The coupling element 92 of the connection element 14m has a substantially cuboidal coupling element main body 94, away from which two coupling members 96 in the form of coupling projections 102 extend transversely of the longitudinal axis 72 in diametrically opposed directions.

The coupling projections 102 are curved convexly away from the coupling element main body 94 and together define common an external diameter which corresponds to an internal diameter of the internal thread 46.

The coupling members 96 are adjoined on their side facing away from the intermediate portion 74 by two coupling members 97 in the form of coupling projections, which have an outer contour conformed to the side faces 130 of the wall portions 44.

In addition, the coupling element 92 is provided with a coupling recess 144 extending transversely of the longitudinal axis 72 and taking the form of a through opening 156. The through opening 156 substantially takes the shape of an elongate hole with rounded corners. Moreover, it is slightly conical, such that the coupling member 99 may be inserted in positive-locking manner into the coupling recess 154.

The bottom 128 of the coupling element 92 of the connection element 14m is planar, like the top 118. The top 118 forms a planar clamping surface portion 122 for the distal end 124 of the fixing screw 50.

Like the connection elements 14j and 14k, the connection elements 14l and 14m may be coupled together and fixed jointly to a single bone screw 16. To this end, first of all the coupling element 92 of the connection element 14l is inserted into the connection element receptacle 42, such that the coupling member 99 faces away from the fixing part 24. Then the coupling element 92 of the connection element 14m may be inserted into the connection element receptacle 42, such that the coupling recess 154 receives the coupling member 99. Finally the coupling elements 92 may be fixed in clamped manner to the holding part.

FIGS. 57 to 61 are schematic representations of two further exemplary embodiments of connection elements designated with the reference signs 14n and 14o. They differ from the connection element 14 in the configuration of their coupling elements 92.

The connection element 14n has a coupling element 92, which corresponds substantially to the coupling element 92 of the connection element 14h. It differs merely in the configuration of a coupling member 99 in the form of a coupling recess 154.

The coupling recess 154 extends from the end face 108 towards the intermediate portion 74, in such a way that its width decreases, such that overall an equal-sided prism is formed as a hollow. The coupling recess 154 also extends from the top 118. In other words, the coupling recess 154 opens away from the top 118 and from the end face 108.

The top 118 furthermore forms a planar clamping surface portion 122. A boundary face 158 of the coupling recess 154 extending parallel to the bottom 128 forms a connection element contact face 134 for application against the connection element 14o, specifically the coupling element 92 thereof.

The coupling element 92 of the connection element 14o has the shape of an equal-sided prism and corresponds to the coupling recess 154. The coupling element 92 may thus be introduced completely into the coupling recess 154, as illustrated schematically by way of example in FIG. 60.

The top 118 of the coupling element 92 of the connection element 14o furthermore forms a planar clamping surface portion 122. The bottom 128 of the coupling element 92 abuts the boundary face 158.

The coupled-together coupling elements 92 of the connection elements 14n and 14o together form a unit, which has the same shape as the coupling element 92 of the connection element 14h. Using the fixing screw 50, the two connection elements 14n and 14o may be secured to the bone screw 16 in a direction parallel to the longitudinal axis 72 and against rotation about the same.

FIGS. 62 to 67 are schematic representations of a seventeenth exemplary embodiment of a connection element designated overall with the reference sign 14p. It differs from the connection element 14 in the configuration of the coupling element 92.

The coupling element 92 of the connection element 14p corresponds in structure substantially to the coupling element 92 of the connection element 14c. Two coupling members 96 protrude laterally from a substantially cuboidal coupling element main body 94 in diametrically opposing directions, which define a common external diameter conformed to an internal diameter of the internal thread 46.

The coupling members 97 protruding on either side of the coupling members 96 have an external contour which is in turn conformed to the concave side faces 130 of the wall portions 44. The coupling members 97 formed at the free end of the coupling element 92 additionally extend beyond the top 118 and thereby enlarge the end face 108 of the coupling element 92 in comparison with the end face 108 of the coupling element 92 of the connection element 14c. Overall, an end wall 160 is formed in this way which has a side face 162 facing in the direction of the intermediate portion 74, which side face takes the form of a hollow-cylindrical wall portion. An internal diameter defined by the side face 162 is conformed to an external diameter of the external thread 48 of the fixing screw 50.

The width of the end wall 160 corresponds substantially to the distance between the two wall portions 44, such that the end wall 160 closes the connection element receptacle 42 in a direction facing away from the intermediate portion 44.

The coupling element 92 further comprises a further coupling member 99 in the form of a coupling recess 154, which takes the form of a through opening 156, specifically the form of an elongate hole. The through opening connects the top 118 with the hollow-cylindrical connection element contact face 134, which is formed on the bottom 128 of the coupling element 92. The through opening 156 allows the use of a fixing screw 50, which is inserted conventionally, i.e. it does not comprise a substantially planar distal end 124 but rather an end which tapers to a point.

Like the connection element 14c, the connection element 14p, together with an elongate, circular cylindrical connecting rod 132, allows fixing with the fixing screw 50 in the connection element receptacle 42 of the bone screw 16. The connection element 14p thus allows connecting rods 132 to be extended simply and without further auxiliary means.

The above-described exemplary embodiments of connection elements may be produced from biocompatible metals or plastics. They are preferably of one-piece construction.

The coupling elements of the connection elements may be combined in virtually any desired way. They may optionally be arranged or formed on connection elements with resilient intermediate portions 74 or indeed on non-resilient or substantially non-resilient intermediate portions, for example on circular cylindrical connecting rods. In particular it is also conceivable for connection elements to have two coupling elements. These may be of identical or indeed different configuration.

Furthermore, the described coupling members may be combined with one another in principle in any desired manner for the coupling elements. For example, through openings may also be provided on coupling elements which were described above and did not have any through openings.

What is claimed is:

1. A connection element for a spine stabilization system, comprising:
   a first end for fixing to a first bone fixation device,
   a second end for fixing to a second bone fixation device, and
   an intermediate portion arranged or formed between the first and second ends and defining a longitudinal axis, wherein:
   at least one of the first and second ends takes the form of a coupling element for fixing the connection element to a bone fixation device in at least one defined orientation relative to the longitudinal axis,
   the coupling element has a shape other than a circular cylinder;
   the coupling element comprises a coupling element main body having a planar bottom side and at least one coupling member arranged or formed on the coupling element main body, and
   the at least one coupling member extends parallel to the longitudinal axis and comprises set-back portions on the bottom side thereof, the set-back portions having one side face each which extends parallel to the bottom side.

2. The connection element according to claim 1, wherein at least one of:
   the first and second ends take the form of a coupling element having a shape other than a circular cylinder,
   the coupling element is of a one-piece construction, and
   the connection element is of a one-piece construction.

3. The connection element according to claim 1, wherein:
   the at least one coupling member extends in a coupling member direction which extends parallel to or transversely of the longitudinal axis.

4. The connection element according to claim 1, wherein:
   the coupling element main body takes the form of a straight or oblique general cylinder, and
   a cylinder longitudinal axis defined by the cylinder extends transversely of the longitudinal axis.

5. The connection element according to claim 1, wherein:
   the at least one coupling member comprises a coupling projection or a coupling receptacle.

6. The connection element according to claim 1, wherein at least one of:
   the coupling element is mirror-symmetrical relative to a mirror plane containing the longitudinal axis,
   a center of gravity of the coupling element is spaced from the longitudinal axis, and
   an end face of the coupling element facing away from the intermediate portion is inclined relative to the longitudinal axis or rounded.

7. The connection element according to claim 1, wherein:
   the coupling element comprises a connection element contact face for application against a further connection element, in particular against an end of the further connection element.

8. The connection element according to claim 7, wherein at least one of:
   the connection element contact face at least in part takes the form of a hollow-cylindrical wall face, and
   the connection element contact face at least in part takes the form of a planar contact face portion.

9. The connection element according to claim 1, wherein the intermediate portion is a winding leaf spring element in the form of a strip and comprises at least one recess open laterally in a recess direction transverse to the longitudinal axis.

10. The connection element according to claim 1, wherein the connection element is made from a metallic material or a plastics material.

11. The connection element according to claim 1, wherein the intermediate portion is at least in part flexible.

12. The connection element according to claim 1, wherein:
   the at least one coupling member comprises coupling projections which protrude laterally from the coupling element main body transversely to the longitudinal axis.

13. The connection element according to claim 1, wherein the coupling element comprises a top which forms a planar clamping surface portion.

14. The connection element according to claim 1, wherein:
   the coupling element comprises a top which forms a planar clamping surface portion.

15. A spine stabilization system, comprising:
   at least one first bone fixation device,
   at least one second bone fixation device, and
   at least one connection element, the at least one connection element comprising:
   a first end for fixing to the at least one first bone fixation device, a second end for fixing to the at least one second bone fixation device, and an intermediate portion arranged or formed between the first and second ends and defining a longitudinal axis, wherein:

at least one of the first and second ends takes the form of a coupling element for fixing the connection element to the at least one first of the at least one second bone fixation device in at least one defined orientation relative to the longitudinal axis, the coupling element has a shape other than a circular cylinder, the coupling element comprises a coupling element main body having a planar bottom side and at least one coupling member arranged or formed on the coupling element main body, and the at least one coupling member extends parallel to the longitudinal axis and comprises set-back portions on the bottom side thereof, the set-back portions having one side face each which extends parallel to the bottom side.

16. The spine stabilization system according to claim 15, wherein:

the at least one coupling member comprises coupling projections which protrude laterally from the coupling element main body transversely to the longitudinal axis.

17. The spine stabilization system according to claim 15, wherein the coupling element comprises a top forming a planar clamping surface portion.

18. The spine stabilization system according to claim 15, wherein:

the coupling element comprises a top forming a planar clamping surface portion.

19. A connection element for a spine stabilization system, comprising:

a first end for fixing to a first bone fixation device, a second end for fixing to a second bone fixation device, and an intermediate portion arranged or formed between the first and second ends and defining a longitudinal axis, wherein:

at least one of the first and second ends takes the form of a coupling element for fixing the connection element to a bone fixation device in at least one defined orientation relative to the longitudinal axis, and the coupling element has a shape other than a circular cylinder, the coupling element comprises a coupling element main body and first coupling members in the form of coupling projections arranged or formed on each side of the coupling element main body, which first coupling members protrude laterally from the coupling element main body transversely to the longitudinal axis, and each of the first coupling members is adjoined both on a side facing the intermediate portion and on a side remote therefrom by two second coupling members, which likewise take the form of coupling projections.

20. A spine stabilization system, comprising:

at least one first bone fixation device, at least one second bone fixation device, and at least one connection element, the at least one connection element comprising:

a first end for fixing to the at least one first bone fixation device, a second end for fixing to the at least one second bone fixation device, and an intermediate portion arranged or formed between the first and second ends and defining a longitudinal axis, wherein:

at least one of the first and second ends takes the form of a coupling element for fixing the connection element to a bone fixation device in at least one defined orientation relative to the longitudinal axis, and the coupling element has a shape other than a circular cylinder, the coupling element comprises a coupling element main body and first coupling members in the form of coupling projections arranged or formed on each side of the coupling element main body, which first coupling members protrude laterally from the coupling element main body transversely to the longitudinal axis, and each of the first coupling members is adjoined both on a side facing the intermediate portion and on a side remote therefrom by two second coupling members, which likewise take the form of coupling projections.

* * * * *